(12) United States Patent
Akama et al.

(10) Patent No.: US 8,853,186 B2
(45) Date of Patent: Oct. 7, 2014

(54) BORON CONTAINING SMALL MOLECULES

(71) Applicants: Eli Lilly and Company, Indianapolis, IN (US); Anacor Pharmaceuticals, Inc., Palo Alto, CA (US)

(72) Inventors: Tsutomu Akama, Sunnyvale, CA (US); Terry William Balko, Greenfield, IN (US); Jean Marie Defauw, New Palestine, IN (US); Jacob J. Plattner, Orinda, CA (US); William Hunter White, Greenfield, IN (US); Joseph Raymond Winkle, Carmel, IN (US); Yong-Kang Zhang, San Jose, CA (US); Yasheen Zhou, Moraga, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 146 days.

(21) Appl. No.: 13/678,576

(22) Filed: Nov. 16, 2012

(65) Prior Publication Data
US 2013/0131016 A1    May 23, 2013

Related U.S. Application Data

(60) Provisional application No. 61/562,373, filed on Nov. 21, 2011.

(51) Int. Cl.
  *C07F 5/02* (2006.01)
  *A01N 43/80* (2006.01)
  *A61K 31/69* (2006.01)

(52) U.S. Cl.
  CPC . *C07F 5/027* (2013.01); *C07F 5/02* (2013.01); *A01N 43/80* (2013.01); *A61K 31/69* (2013.01); *C07F 5/025* (2013.01)
  USPC ............................................. 514/64; 548/110

(58) Field of Classification Search
  CPC ......................................................... C07F 5/02
  USPC ............................................. 514/64; 548/110
  See application file for complete search history.

(56) References Cited

FOREIGN PATENT DOCUMENTS

WO     WO 2006/089067    *   8/2006

* cited by examiner

*Primary Examiner* — Joseph Kosack
(74) *Attorney, Agent, or Firm* — Morgan, Lewis & Bockius LLP

(57) ABSTRACT

This invention provides novel compounds, methods of using the compounds, and pharmaceutical formulations comprising the compounds.

20 Claims, No Drawings

BORON CONTAINING SMALL MOLECULES

CROSS REFERENCE TO RELATED APPLICATIONS

This application claims priority under 35 U.S.C. §119(e) to U.S. Provisional Application Ser. No. 61/562,373, filed on Nov. 21, 2011, incorporated by reference herein in its entirety.

Ectoparasites such as fleas, lice, flies, mosquitoes, ticks and mites are problematic for man and animal alike. Such ectoparasites seriously impact productivity in the domesticated animal industry by reducing weight gain, causing poor quality hide, wool, and meat, and in some cases resulting in death. Ectoparasites are also responsible, in part, for the spread of disease and discomfort in food and companion animals. Ectoparasites in particular are known to harbor and transmit a variety of microbial pathogens, including bacteria, viruses and protozoan parasites, many of which are pathogenic to humans, other warm-blooded mammals and birds. Diseases in which ectoparasites have been implicated include, but are not limited to, malaria, scabies, rosacea, lymphatic- and blood-born filariasis, trachoma, trypanosomiasis, Leishmaniasis, Rocky Mountain Spotted Fever, Lyme Disease, babesiosis, and food-borne illnesses due to *Salmonella, E. coli* and *Campylobacter*, for example.

The medical importance of ectoparasiticide infestations has prompted the development of reagents capable of controlling such infestations. Commonly encountered methods to control ectoparasiticide infestations, for example, have generally focused on use of insecticides, which are often unsuccessful or unsatisfactory for one or more of the following reasons: (1) failure of owner or applicator compliance (frequent administration is required); (2) behavioral or physiological intolerance of the animal to the pesticide product or means of administration; (3) the emergence of ectoparasites resistant to the reagent; and (4) negative impact on the environment and/or toxicity.

Specifically, ticks parasitize wild as well as domesticated animals and humans, and are known or suspected to be responsible for the transmission of pathogens including bacteria, viruses and protozoan parasites. Currently, ticks are considered to be second in the world to mosquitoes as vectors of human diseases, but they are considered to be the most important vector of pathogens in North America. Effective elimination of tick infestations is difficult and often impractical, due to the need for concomitant treatment of the immediate host as well as the environmental reservoir. Presently, tick control is effected by integrated pest management in which different control methods are adapted to one area or against one tick species with due consideration to their environmental effects.

While the use of insecticides and pesticides have been beneficial, alternative or improved compounds, formulations, and methods are needed. Desirable compounds, formulations, and methods would not only provide alternative therapies, but would also overcome at least some limitations of current approaches. Such limitations include toxicity and safety of both the animal and the user/owner, limited efficacy (potency and duration), and resistance issues. Also impacting the beneficial use of insecticides and pesticides are administration obstacles, which include mode and recurrence of administration. For example, reducing the frequency of administration while maintaining efficacy is desirable, as excessive and repeated treatment of animals is often inconvenient and/or difficult.

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, pharmaceutically acceptable excipients, or the like, disclosed herein and as such may vary.

The abbreviations used herein generally have their conventional meaning within the chemical and biological arts.

The following abbreviations have been used: Ac is acetyl; AcOH is acetic acid; ACTBr is acetyltrimethylammonium bromide; AIBN is azobisisobutyronitrile or 2,2 azobisisobutyronitrile; aq. is aqueous; Ar is aryl; $B_2pin_2$ is bis(pinacolato) diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2(pddf)$ is 1,1'-Bis(diphenylphosphino) ferrocene]dichloropalladium (II); Pd/C is the catalyst known as palladium on carbon; $Pd_2(dba)_3$ is an organometallic catalyst known as tris(dibenzylideneacetone)dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$-$PhSO_2Cl$ is 3-fluoro-4-nitrophenylsulfonyl chloride; 2-MeO-4-$NO_2$-$PhSO_2Cl$ is 2-methoxy-4-nitrophenylsulfonyl chloride; and (EtO)$_2$POCH$_2$COOEt is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

An "additional therapeutic agent" refers to a compound (or a salt, (e.g. pharmaceutically acceptable salt), prodrug, solvate and hydrate thereof) that is administered in combination with a compound of the invention or with a compound described herein. In an exemplary embodiment, the additional therapeutic agent exhibits activity against an ectoparasite, such as a tick and/or flea, and therefore has the potential to kill and/or inhibit the growth of an ectoparasite. In an exemplary embodiment, the additional therapeutic agent is a compound (or a salt, (e.g. pharmaceutically acceptable salt), prodrug, solvate and hydrate thereof) described herein. In an exemplary embodiment, the additional therapeutic agent is a compound (or a salt, (e.g. pharmaceutically acceptable salt), prodrug, solvate and hydrate thereof) known in the art. An additional therapeutic agent can itself be formulated for administration according to methods described herein or known in the art.

The term "poly" as used herein means at least 2. For example, a polyvalent metal ion is a metal ion having a valency of at least 2.

"Moiety" refers to a radical of a molecule that is attached to the remainder of the molecule.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkyl.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined herein. Thus, the term "arylalkyl" is meant to include those radicals in which an aryl group is attached to an alkyl group (e.g., benzyl, phenethyl, pyridiylethyl and the like) including those alkyl groups in which a carbon atom (e.g. a methylene group) has been replaced by, for example, an oxygen atom (e.g., phenoxymethyl, 2-pyridyloxymethyl, 3-(1-naphthyloxy)propyl, and the like).

For brevity, the term "heteroaryl" when used in combination with other terms (e.g., heteroaryloxy, heteroarylthioxy, heteroarylalkyl) includes those radicals in which a heteroaryl group is attached through the next moiety to the rest of the molecule. Thus, the term "heteroarylalkyl" is meant to include those radicals in which a heteroaryl group is attached to an alkyl group (e.g., pyridylmethyl and the like). The term "heteroaryloxy" is meant to include those radicals in which a heteroaryl group is attached to an oxygen atom. The term "heteroaryloxyalkyl" is meant to include those radicals in which an aryl group is attached to an oxygen atom which is then attached to an alkyl group. (e.g., 2-pyridyloxymethyl and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R'", —NR"C(O)$_2$R', —NR'"'—C(NR'R"R"')=NR"", —NR""—C(NR'R") =NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2 m'+1), where m' is the total number of carbon atoms in such radical. R', R", R'", R"" and R""' each preferably independently refer to hydrogen, substituted or unsubstituted heteroalkyl, substituted or unsubstituted aryl, e.g., aryl substituted with 1 or 2 or 3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'-C(O)NR"R'", —NR"C(O)$_2$R', —NR""—C(NR'R"R"')=NR"", —NR""—C(NR'R") =NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 or 1 or 2 or 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer from 1 or 2 or 3 or 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers from 0 or 1 or 2 or 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$ or C$_2$ or C$_3$ or C$_4$ or C$_5$ or C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective" or "therapeutically effective" amount refers to the amount of drug needed to effect the desired therapeutic result.

The term "pharmaceutically acceptable salt" is meant to include a salt of a compound of the invention which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, or l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons, chiral catalysts, or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example deuterium ($^2$H), tritium ($^3$H), iodine-125 ($^{125}$I) or carbon-14 ($^{14}$C). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not negatively interfere with the effectiveness of the biological activity of the active agent, and that is sufficiently non-toxic to the host. Representative carriers include water, oils, both vegetable and mineral, cream bases, lotion bases, ointment bases and the like. These bases include suspending agents, thickeners, penetration enhancers, and the like. Their formulation is well known to those in the art of topical pharmaceuticals. Additional information concerning carriers can be found in *Remington: The Science and Practice of Pharmacy*, 21st Ed., Lippincott, Williams & Wilkins (2005) which is incorporated herein by reference.

The term "pharmaceutically acceptable excipient" is conventionally known to mean pharmaceutically acceptable carriers, pharmaceutically acceptable diluents and/or pharmaceutically acceptable vehicles used in formulating drug compositions effective for the desired use.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

The phrase "unit", as used herein, refers to the number of discrete objects to be administered which comprise the dosage form. In some embodiments, the dosage form includes a compound of the invention in one capsule or tablet. This is a single unit. In some embodiments, the dosage form includes a compound of the invention as part of a therapeutically effective dosage of a cream or gel or ointment. This is also a single unit. In some embodiments, the dosage form includes a compound of the invention and at least one additional therapeutic agent contained within one capsule or tablet, or as part of a therapeutically effective dosage of a cream or gel or ointment. This is a single unit, whether or not the interior of the capsule includes multiple discrete granules of the active ingredient(s). In some embodiments, the dosage form includes a compound of the invention in one capsule or tablet, and at least one additional therapeutic agent in a second capsule or tablet. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally.

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include $H^+$, $H_3O^+$, ammonium, potassium, calcium, magnesium, organic amino (such as choline or diethylamine or amino acids such as d-arginine, l-arginine, d-lysine, or l-lysine) and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of positively charged counterions include $H^+$, $H_3O^+$, ammonium, potassium, calcium, magnesium, organic amino (such as choline or diethylamine or amino acids such as d-arginine, l-arginine, d-lysine, l-lysine), and sodium. These salts of the compounds are implicitly contained in descriptions of these compounds.

In one aspect, the invention provides a compound of the invention. In an exemplary embodiment, the invention provides a compound described herein. In an exemplary embodiment, the invention is a compound according to a formula described herein.

The invention provides compounds having a structure of formula (I):

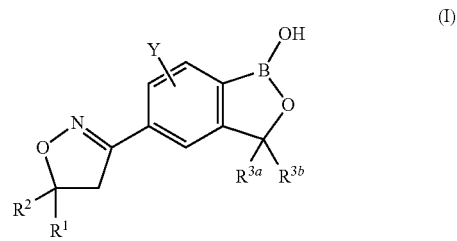

wherein Y is hydrogen, fluoro, chloro, or bromo;
$R^1$ is phenyl substituted 2-4 times, said substitutions comprising i) 1-4 substitutions with the same or different of halo (preferably fluoro, chloro, or bromo), and 0-1 substitutions with methyl, difluoromethyl, trifluoromethyl, methoxy, trifluormethoxy, or trifluoroethoxy, or ii) 2 trifluoromethyl groups;

$R^2$ is methyl, fluoromethyl, trifluoromethyl, or perfluoroethyl;

$R^{3a}$ and $R^{3b}$ are independently selected from hydrogen, methyl, ethyl, or fluoromethyl, or $R^{3a}$ and $R^{3b}$ combine with the carbon to which they are attached to form a cyclopentyl ring or a cyclohexyl ring;

or a salt thereof.

In an exemplary embodiment, the compound, or a salt thereof, has a structure which is a formula described herein, wherein Y, $R^1$, $R^2$, $R^{3a}$, and $R^{3b}$ are as described herein. In an exemplary embodiment, the compound, or a salt thereof, has a structure which is formula (I), wherein Y, $R^1$, $R^2$, $R^{3a}$, and $R^{3b}$ are as described herein. In an exemplary embodiment, the compound, or a salt thereof, has a structure which is a formula described herein, wherein $R^1$, $R^2$, $R^{3a}$, and $R^{3b}$ are as described herein, and Y is H. In an exemplary embodiment, the compound, or a salt thereof, has a structure which is a formula described herein, wherein $R^1$, $R^2$, $R^{3a}$, and $R^{3b}$ are as described herein, and Y is F. In an exemplary embodiment, the compound, or a salt thereof, has a structure which is a formula described herein, wherein $R^1$, $R^2$, $R^{3a}$, and $R^{3b}$ are as described herein, and Y is Cl. In an exemplary embodiment, the compound, or a salt thereof, has a structure which is a formula described herein, wherein $R^1$, $R^2$, $R^{3a}$, and $R^{3b}$ are as described herein, and Y is Br. In an exemplary embodiment, the compound, or a salt thereof, has a structure which is formula (I), wherein $R^1$, $R^2$, $R^{3a}$, $R^{3b}$ and Y is H. In an exemplary embodiment, the compound, or a salt thereof, has a structure which is formula (I), wherein $R^1$, $R^2$, $R^{3a}$, $R^{3b}$ and Y is F.

In an exemplary embodiment, Y, $R^1$, $R^2$ and $R^{3a}$ are as described herein, and $R^{3b}$ is H. In an exemplary embodiment, Y, $R^1$, $R^2$ and $R^{3a}$ are as described herein, and $R^{3b}$ is unsubstituted alkyl. In an exemplary embodiment, Y, $R^1$, $R^2$ and $R^{3a}$ are as described herein, and $R^{3b}$ is methyl or ethyl or propyl or isopropyl. In an exemplary embodiment, Y, $R^1$, $R^2$ and $R^{3a}$ are as described herein, and $R^{3b}$ is methyl.

In an exemplary embodiment, Y, $R^1$ and $R^2$ are as described herein, and $R^{3a}$ is H and $R^{3b}$ is H. In an exemplary embodiment, $R^1$ and $R^2$ are as described herein, Y is H, and $R^{3a}$ is H and $R^{3b}$ is H. In an exemplary embodiment, $R^1$ and $R^2$ are as described herein, Y is F, and $R^{3a}$ is H and $R^{3b}$ is H. In an exemplary embodiment, $R^1$ and $R^2$ are as described herein, Y is Cl, and $R^{3a}$ is H and $R^{3b}$ is H. In an exemplary embodiment, Y, $R^1$ and $R^2$ are as described herein, and $R^{3a}$ is methyl and $R^{3b}$ is methyl. In an exemplary embodiment, $R^1$ and $R^2$ are as described herein, Y is H, and $R^{3a}$ is methyl and $R^{3b}$ is methyl. In an exemplary embodiment, $R^1$ and $R^2$ are as described herein, Y is F, and $R^{3a}$ is methyl and $R^{3b}$ is methyl. In an exemplary embodiment, $R^1$ and $R^2$ are as described herein, Y is Cl, and $R^{3a}$ is methyl and $R^{3b}$ is methyl. In an exemplary embodiment, Y, $R^1$ and $R^2$ are as described herein, and $R^{3a}$ is ethyl and $R^{3b}$ is ethyl. In an exemplary embodiment, $R^1$ and $R^2$ are as described herein, Y is H, and $R^{3a}$ is ethyl and $R^{3b}$ is ethyl. In an exemplary embodiment, $R^1$ and $R^2$ are as described herein, Y is F, and $R^{3a}$ is ethyl and $R^{3b}$ is ethyl. In an exemplary embodiment, $R^1$ and $R^2$ are as described herein, Y is Cl, and $R^{3a}$ is ethyl and $R^{3b}$ is ethyl. In an exemplary embodiment, Y, $R^1$ and $R^2$ are as described herein, and $R^{3a}$ is fluoromethyl and $R^{3b}$ is fluoromethyl. In an exemplary embodiment, $R^1$ and $R^2$ are as described herein, Y is H, and $R^{3a}$ is fluoromethyl and $R^{3b}$ is fluoromethyl. In an exemplary embodiment, $R^1$ and $R^2$ are as described herein, Y is F, and $R^{3a}$ is fluoromethyl and $R^{3b}$ is fluoromethyl. In an exemplary embodiment, $R^1$ and $R^2$ are as described herein, Y is Cl, and $R^{3a}$ is fluoromethyl and $R^{3b}$ is fluoromethyl.

In an exemplary embodiment, $R^1$ and $R^2$ are as described herein, Y is H, and $R^{3a}$ is H and $R^{3b}$ is methyl. In an exemplary embodiment, $R^1$ and $R^2$ are as described herein, Y is F, and $R^{3a}$ is H and $R^{3b}$ is methyl. In an exemplary embodiment, $R^1$ and $R^2$ are as described herein, Y is Cl, and $R^{3a}$ is H and $R^{3b}$ is methyl. In an exemplary embodiment, $R^1$ and $R^2$ are as described herein, Y is H, and $R^{3a}$ is H and $R^{3b}$ is ethyl. In an exemplary embodiment, $R^1$ and $R^2$ are as described herein, Y is F, and $R^{3a}$ is H and $R^{3b}$ is ethyl. In an exemplary embodiment, $R^1$ and $R^2$ are as described herein, Y is Cl, and $R^{3a}$ is H and $R^{3b}$ is ethyl. In an exemplary embodiment, $R^1$ and $R^2$ are as described herein, Y is H, and $R^{3a}$ is H and $R^{3b}$ is fluoromethyl. In an exemplary embodiment, $R^1$ and $R^2$ are as described herein, Y is F, and $R^{3a}$ is H and $R^{3b}$ is fluoromethyl. In an exemplary embodiment, $R^1$ and $R^2$ are as described herein, Y is Cl, and $R^{3a}$ is H and $R^{3b}$ is fluoromethyl. In an exemplary embodiment, $R^1$ and $R^2$ are as described herein, Y is H, and $R^{3a}$ is methyl and $R^{3b}$ is ethyl. In an exemplary embodiment, $R^1$ and $R^2$ are as described herein, Y is F, and $R^{3a}$ is methyl and $R^{3b}$ is ethyl. In an exemplary embodiment, $R^1$ and $R^2$ are as described herein, Y is Cl, and $R^{3a}$ is methyl and $R^{3b}$ is ethyl. In an exemplary embodiment, $R^1$ and $R^2$ are as described herein, Y is H, and $R^{3a}$ is methyl and $R^{3b}$ is fluoromethyl. In an exemplary embodiment, $R^1$ and $R^2$ are as described herein, Y is F, and $R^{3a}$ is methyl and $R^{3b}$ is fluoromethyl. In an exemplary embodiment, $R^1$ and $R^2$ are as described herein, Y is Cl, and $R^{3a}$ is methyl and $R^{3b}$ is fluoromethyl. In an exemplary embodiment, $R^1$ and $R^2$ are as described herein, Y is H, and $R^{3a}$ is ethyl and $R^{3b}$ is fluoromethyl. In an exemplary embodiment, $R^1$ and $R^2$ are as described herein, Y is F, and $R^{3a}$ is ethyl and $R^{3b}$ is fluoromethyl. In an exemplary embodiment, $R^1$ and $R^2$ are as described herein, Y is Cl, and $R^{3a}$ is ethyl and $R^{3b}$ is fluoromethyl.

In an exemplary embodiment, Y, $R^1$, $R^{3a}$ and $R^{3b}$ are as described herein, and $R^2$ is methyl. In an exemplary embodiment, Y, $R^1$, $R^{3a}$ and $R^{3b}$ are as described herein, and $R^2$ is fluoromethyl. In an exemplary embodiment, Y, $R^1$, $R^{3a}$ and $R^{3b}$ are as described herein, and $R^2$ is trifluoromethyl. In an exemplary embodiment, Y, $R^1$, $R^{3a}$ and $R^{3b}$ are as described herein, and $R^2$ is perfluoromethyl. In an exemplary embodiment, Y and $R^1$ are as described herein, $R^2$ is methyl, $R^{3a}$ is H and $R^{3b}$ is H. In an exemplary embodiment, $R^1$ is as described herein, $R^2$ is methyl, Y is H, and $R^{3a}$ is H and $R^{3b}$ is H. In an exemplary embodiment, $R^1$ is as described herein, $R^2$ is methyl, Y is F, and $R^{3a}$ is H and $R^{3b}$ is H. In an exemplary embodiment, $R^1$ is as described herein, $R^2$ is methyl, Y is Cl, and $R^{3a}$ is H and $R^{3b}$ is H. In an exemplary embodiment, Y and $R^1$ are as described herein, $R^2$ is fluoromethyl, $R^{3a}$ is methyl and $R^{3b}$ is methyl. In an exemplary embodiment, $R^1$ is as described herein, $R^2$ is fluoromethyl, Y is H, and $R^{3a}$ is methyl and $R^{3b}$ is methyl. In an exemplary embodiment, $R^1$ is as described herein, $R^2$ is fluoromethyl, Y is F, and $R^{3a}$ is methyl and $R^{3b}$ is methyl. In an exemplary embodiment, $R^1$ is as described herein, $R^2$ is fluoromethyl, Y is Cl, and $R^{3a}$ is methyl and $R^{3b}$ is methyl. In an exemplary embodiment, Y, $R^1$ and $R^2$ are as described herein, and $R^{3a}$ is ethyl and $R^{3b}$ is ethyl. In an exemplary embodiment, $R^1$ is as described herein, $R^2$ is trifluoromethyl, Y is H, and $R^{3a}$ is ethyl and $R^{3b}$ is ethyl. In an exemplary embodiment, $R^1$ is as described herein, $R^2$ is trifluoromethyl, Y is F, and $R^{3a}$ is ethyl and $R^{3b}$ is ethyl. In an exemplary embodiment, $R^1$ is as described herein, $R^2$ is trifluoromethyl, Y is Cl, and $R^{3a}$ is ethyl and $R^{3b}$ is ethyl. In an exemplary embodiment, Y, $R^1$ and $R^2$ are as described herein, and $R^{3a}$ is fluoromethyl and $R^{3b}$ is fluoromethyl. In an exemplary embodiment, $R^1$ is as described herein, $R^2$ is perfluoromethyl, Y is H, and $R^{3a}$ is fluoromethyl and $R^{3b}$ is fluoromethyl. In an exemplary embodiment, $R^1$ is as described herein, $R^2$ is perfluoromethyl, Y is F, and $R^{3a}$ is fluoromethyl and $R^{3b}$ is fluoromethyl. In an exemplary embodiment, $R^1$ is as described herein, $R^2$ is perfluoromethyl, Y is Cl, and $R^{3a}$ is fluoromethyl and $R^{3b}$ is fluoromethyl.

In an exemplary embodiment, $R^1$ and $R^2$ are as described herein, Y is H, and $R^{3a}$ is H and $R^{3b}$ is methyl. In an exemplary embodiment, $R^1$ and $R^2$ are as described herein, Y is F, and $R^{3a}$ is H and $R^{3b}$ is methyl. In an exemplary embodiment, $R^1$ and $R^2$ are as described herein, Y is Cl, and $R^{3a}$ is H and $R^{3b}$ is methyl. In an exemplary embodiment, $R^1$ and $R^2$ are as described herein, Y is H, and $R^{3a}$ is H and $R^{3b}$ is ethyl. In an exemplary embodiment, $R^1$ and $R^2$ are as described herein, Y is F, and $R^{3a}$ is H and $R^{3b}$ is ethyl. In an exemplary embodiment, $R^1$ and $R^2$ are as described herein, Y is Cl, and $R^{3a}$ is H and $R^{3b}$ is ethyl. In an exemplary embodiment, $R^1$ and $R^2$ are as described herein, Y is H, and $R^{3a}$ is H and $R^{3b}$ is fluoromethyl. In an exemplary embodiment, $R^1$ and $R^2$ are as described herein, Y is F, and $R^{3a}$ is H and $R^{3b}$ is fluoromethyl. In an exemplary embodiment, $R^1$ and $R^2$ are as described herein, Y is Cl, and $R^{3a}$ is H and $R^{3b}$ is fluoromethyl. In an exemplary embodiment, $R^1$ and $R^2$ are as described herein, Y is H, and $R^{3a}$ is methyl and $R^{3b}$ is ethyl. In an exemplary embodiment, $R^1$ and $R^2$ are as described herein, Y is F, and $R^{3a}$ is methyl and $R^{3b}$ is ethyl. In an exemplary embodiment, $R^1$ and $R^2$ are as described herein, Y is Cl, and $R^{3a}$ is methyl and $R^{3b}$ is ethyl. In an exemplary embodiment, $R^1$ and $R^2$ are as described herein, Y is H, and $R^{3a}$ is methyl and $R^{3b}$ is fluoromethyl. In an exemplary embodiment, $R^1$ and $R^2$ are as described herein, Y is F, and $R^{3a}$ is methyl and $R^{3b}$ is fluoromethyl. In an exemplary embodiment, $R^1$ and $R^2$ are as described herein, Y is Cl, and $R^{3a}$ is methyl and $R^{3b}$ is fluoromethyl. In an exemplary embodiment, $R^1$ and $R^2$ are as described herein, Y is H, and $R^{3a}$ is ethyl and $R^{3b}$ is fluoromethyl. In an exemplary embodiment, $R^1$ and $R^2$ are as described herein, Y is F, and $R^{3a}$ is ethyl and $R^{3b}$ is fluoromethyl. In an exemplary embodiment, $R^1$ and $R^2$ are as described herein, Y is Cl, and $R^{3a}$ is ethyl and $R^{3b}$ is fluoromethyl.

In an exemplary embodiment, Y and $R^1$ are as described herein, $R^2$ is trifluoromethyl, $R^{3a}$ is H and $R^{3b}$ is H. In an exemplary embodiment, $R^1$ is as described herein, $R^2$ is trifluoromethyl, Y is H, and $R^{3a}$ is H and $R^{3b}$ is H. In an exemplary embodiment, $R^1$ is as described herein, $R^2$ is trifluoromethyl, Y is F, and $R^{3a}$ is H and $R^{3b}$ is H. In an exemplary embodiment, $R^1$ is as described herein, $R^2$ is trifluoromethyl, Y is Cl, and $R^{3a}$ is H and $R^{3b}$ is H. In an exemplary embodiment, Y and $R^1$ are as described herein, $R^2$ is trifluoromethyl, and $R^{3a}$ is methyl and $R^{3b}$ is methyl. In an exemplary embodiment, $R^1$ is as described herein, $R^2$ is trifluoromethyl, Y is H, and $R^{3a}$ is methyl and $R^{3b}$ is methyl. In an exemplary embodiment, $R^1$ is as described herein, $R^2$ is trifluoromethyl, Y is F, and $R^{3a}$ is methyl and $R^{3b}$ is methyl. In an exemplary embodiment, $R^1$ is as described herein, $R^2$ is trifluoromethyl, Y is Cl, and $R^{3a}$ is methyl and $R^{3b}$ is methyl. In an exemplary embodiment, Y and $R^1$ are as described herein, $R^2$ is trifluoromethyl, and $R^{3a}$ is ethyl and $R^{3b}$ is ethyl. In an exemplary embodiment, $R^1$ is as described herein, $R^2$ is trifluoromethyl, Y is H, and $R^{3a}$ is ethyl and $R^{3b}$ is ethyl. In an exemplary embodiment, $R^1$ is as described herein, $R^2$ is trifluoromethyl, Y is F, and $R^{3a}$ is ethyl and $R^{3b}$ is ethyl. In an exemplary embodiment, $R^1$ is as described herein, $R^2$ is trifluoromethyl, Y is Cl, and $R^{3a}$ is ethyl and $R^{3b}$ is ethyl. In an exemplary embodiment, Y and $R^1$ are as described herein, $R^2$ is trifluoromethyl, $R^{3a}$ is fluoromethyl and $R^{3b}$ is fluoromethyl. In an exemplary embodiment, $R^1$ is as described herein, $R^2$ is trifluoromethyl, Y is H, and $R^{3a}$ is fluoromethyl and $R^{3b}$ is fluoromethyl. In an exemplary embodiment, $R^1$ is as described herein, $R^2$ is trifluoromethyl, Y is F, and $R^{3a}$ is fluoromethyl and $R^{3b}$ is fluoromethyl. In an exemplary embodiment, $R^1$ is as described herein, $R^2$ is trifluoromethyl, Y is Cl, and $R^{3a}$ is fluoromethyl and $R^{3b}$ is fluoromethyl.

In an exemplary embodiment, $R^1$ is as described herein, $R^2$ is trifluoromethyl, Y is H, and $R^{3a}$ is H and $R^{3b}$ is methyl. In an exemplary embodiment, $R^1$ is as described herein, $R^2$ is trifluoromethyl, Y is F, and $R^{3a}$ is H and $R^{3b}$ is methyl. In an exemplary embodiment, $R^1$ is as described herein, $R^2$ is trifluoromethyl, Y is Cl, and $R^{3a}$ is H and $R^{3b}$ is methyl. In an exemplary embodiment, $R^1$ is as described herein, $R^2$ is trifluoromethyl, Y is H, and $R^{3a}$ is H and $R^{3b}$ is ethyl. In an exemplary embodiment, $R^1$ is as described herein, $R^2$ is trifluoromethyl, Y is F, and $R^{3a}$ is H and $R^{3b}$ is ethyl. In an exemplary embodiment, $R^1$ is as described herein, $R^2$ is trifluoromethyl, Y is Cl, and $R^{3a}$ is H and $R^{3b}$ is ethyl. In an exemplary embodiment, $R^1$ is as described herein, $R^2$ is trifluoromethyl, Y is H, and $R^{3a}$ is H and $R^{3b}$ is fluoromethyl. In an exemplary embodiment, $R^1$ is as described herein, $R^2$ is trifluoromethyl, Y is F, and $R^{3a}$ is H and $R^{3b}$ is fluoromethyl. In an exemplary embodiment, $R^1$ is as described herein, $R^2$ is trifluoromethyl, Y is Cl, and $R^{3a}$ is H and $R^{3b}$ is fluoromethyl. In an exemplary embodiment, $R^1$ is as described herein, $R^2$ is trifluoromethyl, Y is H, and $R^{3a}$ is methyl and $R^{3b}$ is ethyl. In an exemplary embodiment, $R^1$ is as described herein, $R^2$ is trifluoromethyl, Y is F, and $R^{3a}$ is methyl and $R^{3b}$ is ethyl. In an exemplary embodiment, $R^1$ is as described herein, $R^2$ is trifluoromethyl, Y is Cl, and $R^{3a}$ is methyl and $R^{3b}$ is ethyl. In an exemplary embodiment, $R^1$ is as described herein, $R^2$ is trifluoromethyl, Y is H, and $R^{3a}$ is methyl and $R^{3b}$ is fluoromethyl. In an exemplary embodiment, $R^1$ is as described herein, $R^2$ is trifluoromethyl, Y is F, and $R^{3a}$ is methyl and $R^{3b}$ is fluoromethyl. In an exemplary embodiment, $R^1$ is as described herein, $R^2$ is trifluoromethyl, Y is Cl, and $R^{3a}$ is methyl and $R^{3b}$ is fluoromethyl. In an exemplary embodiment, $R^1$ is as described herein, $R^2$ is trifluoromethyl, Y is H, and $R^{3a}$ is ethyl and $R^{3b}$ is fluoromethyl. In an exemplary embodiment, $R^1$ is as described herein, $R^2$ is trifluoromethyl, Y is F, and $R^{3a}$ is ethyl and $R^{3b}$ is fluoromethyl. In an exemplary embodiment, $R^1$ is as described herein, $R^2$ is trifluoromethyl, Y is Cl, and $R^{3a}$ is ethyl and $R^{3b}$ is fluoromethyl.

In an exemplary embodiment, the compound has a structure according to the following formula:

wherein Y, $R^1$, $R^2$, $R^{3a}$ and $R^{3b}$ are as described herein, and C* is a carbon atom which is a stereocenter having a configuration which is (R) or (S). In an exemplary embodiment, Y, $R^1$, $R^2$, $R^{3a}$ and $R^{3b}$ are as described herein, and C* is a stereocenter with a (R) configuration. In an exemplary embodiment, Y, $R^1$, $R^2$, $R^{3a}$ and $R^{3b}$ are as described herein, and C* is a stereocenter with a (S) configuration.

The invention further provides compounds of the structure

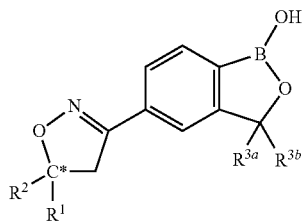

wherein C* is a carbon atom which is a stereocenter having a (S) configuration, or a salt thereof. The invention further provides compound of the structure:

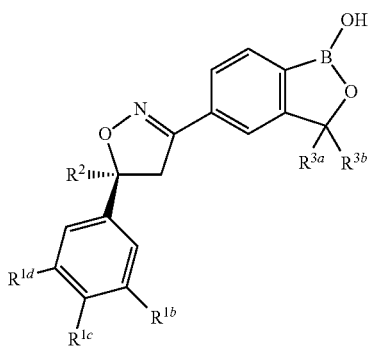

wherein $R^{1b}$, $R^{1c}$, and $R^{1d}$ are each independently selected from hydrogen, fluoro, chloro, bromo, methyl, difluoromethyl, trifluoromethyl, methoxy, trifluormethoxy, or trifluoroethoxy, and $R^{3a}$ and $R^{3b}$ are selected from $CH_3$ or $CH_2F$, and salts thereof.

The invention further provides compounds of the structure:

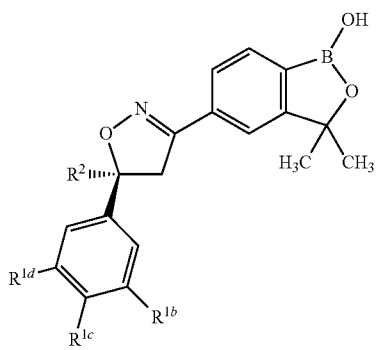

wherein $R^2$ is $CF_3$; and $R^{1b}$, $R^{1c}$ and $R^{1d}$ are each independently selected from hydrogen, fluoro, chloro, or bromo or a salt thereof, and compounds wherein $R^2$ is $CF_3$, $R^{1b}$ is fluoro, chloro, or bromo; $R^{1c}$ is hydrogen, fluoro, or chloro; and $R^{1d}$ is fluoro, chloro, or bromo, or a salt thereof.

The following table provides examples of the compound of the invention, according to the formula

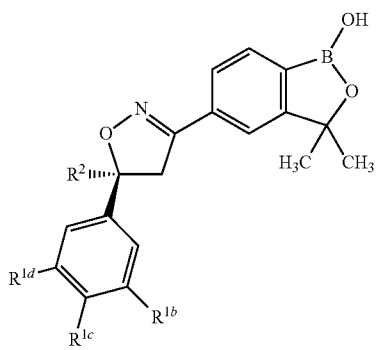

|       | $R^{1b}$ | $R^{1c}$ | $R^{1d}$ |
|---|---|---|---|
| F     | F  | H  | H  |
|       | H  | F  | H  |
|       | H  | H  | F  |
|       | F  | F  | H  |
|       | F  | H  | F  |
|       | H  | F  | F  |
|       | F  | F  | F  |
| Cl    | Cl | H  | H  |
|       | H  | Cl | H  |
|       | H  | H  | Cl |
|       | Cl | Cl | H  |
|       | Cl | H  | Cl |
|       | H  | Cl | Cl |
|       | Cl | Cl | Cl |
| Br    | Br | H  | H  |
|       | H  | Br | H  |
|       | H  | H  | Br |
|       | Br | Br | H  |
|       | Br | H  | Br |
|       | H  | Br | Br |
|       | Br | Br | Br |
| F, Cl | F  | Cl | H  |
|       | Cl | F  | H  |
|       | F  | H  | Cl |
|       | Cl | H  | F  |
|       | H  | F  | Cl |
|       | H  | Cl | F  |
|       | Cl | F  | F  |
|       | F  | Cl | F  |
|       | F  | F  | Cl |
|       | Cl | Cl | F  |
|       | Cl | F  | Cl |
|       | F  | Cl | Cl |
| F, Br | F  | Br | H  |
|       | Br | F  | H  |
|       | F  | H  | Br |
|       | Br | H  | F  |
|       | H  | F  | Br |
|       | H  | Br | F  |
|       | Br | F  | F  |
|       | F  | Br | F  |
|       | F  | F  | Br |
|       | Br | Br | F  |
|       | Br | F  | Br |
|       | F  | Br | Br |
| Br, Cl| Br | Cl | H  |
|       | Cl | Br | H  |
|       | Br | H  | Cl |
|       | Cl | H  | Br |
|       | H  | Br | Cl |
|       | H  | Cl | Br |
|       | Cl | Br | Br |
|       | Br | Cl | Br |
|       | Br | Br | Cl |
|       | Cl | Cl | Br |
|       | Cl | Br | Cl |
|       | Br | Cl | Cl |

In an exemplary embodiment, according to any entries in this table, Y is as described herein, $R^2$ is $CF_3$ or $CHF_2$ or $CH_2F$, $R^{3a}$ is $CH_3$ and $R^{3b}$ is $CH_3$. In an exemplary embodiment, according to any entries in this table, Y is as described herein, $R^2$ is $CF_3$, $R^{3a}$ is unsubstituted alkyl and $R^{3b}$ is unsubstituted alkyl. In an exemplary embodiment, according to any entries in this table, Y is as described herein, $R^2$ is $CF_3$, $R^{3a}$ is ethyl and $R^{3b}$ is ethyl. In an exemplary embodiment, according to any entries in this table, Y is as described herein, $R^2$ is $CF_3$, $R^{3a}$ is $CH_3$ and $R^{3b}$ is $CH_3$. In an exemplary embodiment, according to any entries in this table, $R^2$, $R^{3a}$, and $R^{3b}$ are as described herein, and Y is H. In an exemplary embodiment, according to any entries in this table, $R^2$, $R^{3a}$, and $R^{3b}$ are as described herein, and Y is F. In an exemplary embodiment, according to any entries in this table, $R^2$, $R^{3a}$, and $R^{3b}$ are as described herein, and Y is Cl. In an exemplary embodiment, according to any entries in this table, $R^2$ is as described herein, $R^{3a}$ is $CH_3$ or $CH_2F$ and $R^{3b}$ is $CH_3$ or $CH_2F$, and Y is H. In an exemplary embodiment, according to any entries in this table, $R^2$ is as described herein, $R^{3a}$ is $CH_3$ or $CH_2F$ and $R^{3b}$ is $CH_3$ or $CH_2F$, and Y is F. In an exemplary embodiment, according to any entries in this table, $R^2$ is as described herein, $R^{3a}$ is $CH_3$ or $CH_2F$ and $R^{3b}$ is $CH_3$ or $CH_2F$, and Y is Cl. In an exemplary embodiment, according to any entries in this table, $R^2$ is $CF_3$, $R^{3a}$ is $CH_3$ or $CH_2F$ and $R^{3b}$ is $CH_3$ or $CH_2F$, and Y is H. In an exemplary embodiment, according to any entries in this table, $R^2$ is $CF_3$, $R^{3a}$ is $CH_3$ or $CH_2F$ and $R^{3b}$ is $CH_3$ or $CH_2F$, and Y is F. In an exemplary embodiment, according to any entries in this table, $R^2$ is $CF_3$, $R^{3a}$ is $CH_3$ or $CH_2F$ and $R^{3b}$ is $CH_3$ or $CH_2F$, and Y is Cl.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

As used herein, the term "chiral", "enantiomerically enriched" or "diastereomerically enriched" refers to a composition having an enantiomeric excess (ee) or a diastereomeric excess (de) of greater than about 50%, preferably greater than about 70% and more preferably greater than about 90%. In general, higher than about 90% enantiomeric or diastereomeric excess is particularly preferred, e.g., those compositions with greater than about 95%, greater than about 97% and greater than about 99% ee or de.

When a first compound and a second compound are present in a composition, and the first compound is a non-superimposable mirror image of the second compound, and the first compound is present in the composition in a greater amount than the second compound, then the first compound is referred to herein as being present in "enantiomeric excess".

The term "enantiomeric excess" of a compound z, as used herein, is defined as:

$$ee_z = \left(\frac{conc. \text{ of } z - conc. \text{ of } y}{conc. \text{ of } z + conc. \text{ of } y}\right) \times 100$$

wherein z is a first compound in a composition, y is a second compound in the composition, and the first compound is a non-superimposable mirror image of the second compound.

The term "enantiomeric excess" is related to the older term "optical purity" in that both are measures of the same phenomenon. The value of ee will be a number from 0 to 100, zero being racemic and 100 being enantiomerically pure. A composition which in the past might have been called 98% optically pure is now more precisely characterized by 96% ee. A 90% ee reflects the presence of 95% of one enantiomer and 5% of the other(s) in the material in question.

When a first compound and at least one additional compound are present in a composition, and the first compound and each of the additional compounds are stereoisomers, but not mirror images, of one another, and the first compound is present in the composition in a greater amount than each of the additional compounds, then the first compound is referred to herein as being present in "diastereomeric excess".

When dealing with mixtures of diastereomers, the term "diastereomeric excess" or "de" is defined analagously to enantiomeric excess. Thus:

$$de_w = \left(\frac{conc. \text{ of major diastereomer} - conc. \text{ of minor diastereomer(s)}}{conc. \text{ of major diastereomer} + conc. \text{ of minor diastereomer(s)}}\right) \times 100$$

wherein the major diastereomer is a first compound in a composition, and the minor diastereomer(s) is at least one additional compound in the composition, and the major diastereomer and minor diastereomer(s) are stereoisomers, but not mirror images, of one another.

The value of de will likewise be a number from 0 to 100, zero being an equal mixture of a first diastereomer and the remaining diastereomer(s), and 100 being 100% of a single diastereomer and zero % of the other(s)—i.e. diastereomerically pure. Thus, 90% de reflects the presence of 95% of one diastereomer and 5% of the other diastereomer(s) in the material in question.

Hence, in one embodiment, the invention provides a composition including a first compound of the invention, wherein the first compound of the invention has at least one stereocenter, and at least one stereoisomer of the first compound of the invention. In another embodiment, the invention provides a composition including a first compound of the invention, wherein the first compound of the invention has at least one stereocenter, and a second compound of the invention, wherein the first compound of the invention is a stereoisomer of the second compound of the invention. In another embodiment, the invention provides a composition including a first compound of the invention, wherein the first compound of the invention has at least one stereocenter, and only one stereoisomer of the first compound of the invention.

In another embodiment, the invention provides a composition including a first compound of the invention, wherein the first compound of the invention has only one stereocenter, and an enantiomer of the first compound of the invention. In another embodiment, the invention provides a composition including a first compound of the invention, wherein the first compound of the invention has two stereocenters, and an enantiomer of the first compound of the invention. In another embodiment, the invention provides a composition including a first compound of the invention, wherein the first compound of the invention has two stereocenters, and at least one diasteromer of the first compound of the invention. In another embodiment, the invention provides a composition including a first compound of the invention, wherein the first compound of the invention has two stereocenters, and only one diasteromer of the first compound of the invention.

In situations where the first compound of the invention and its enantiomer are present in a composition, the first compound of the invention can be present in an enantiomeric excess of at least about 80%, or at least about 90%, or at least about 92% or at least about 95%. In another embodiment, where the first compound of the invention and its enantiomer are present in a composition, the first compound of the invention can be present in an enantiomeric excess of at least about 96%, at least about 97%, at least about 98%, at least about 99% or at least about 99.5%. In another embodiment, the first compound of the invention has at least one stereocenter and is enantiomerically pure (enantiomeric excess is about 100%).

In situations where the first compound of the invention and at least one diastereomer of the first compound of the invention are present in a composition, the first compound of the invention can be present in a diastereomeric excess of at least about 80%, or at least about 90%, or at least about 92% or at least about 95%. In situations where the first compound of the invention and at least one diastereomer of the first compound of the invention are present in a composition, the first compound of the invention can be present in a diastereomeric excess of at least about 96%, at least about 97%, at least about 98%, at least about 99% or at least about 99.5%. In another embodiment, the first compound of the invention has at least two stereocenters and is diastereomerically pure (diastereomeric excess is about 100%).

Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

As used herein, and unless otherwise indicated, a composition that is "substantially free" of a compound means that the composition contains less than about 20% by weight, or less than about 15% by weight, or less than about 10% by weight, or less than about 5% by weight, or less than about 3% by weight, or less than about 2% by weight, or less than about 1% by weight of the compound.

As used herein, the term "substantially free of the (or its) enantiomer" means that a composition contains a significantly greater proportion of a first compound of the invention than a second compound of the invention, wherein the first compound is a non-superimposable mirror image of the second compound. In one embodiment of the invention, the term "substantially free of the enantiomer" means that the composition is made up of at least about 90% by weight of a first compound of the invention, and about 10% by weight or less of a second compound of the invention, wherein the first compound is a non-superimposable mirror image of the second compound. In one embodiment of the invention, the term "substantially free of the (R) enantiomer" means that the composition is made up of at least about 90% by weight of a first compound of the invention which has only one stereocenter and the stereocenter is in an (S) configuration, and about 10% by weight or less of a second compound of the invention, wherein the second compound is the enantiomer of the first compound. In one embodiment of the invention, the term "substantially free of the enantiomer" means that the composition is made up of at least about 95% by weight of a first compound of the invention, and about 5% by weight or less of a second compound of the invention, wherein the first compound is a non-superimposable mirror image of the second compound. In one embodiment of the invention, the term "substantially free of the (R) enantiomer" means that the composition is made up of at least about 95% by weight of a first compound of the invention which has only one stereocenter and the stereocenter is in an (S) configuration, and about 5% by weight or less of a second compound of the invention, wherein the second compound is the enantiomer of the first compound. In one embodiment of the invention, the term "substantially free of the enantiomer" means that the composition is made up of at least about 98% by weight of a first compound of the invention, and about 2% by weight or less of a second compound of the invention, wherein the first compound is a non-superimposable mirror image of the second compound. In one embodiment of the invention, the term "substantially free of the (R) enantiomer" means that the composition is made up of at least about 98% by weight of a first compound of the invention which has only one stereocenter and the stereocenter is in an (S) configuration, and about 2% by weight or less of a second compound of the invention, wherein the second compound is the enantiomer of the first compound. In one embodiment of the invention, the term "substantially free of the enantiomer" means that the composition is made up of at least about 99% by weight of a first compound of the invention, and about 1% by weight or less of a second compound of the invention, wherein the first compound is a non-superimposable mirror image of the second compound. In one embodiment of the invention, the term "substantially free of the (R) enantiomer" means that the composition is made up of at least about 99% by weight of a first compound of the invention which has only one stereocenter and the stereocenter is in an (S) configuration, and about 1% by weight or less of a second compound of the invention, wherein the second compound is the enantiomer of the first compound.

In an exemplary embodiment, the invention provides a composition comprising a) first compound described herein; and b) the enantiomer of the first compound, wherein the first compound described herein is present in an enantiomeric excess of at least 80%. In an exemplary embodiment, the enantiomeric excess is at least 92%. In another exemplary embodiment, the first compound described herein has an isoxazolinyl moiety, and one carbon atom in the isoxazolinyl moiety is a stereocenter, and the stereocenter is in a (S) configuration, and the stereocenter is the only stereocenter in the first compound. In another exemplary embodiment, the first compound described herein has an isoxazolinyl moiety, and one carbon atom in the isoxazolinyl moiety is a stereocenter, and the stereocenter is in a (R) configuration, and the stereocenter is the only stereocenter in the first compound.

In an exemplary embodiment, the invention provides a composition comprising a first compound described herein with an isoxazolinyl moiety, and one carbon atom in the isoxazolinyl moiety is a stereocenter, and the stereocenter is in a (S) configuration, and said composition is substantially free of the enantiomer of the first compound described herein. In an exemplary embodiment, the invention provides a composition comprising a first compound described herein with an isoxazolinyl moiety, and one carbon atom in the isoxazolinyl moiety is a stereocenter, and the stereocenter is in a (R) configuration, and said composition is substantially free of the enantiomer of the first compound described herein.

The compounds of the invention may also be used in combination with additional therapeutic agents. The invention thus provides, in a further aspect, a combination comprising a compound described herein or a pharmaceutically acceptable salt thereof together with at least one additional therapeutic agent. The invention thus provides, in a further aspect, a combination comprising a compound described herein or a pharmaceutically acceptable salt thereof together with one additional therapeutic agent. The invention thus provides, in a further aspect, a combination comprising a compound described herein or a pharmaceutically acceptable salt thereof together with two additional therapeutic agents. The invention thus provides, in a further aspect, a combination comprising a compound described herein or a pharmaceutically acceptable salt thereof together with a first additional therapeutic agent and a second additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom.

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. In an exemplary embodiment, the additional therapeutic agent is an acaricide. In an exemplary embodiment, the additional therapeutic agent is an ixodicide. In an exemplary embodiment, the additional therapeutic agent is a miticide. In an exemplary embodiment, the additional therapeutic agent is pyrethrine. In an exemplary embodiment, the additional therapeutic agent is permethin or pyrethrum or phenothrin. In an exemplary embodiment, the additional therapeutic agent is a chloride channel inhibitor. In an exemplary embodiment, the additional therapeutic agent is an avermectin. In an exemplary embodiment, the additional therapeutic agent is selamectin or doramectin or abamectin. In an exemplary embodiment, the additional therapeutic agent is ivermectin. In an exemplary embodiment, the additional therapeutic agent is a milbemycin. In an exemplary embodiment, the additional therapeutic agent is milbemectin or moxidectin or nemadectin. In an exemplary embodiment, the additional therapeutic agent is milbemycin oxime. In an exemplary embodiment, a first additional therapeutic agent is milbemycin oxime and a second additional therapeutic agent is a spinosad. In an exemplary embodiment, the additional therapeutic agent is an organophosphate. In an exemplary embodiment, the additional therapeutic agent is malathion. In an exemplary embodiment, the additional therapeutic agent is lindane. In an exemplary embodiment, the additional therapeutic agent is disulfuram. In an exemplary embodiment, the additional therapeutic agent is benzyl benzoate. In an exemplary embodiment, the additional therapeutic agent is fipronil. In an exemplary embodiment, the additional therapeutic agent comprises an isoxazoline moiety. In an exemplary embodiment, the additional therapeutic agent is Nissan A1443.

In an exemplary embodiment, the additional therapeutic agent is a spinosad. In an exemplary embodiment, the additional therapeutic agent is a spinosad or a salt, (e.g. pharmaceutically acceptable salt), prodrug, solvate or hydrate thereof. Spinosad is a member of the spinosyns class of insecticides, which are non-antibacterial tetracyclic macrolides. Spinosad contains two major factors, spinosyn A and spinosyn D. Spinosyn A and spinosyn D are known as 2-[(6-deoxy-2,3,4-tri-O-methyl-α-L-mannopyranosyl)oxy]-13-[[5-dimethylamino)-tetrahydro-6-methyl-2H-pyran-2-yl]oxy]-9-ethyl-2,3,3a,5a,5b,6,9,10,11,12,13,14,16a,16b-tetradecahydro-14-methyl-1H-as-Indaceno[3,2-d]oxacyclododecin-7, 15-dione and 2-[(6-deoxy-2,3,4-tri-O-methyl-α-L-mannopyranosyl)oxy]-13-[[5-dimethylamino)-tetrahydro-6-methyl-2H-pyran-2-yl]oxy]-9-ethyl-2,3,3a,5a,5b,6,9,10,11,12,13,14,16a,16btetradecahydro-4,14-dimethyl-1H-as-Indaceno[3,2-d]oxacyclododecin-7,15-dione, respectively. Spinosyn A and spinosyn D have a structure according to the following formula:

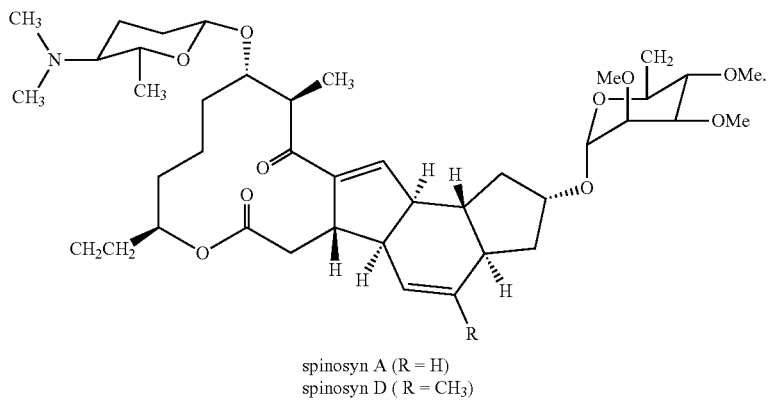

spinosyn A (R = H)
spinosyn D ( R = CH₃)

In an exemplary embodiment, the additional therapeutic agent is spinetoram. In an exemplary embodiment, the additional therapeutic agent is spinosyn A. In an exemplary embodiment, the additional therapeutic agent is spinosyn A or a salt, (e.g. pharmaceutically acceptable salt), prodrug, solvate or hydrate thereof. In an exemplary embodiment, the additional therapeutic agent is spinosyn D. In an exemplary embodiment, the additional therapeutic agent is spinosyn D or a salt, (e.g. pharmaceutically acceptable salt), prodrug, solvate or hydrate thereof. In exemplary embodiments, Comfortis® is administered in combination with a compound described herein, optionally with a pharmaceutically acceptable excipient. In exemplary embodiments, any pharmaceutical formulation comprising a spinosad (e.g., a pharmaceutical formulation comprising (a) a pharmaceutically acceptable excipient; (b) a compound of the invention and (c) a spinosad (e.g., spinosyn A or spinosyn D) is administered orally. In exemplary embodiments, any pharmaceutical formulation comprising a spinosad is administered to kill or inhibit the growth of fleas. In exemplary embodiments, any pharmaceutical formulation comprising a spinosad is administered to kill or inhibit the growth of ticks.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may be presented for use as a pharmaceutical formulation. Thus, an exemplary embodiment of the invention is a pharmaceutical formulation comprising a) a compound of the invention; b) an additional therapeutic agent and c) a pharmaceutically acceptable excipient. Thus, an exemplary embodiment of the invention is a pharmaceutical formulation comprising a) a compound of the invention; b) a first additional therapeutic agent; c) a second additional therapeutic agent and d) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

In one aspect, the invention is a combination comprising: a) a compound of the invention; and b) at least one additional therapeutic agent. In an exemplary embodiment, the invention is a combination comprising: a) a compound of the invention; and b) an additional therapeutic agent. In another exemplary embodiment, the combination comprises: a) a compound of the invention; b) a first additional therapeutic agent; and c) a second additional therapeutic agent. In another exemplary embodiment, the combination comprises: a) a compound of the invention; b) a first additional therapeutic agent; c) a second additional therapeutic agent; and d) a third additional therapeutic agent. The first additional therapeutic agent or second additional therapeutic agent or third additional therapeutic agent can be selected from the additional therapeutic agents described in this document.

It is to be understood that the invention covers all combinations of aspects and/or embodiments, as well as suitable, convenient and preferred groups described herein.

Compounds of use in the invention can be prepared using commercially available starting materials, known intermediates, or by using the synthetic methods described herein, or published in references described and incorporated by reference herein, such as PCT Pub. No. WO2008157726 and U.S. Pat. Pubs. US20060234981, US20070155699 and US20070293457.

In one embodiment, the compound of the invention can be synthesized according to the following scheme:

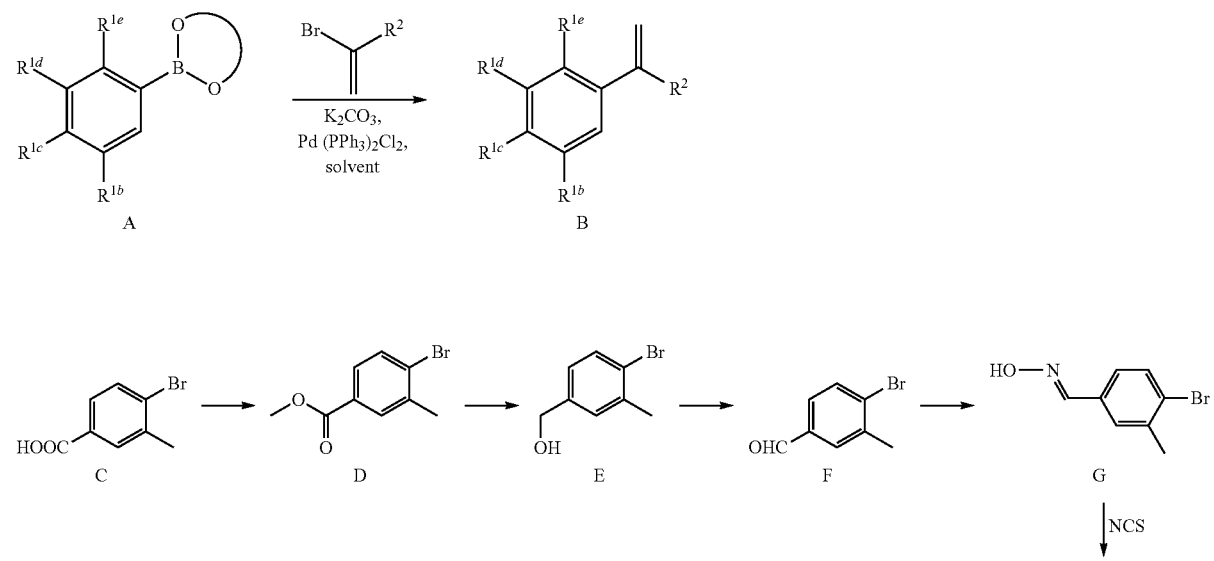

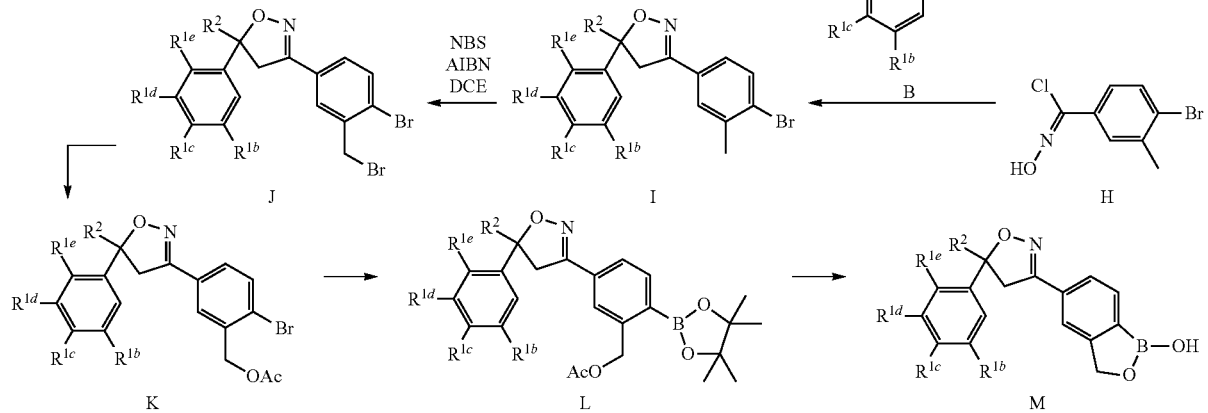

(where $R^{1e}$ can be hydrogen, $R^{1b}$, $R^{1c}$, or $R^{1d}$), wherein boronic acid-related A is commercially available from, for example, Sigma-Aldrich. A can also be synthesized from the corresponding aryl bromide using well known conventional methods available in the literature. A can be converted to B through Suzuki coupling reaction. C can be converted to D through subjecting it to esterification reaction conditions, such as those involving thionyl chloride and alcohol. D can be converted to E through subjecting it to reducing conditions, such as those involving $LiAlH_4$. E can be converted to F through subjecting it to oxidation conditions, such as those involving $MnO_2$. F can be converted to G through subjecting it to oxime-forming reaction conditions, such as those involving hydroxylamine G can be converted to H through subjecting it to chlorination reaction conditions, such as those involving NCS. H can be converted to I through subjecting it to cyclization reaction with B. I can be converted to J through subjecting it to bromination reaction conditions, such as those involving NBS. J can be converted to K through subjecting it to substitution conditions, such as that involving sodium acetate. K can be converted to L through subjecting it to boronylation reaction conditions, such as those involving bis(pinacolato)diboron. L can be converted to M through subjecting it to hydrolysis conditions, such as those involving aqueous lithium hydroxide and then aqueous hydrochloric acid.

In one embodiment, the compound of the invention can be synthesized according to the following scheme:

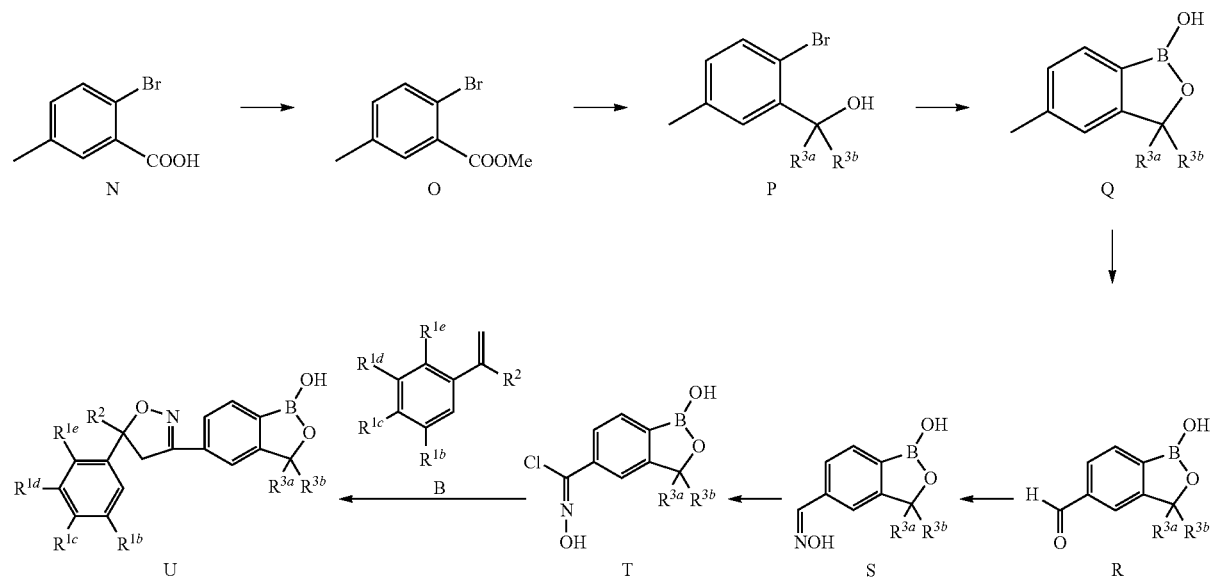

wherein N is commercially available from, for example, Sigma-Aldrich. N can be converted to O through subjecting it to esterification reaction conditions, such as those involving thionyl chloride and alcohol. O can be converted to P through subjecting it to Grignard reaction conditions, such as that involving alkyl magnesium bromide ($R^{3a}$ and $R^{3b}$ are same in this scheme). P can be converted to Q through subjecting it to boronylation conditions. Q can be converted to R through subjecting it to dibromination and hydrolysis conditions, such as those involving 2 eq NBS and then aqueous sodium carbonate. R can be converted to S through subjecting it to oxime-forming conditions, such as those involving hydroxylamine S can be converted to T through subjecting it to chlorination conditions, such as that involving NCS. T can be converted to U through subjecting it to cyclization reaction with B.

In one embodiment, the compound of the invention can be synthesized according to the following scheme:

In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In

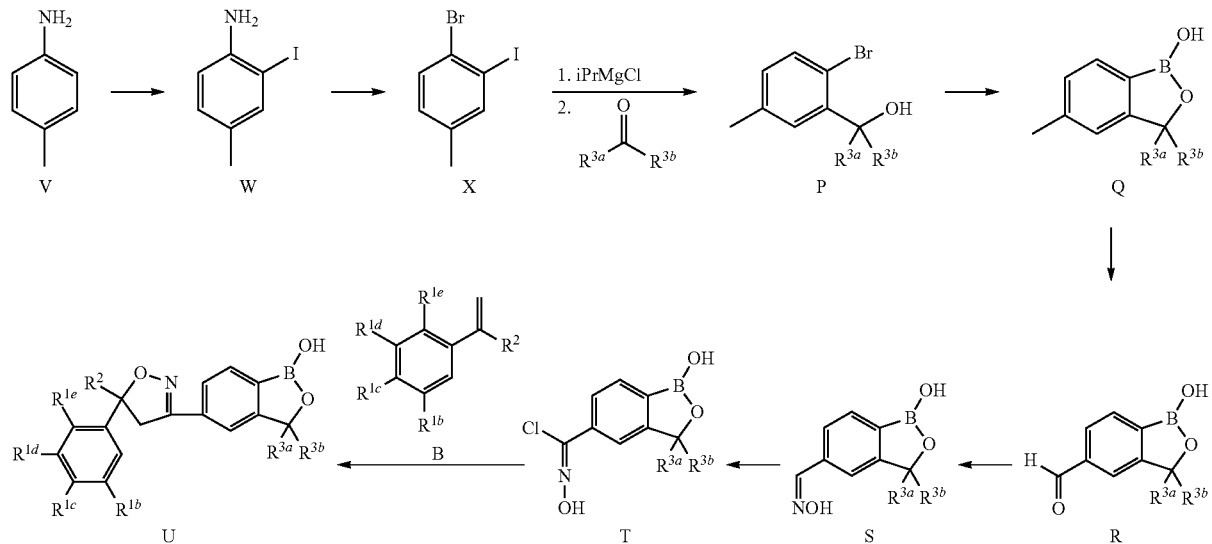

wherein V is commercially available from, for example, Sigma-Aldrich. V can be converted to W through subjecting it to iodination reaction conditions, such as those involving $I_2$. W can be converted to X through subjecting it to Sandmeyer reaction conditions, such as those involving $HNO_2$ and then CuBr. X can be converted to P through subjecting it to Grignard-reagent-forming condition and then addition reaction to ketones ($R^{3a}$ and $R^{3b}$ can be same or different in this scheme). The rest of the reaction conditions in this scheme are same as described in the previous scheme.

Compounds described herein can be converted into hydrates and solvates by methods similar to those described herein.

The compounds of the invention exhibit potency against ectoparasites and therefore have the potential to kill and/or inhibit the growth of ectoparasites. The compounds of the invention exhibit potency against insects and thus have the potential to kill and/or inhibit the growth of insects.

In a further aspect, the invention provides a method of killing and/or inhibiting the growth of an ectoparasite, said method comprising: contacting said ectoparasite with an effective amount of a compound of the invention, thereby killing and/or inhibiting the growth of the ectoparasite. In an exemplary embodiment, the ectoparasite is an acari. In an exemplary embodiment, the ectoparasite is a tick. In an exemplary embodiment, the ectoparasite is a mite. In an exemplary embodiment, the compound is described herein, or a salt, prodrug, hydrate or solvate thereof, or a combination thereof. In an exemplary embodiment, the invention provides a compound described herein, or a salt, hydrate or solvate thereof.

another exemplary embodiment, the contacting occurs under conditions which permit entry of the compound into the organism.

In another aspect, the ectoparasite is on the surface of an animal. In another aspect, the ectoparasite is in an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In an exemplary embodiment, the animal is a warm-blooded animal.

In another aspect, the ectoparasite is on the surface of a plant. In another aspect, the ectoparasite is in a plant.

In an exemplary embodiment, the ectoparasite is killed or its growth is inhibited through oral administration of the compound of the invention. In an exemplary embodiment, the ectoparasite is killed or its growth is inhibited through intravenous administration of the compound of the invention. In an exemplary embodiment, the ectoparasite is killed or its growth is inhibited through subcutaneous administration of the compound of the invention.

In an exemplary embodiment, the ectoparasite is an insect. In an exemplary embodiment, the insect is selected from the group consisting of Lepidoptera, Coleoptera, Homoptera, Hemiptera, Heteroptera, Diptera, Dictyoptera, Thysanoptera, Orthoptera, Anoplura, Siphonaptera, Mallophaga, Thysanura, lsoptera, Psocoptera and Hymenoptera. However, the ectoparasites which may be mentioned in particular are those which trouble humans or animals and carry pathogens, for example flies such as *Musca domestica, Musca vetustissima,*

*Musca autumnalis, Fannie canicularis, Sarcophage carnaria, Lucilia cuprina, Lucilia sericata, Hypoderma bovis, Hypoderma lineatum, Chrysomyia chloropyga, Dermatobie hominis, Cochliomyia hominivorax, Gasterophilus intestinaiis, Oestrus ovis*, biting flies such as *Haematobia irritans irritans, Haematobia irritans exigua, Stomoxys calcitrans*, horse-flies (*Tabanids*) with the sublarnilies of Tabanidae such as *Haematopota* spp. (e.g. *Haematopota pluvialis*) and *Tabanus* spp, e.g. *Tabanus nigrovittatus*) and Chrysopsinee such as *Chrysops* spp. (e.g. *Chrysops caecutlens*); Hippoboscids such as *Melophagus ovinus* (sheep ked); tsetse flies, such as *Glossinia* sop; other biting insects like midges, such as Ceratopogonidae (biting midges), Simuliidse (Blackflies), Psychodidae (Sandflies); but also blood-sucking insects, for example mosquitoes, such as *Anopheles spp, Aedes sop* and *Culex* spp, fleas, such as *Ctenocephalides felis* and *Ctenocephalides canis* (cat and dog fleas, respectively), *Xenopsylla cheopis, Pulex irritans, Ceratophyilus galfinae, Dermatophilus penetrans*, blood-sucking lice (Anoplura) such as *Linognathus* spp, *Haematopinus* spp, *Olenopotes* spp, *Pediculus humanis*; but also chewing lice (Mallophaga) such as *Bovicola* (*Damalinia*) *ovis, Bovicola* (*Darnalinia*) *bovis* and other *Bovicola* spp. Ectoparasites also include members of the order Acarina, such as mites (e.g. *Chorioptes bovis, Cheyletiella* spp., *Dermanyasus galiinae, Ortnithonyssus* spp., *Demodex cants, Sarcoptes scabiei, Psoroptes ovis* and *Psorergates* spp. In an exemplary embodiment, the insect is a tick or flea.

In an exemplary embodiment, the ectoparasite is a fly. In an exemplary embodiment, the ectoparasite is a member of the Oestridae family. In an exemplary embodiment, the ectoparasite is a bot. In an exemplary embodiment, the ectoparasite is a horse bot. In an exemplary embodiment, the insect is a member of the *Gasterophilus* genus. In an exemplary embodiment, the insect is *Gasterophilus nasalis* or *Gasterophilus intestinalis* or *Gasterophilus haemorrhoidalis* or *Gasterophilus inermis* or *Gasterophilus nigricomis* or *Gasterophilus pecorum*. In an exemplary embodiment, the insect is *Gasterophilus nasalis* or *Gasterophilus intestinalis* or *Gasterophilus haemorrhoidalis*.

In an exemplary embodiment, the tick is a hard tick. In an exemplary embodiment, the tick is a soft tick. In an exemplary embodiment, the tick is a Nuttalliellidae tick. In an exemplary embodiment, the tick is an Argasidae tick. In an exemplary embodiment, the tick is an *Antricola* tick or *Argas* tick or *Nothaspis* tick or *Ornithodoros* tick or *Otobius* tick. In an exemplary embodiment, the tick is an Ixodidae tick. In an exemplary embodiment, the tick is an *Amblyomma* tick. In an exemplary embodiment, the tick is a *Dermacentor* tick. In an exemplary embodiment, the tick is a *Rhipicephalus* tick. In an exemplary embodiment, the tick is a *Rhipicephalus* tick. In an exemplary embodiment, the tick is an *Anomalohimalaya* tick or *Bothriocroton* tick or *Cosmiomma* tick or *Cornupalpatum* tick or *Compluriscutula* tick or *Haemaphysalis* tick or *Hyalomma* tick or *Ixodes* tick or *Margaropus* tick or *Nosomma* tick or *Rhipicentor* tick. In an exemplary embodiment, the tick is an *Ornithodorus* tick. In an exemplary embodiment, the ectoparasite is a *Boophilus* tick or an *Anocentor* tick. In an exemplary embodiment, the ectoparasite is a tick which is selected from the group consisting of *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata*.

In an exemplary embodiment, the ectoparasite is a mite which is selected from the group consisting of Parasitiformes and Mesostigmata. In an exemplary embodiment, the ectoparasite is a mite which is *Ornithonyssus bacoti* or *Dermanyssus gallinae*.

In an exemplary embodiment, the ectoparasite is a mite. In an exemplary embodiment, the mite is Arcarina or Tetranychidae. In an exemplary embodiment, the mite is *Tetranychus* spp. or *Panonychus* spp. In an exemplary embodiment, the mite is a trombiculid mite. In an exemplary embodiment, the mite is chigger.

In an exemplary embodiment, the ectoparasite is a flea. In an exemplary embodiment, the flea (Siphonaptera) is a *Ctenocephalides* flea or *Xenopsylla* flea or *Pulex* flea or *Tunga* flea or *Dasypsyllus* flea or *Nosopsyllus* flea. In an exemplary embodiment, the flea (Siphonaptera) is *Ctenocephalides felis* or *Ctenocephalides canis* or *Xenopsylla cheopis* or *Pulex irritan* or *Tunga penetrans* or *Dasypsyllus gallinulae* or *Nosopsyllus fasciatus*.

The compounds described herein according to the invention are also active against all or individual development stages of animal pests showing normal sensitivity, as well as those showing resistance to widely used parasiticides. This is especially true for resistant insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate.

The compounds described herein can also be used against hygiene pests, especially of the order Diptera of the families Muscidae, Saroophagidae, Anophilidae and Cuticidae; the orders Orthoptera, Dictyoptera (e.g. the family Blattidae (cockroaches), such as *Blatella germanica, Blatta onentalis, Periplaneta americana*) and Hymenoptera (e.g. the families Formicidae (ants) and Vespidae (wasps)).

They have high activity against sucking insects of the order Hornoptera, especially against pests of the families Aphididee, Delphacidae, Cicadellidea Psyllidae, Diaspididae and Eriophydidae (e.g. rust mite on citrus fruits); the orders Hemiptera, Hetsroptera and Thysenoptera, and on the plant-eating insects of the orders Lepidoptera, Coleoptera, Diptera and Orthoptera. In an exemplary embodiment, the insect is Cimicidae. In an exemplary embodiment, the insect is *Cimex lectularius*. In an exemplary embodiment, the insect is a bed bug.

In an exemplary embodiment, the ectoparasite is lice. In an exemplary embodiment, the lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.

In an exemplary embodiment, the ectoparasite is an ectoparasite of fishes. In an exemplary embodiment, the ectoparasite is Copepoda (e.g. order of Siphonostomatoidae) (sea lice).

Diseases transmitted through ectoparasites, particularly blood-feeding ectoparasites such as ticks, biting and muscoid flies, reduvid bugs, mosquitos, mites, and fleas, include, for example, bacterial, viral and protozoal diseases. Non-vector born pathological conditions associated with ectoparasite infestations include, for example, flea-allergy dermatitis (FAD) associated with flea infestations; secondary dematological infections associated with heavy ectoparasite burden (i.e., face-fly infestations in cattle herds and ear-mite induced otitis externa in dogs), and tick paralysis associated with various tick species. Mites are implicated in scabies and rosacea. The compounds of the invention are effective in the treatment and control of ectoparasites implicated or suspected in development of diseases in animals, such as mammals and birds, and therefore have the potential to indirectly ameliorate, reduce or prevent such diseases associated with ectoparasite infestations in the animals described herein. The compounds of the invention are effective in the treatment and control of ectoparasites implicated or suspected in development of diseases in plants, and therefore have the potential to indirectly ameliorate, reduce or prevent such diseases associated with ectoparasite infestations in the plants described herein.

In one embodiment, arbovirus (arthropod-borne virus) diseases associated with an ectoparasite include, for example, Crimean-Congo Hemmorhagic Fever (CCHF), Febrile illness, Papataci fever, Encephalitis and Meningitis, which are caused by Bunyaviridae such as Bunyavirus, Nairovirus and Phlebovirus; Bluetongue, meningoencephalits, Febrile illness, hemorrhagic fever, which are caused by Reoviridae such as Orbivirus and Colitivirus; Febrile illness, rash, encephalitis, polyarthritis, lymphadenitis which are caused by Togaviridae, such as Sindbisvirus and Chikungunya Virus; tick-borne meningoencephalitis, Dengue hemmorhagic fever, encephalitis, Febrile illness or West Nile Fever, and Yellow fever which are caused by Flaviviridae, such as Flavivirus (including diverse sub-groups); West Nile virus. In another embodiment, bacterial diseases transmitted by ectoparasites include, for example, Rocky Mountain spotted fever, tick typhus caused by infection through *Rickettsia* spp; Q-fever caused by *Coxiella burnetii*; Tularemia caused by infection through *Francisella tularensis*; Borreliosis or Spirochaetosis, such as Lyme disease, or relapsing fever, caused by infection through *Borrelia* spp.; Ehrlichiosis caused by infection through *Ehrlichia* spp.; Plague, caused by infection through *Yersinia pestis*. In another embodiment, protozoan or rickettsial diseases transmitted by ectoparasites include, for example, Babesiosis, such as Texas fever, red water disease, caused by infection through *Babesia* spp.; Theileriosis, such as east coast fever, Mediterranean coast fever, caused by infection through *Theileria* spp.; Nagana disease, Sleeping sickness caused by infection through *Trypanosoma* spp., *Anaplasmosis caused* by infection through *Anaplasma* spp.; Malaria caused by infection through *Plasmodium* spp.; Leishmaniasis caused by infection through *Leishmania* spp.

In an exemplary embodiment, the invention provides a method of reducing the size of an ectoparasitic infestation in or on an animal in need of treatment thereof. The method includes administering to the animal a therapeutically effective amount of the compound of the invention, sufficient to reduce the size of the ectoparasitic infestation. In an exemplary embodiment, the invention provides a method of reducing the size of an ectoparasitic infestation in or on a plant in need of treatment thereof. The method includes administering to the plant a therapeutically effective amount of the compound of the invention, sufficient to reduce the size of the ectoparasitic infestation.

In an exemplary embodiment, the invention provides a method of controlling an ectoparasitic infestation in or on an animal in need of treatment thereof. The method includes administering to the animal a therapeutically effective amount of the compound of the invention, sufficient to control the ectoparasitic infestation. In an exemplary embodiment, controlling an ectoparasitic infestation is reducing the number of ectoparasites in or on an animal. In an exemplary embodiment, the invention provides a method of controlling an ectoparasitic infestation in or on a plant in need of treatment thereof. The method includes administering to the plant a therapeutically effective amount of the compound of the invention, sufficient to control the ectoparasitic infestation. In an exemplary embodiment, controlling an ectoparasitic infestation is reducing the number of ectoparasites in or on a plant.

In an exemplary embodiment, the invention provides a method of preventing an ectoparasitic infestation in or on an animal in need of treatment thereof. The method includes administering to the animal a prophylactically effective amount of the compound of the invention, sufficient to prevent the ectoparasitic infestation. In an exemplary embodiment, the invention provides a method of preventing an ectoparasitic infestation in or on a plant in need of treatment thereof. The method includes administering to the plant a prophylactically effective amount of the compound of the invention, sufficient to prevent the ectoparasitic infestation.

In an exemplary embodiment, the invention provides a method of reducing the transmission, in an animal, of a disease transmitted through an ectoparasite. The method includes administering to the animal in need thereof a therapeutically effective amount of the compound of the invention, sufficient to reduce the spread of the disease-causing agent from the ectoparasite to the animal. In an exemplary embodiment, the invention provides a method of reducing the transmission, in a plant, of a disease transmitted through an ectoparasite. The method includes administering to the plant in need thereof a therapeutically effective amount of the compound of the invention, sufficient to reduce the spread of the disease-causing agent from the ectoparasite to the plant.

In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. Such conditions are known to one skilled in the art and specific conditions are set forth in the Examples appended hereto.

In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. Such conditions are known to one skilled in the art and specific conditions are set forth in the Examples appended hereto.

In another exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a non-human mammal. In another exemplary embodiment, the animal is a mammal. In another exemplary embodiment, the animal is a domestic animal. In another exemplary embodiment, the animal is a domestic mammal. In another exemplary embodiment, the animal is a companion animal. In another exemplary embodiment, the animal is a companion mammal. In another exemplary embodiment, the animal is a dog. In another exemplary embodiment, the animal is a cat. In another exemplary embodiment, the animal is a rodent. In another exemplary embodiment, the animal is a rat. In another exemplary embodiment, the animal is a mouse. In another exemplary embodiment, the animal is a member selected from goat, pig, sheep, horse, cow, bull, dog, guinea pig, gerbil, rabbit, cat, chicken and turkey. In another exemplary embodiment, the animal is an ungulate. In another exemplary embodiment, the ungulate is selected from the group consisting of horse, zebra, donkey, cattle/bison, rhinoceros, camel, hippopotamus, goat, pig, sheep, giraffe, okapi, moose, elk, deer, tapir, antelope, and gazelle. In another exemplary embodiment, the ungulate is cattle. In another exemplary embodiment, the ungulate is selected from the group consisting of goat, pig, and sheep. In another exemplary embodiment, the animal is a ruminant. In another exemplary embodiment, the ruminant is selected from the group consisting of cattle, goats, sheep, giraffes, bison, yaks, water buffalo, deer, camels, alpacas, llamas, wildebeast, antelope, pronghorn, and nilgai. In another exemplary embodiment, the cattle is a cow. In another exemplary embodiment, the cattle is a bull. In another exemplary embodiment, the cattle is a calf. In another exemplary embodiment, the animal is an equine. In another exemplary embodiment, the animal is selected from the group consisting of horse, donkey, caribou and reindeer. In another exemplary embodiment, the animal is a horse. In another exemplary embodiment, the animal is a snail. In another exemplary embodiment, the animal is an insect. In another exemplary embodiment, the animal is a mosquito. In another exemplary embodiment, the animal is a fly.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the disease is treated through subcutaneous injection of the compound of the invention. In an exemplary embodiment, the compound is administered in a topically effective amount. In an exemplary embodiment, the pharmaceutical formulation is administered in an orally effective amount. In an exemplary embodiment, the compound is administered in an effective amount via subcutaneous injection.

Given their activity, the compounds of the invention are suitable as soil insecticides against pests in the soil, as well as insecticides for plants, such as cereals, cotton, rice, maize, soya, potatoes, vegetables, fruit, tobacco, hops, citrus, and avocados. The compounds according to the invention are suitable for protecting plants and plant organs, for increasing the harvest yields, and for improving the quality of the harvested material which are encountered in agriculture, in horticulture, in forests, in gardens, and leisure facilities, and in the protection of stored products and of materials. They may be employed as plant protection agents. Therefore, the compounds of the invention can be used to treat a disease in a plant, or kill or inhibit the growth of a worm that affects a plant.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out by conventional and known means, including directly acting on, or by allowing the compounds to act on, the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In an exemplary embodiment, the pharmaceutically acceptable excipient is a pharmaceutically acceptable carrier. In an exemplary embodiment, the pharmaceutically acceptable excipient is a pharmaceutically acceptable diluent. In an exemplary embodiment, the pharmaceutically acceptable excipient is a pharmaceutically acceptable vehicle. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form. In an exemplary embodiment, a pharmaceutical formulation described herein can be administered to an animal described herein. In an exemplary embodiment, a pharmaceutical formulation described herein can be administered to a human. In an exemplary embodiment, a pharmaceutical formulation described herein is administered to a non-human mammal described herein. In an exemplary embodiment, a pharmaceutical formulations described herein can be administered to a plant described herein.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, chewable tablet, capsule, elixir, syrup, spray, lozenge, troche, or the like is particularly preferred. The term parenteral as used herein includes subcutaneous injections, intradermal, intravascular (e.g., intravenous), intramuscular, spinal, intrathecal injection or like injection or infusion techniques. Topical administration as used herein includes application of liquid and/or solid and/or semi-solid formulations as dermal spot-ons, sprays, dips, pour-ons, dusts or powders, ointments, and feed-throughs. In an exemplary embodiment, the pharmaceutical formulation is administered orally. In an exemplary embodiment, the pharmaceutical formulation is administered intravenously. In an exemplary embodiment, the pharmaceutical formulation is administered in a topically effective dose. In an exemplary embodiment, the pharmaceutical formulation is administered in an orally effective dose.

The pharmaceutical formulations containing compounds of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with pharmaceutically acceptable excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional pharmaceutically acceptable excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating pharmaceutically acceptable excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 0.01 mg to about 3500 mg per kilogram of body weight per day, about 0.01 mg to about 1000 mg per kilogram of body weight per day, or from about 0.1 mg to about 100 mg per kilogram of body weight per day, or from about 5 mg to about 250 mg per kilogram of body weight per day, or from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 3500 mg of an active ingredient. In an exemplary embodiment, an effective amount can be selected from a dosage range provided in this document. In an exemplary embodiment, a therapeutically effective amount can be selected from a dosage range provided in this document. In an exemplary embodiment, a prophylatically effective amount can be selected from a dosage range provided in this document. In an exemplary embodiment, an orally effective amount can be selected from a dosage range provided in this document. In an exemplary embodiment, a topically effective amount can be selected from a dosage range provided in this document.

Frequency of dosage may also vary depending on the compound used and the particular disease treated. In an exemplary embodiment, the composition of the invention is administered once a day or twice a day or three times a day or four times a day. In an exemplary embodiment, the composition of the invention is administered once a week or twice a week or three times a week or four times a week. In an exemplary embodiment, the composition of the invention is administered once a month or twice a month or three times a month or four times a month. It will be understood, however, that the specific dose level for any particular animal or plant will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention. In an exemplary embodiment, the unit dosage form contains from about 800 mg to about 3500 mg of a compound of the invention. In an exemplary embodiment, the unit dosage form contains from about 800 mg to about 3000 mg of a compound of the invention. In an exemplary embodiment, the unit dosage form contains from about 2000 mg to about 3000 mg of a compound of the invention. In an exemplary embodiment, the unit dosage form contains from about 950 mg to about 1450 mg of a compound of the invention. In an exemplary embodiment, the unit dosage form contains from about 1450 mg to about 1950 mg of a compound of the invention. In an exemplary embodiment, the unit dosage form contains from about 1950 mg to about 2450 mg of a compound of the invention. In an exemplary embodiment, the unit dosage form contains from about 2450 mg to about 2950 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention. In an exemplary embodiment, the daily dosage contains from about 800 mg to about 3500 mg of a compound of the invention. In an exemplary embodiment, the daily dosage contains from about 800 mg to about 3000 mg of a compound of the invention. In an exemplary embodiment, the daily dosage contains from about 2000 mg to about 3000 mg of a compound of the invention. In an exemplary embodiment, the daily dosage contains from about 950 mg to about 1450 mg of a compound of the invention. In an exemplary embodiment, the daily dosage contains from about 1450 mg to about 1950 mg of a compound of the invention. In an exemplary embodiment, the daily dosage contains from about 1950 mg to about 2450 mg of a compound of the invention. In an exemplary embodiment, the daily dosage contains from about 2450 mg to about 2950 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the animal or plant and will ultimately be at the discretion of the attendant physician or veterinarian or agronomist.

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, J. Chromat. B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in animals (such as humans) or plants. The dosage of such compounds can lie within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

For a compound or composition utilized for a method described herein, the therapeutically effective dose can be estimated initially from various in vitro assays, as disclosed herein. For example, a dose can be formulated in animal models to achieve a circulating concentration range that includes the $EC_{50}$ (effective dose for 50% increase) as determined in vitro, i.e., the concentration of the test compound which achieves a half-maximal lethality toward a parasite, pest or other organism of interest. Such information can be used to more accurately determine useful doses.

In general, the compounds prepared by the methods, and from the intermediates, described herein will be administered in a therapeutically effective amount by any of the accepted modes of administration for agents that serve similar utilities. It will be understood, however, that the specific dose level for any particular animal or plant will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing entity. The drug can be administered once a day or twice a day or three times a day or four times a day, or once a week or twice a week or three times a week or four times a week or once a month or twice a month or three times a month or four times a month.

Dosage amount and interval can be adjusted individually to provide plasma levels of the active moiety that are sufficient to maintain cell growth inhibitory effects.

The amount of the compound in a formulation can vary within the full range employed by those skilled in the art. Typically, the formulation will contain, on a weight percent (wt %) basis, from about 0.01-60 wt % of the drug based on the total formulation, with the balance being one or more suitable pharmaceutically acceptable excipients.

Exemplary embodiments, according to any of the above paragraphs, include 5-(5-(3,5-Dichlorophenyl)-5-(trifluoromethyl)-4,5-dihydroisoxazol-3-yl)benzo[c][1,2]oxaborol-1(3H)-ol; or 5-(5-(3,5-Dichlorophenyl)-5-(trifluoromethyl)-4,5-dihydroisoxazol-3-yl)-3,3-dimethyl-benzo[c][1,2]oxaborol-1(3H)-ol; or (S)-5-(5-(3,5-dichlorophenyl)-5-(trifluoromethyl)-4,5-dihydroisoxazol-3-yl)-3,3-dimethyl benzo[c][1,2]oxaborol-1(3H)-ol; or (R)-5-(5-(3,5-dichlorophenyl)-5-(trifluoromethyl)-4,5-dihydroisoxazol-3-yl)-3,3-dimethylbenzo[c][1,2]oxaborol-1(3H)-ol; or 5-(5-(3,5-Dibromophenyl)-5-(trifluoromethyl)-4,5-dihydroisoxazol-3-yl)-3,3-dimethyl-benzo[c][1,2]oxaborol-1(3H)-ol; or 5-(5-(3-Chloro-5-(trifluoromethyl)phenyl)-5-(trifluoromethyl)-4,5-dihydroisoxazol-3-yl)-3,3-dimethyl-benzo[c][1,2]oxaborol-1(3H)-ol; or 3,3-Dimethyl-5-(5-(3,4,5-trichlorophenyl)-5-(trifluoromethyl)-4,5-dihydroisoxazol-3-yl)benzo[c][1,2]oxaborol-1(3H)-ol; or 5-(5-(3,5-Dichlorophenyl)-5-(trifluoromethyl)-4,5-dihydroisoxazol-3-yl)-3,3-dimethyl-benzo[c][1,2]oxaborol-1(3H)-ol; or 5-(5-(3,5-Dichloro-4-methylphenyl)-5-(trifluoromethyl)-4,5-dihydroisoxazol-3-yl)-3,3-dimethylbenzo[c][1,2]oxaborol-1(3H)-ol; or 5-(5-(3,5-Dichloro-4-(trifluoromethyl)phenyl)-5-(trifluoromethyl)-4,5-dihydro isoxazol-3-yl)-3,3-dimethyl-benzo[c][1,2]oxaborol-1(3H)-ol; or 5-(5-(3,5-Dichloro-4-(difluoromethyl)phenyl)-5-(trifluoromethyl)-4,5-dihydro isoxazol-3-yl)-3,3-dimethyl-benzo[c][1,2]oxaborol-1(3H)-ol; or 5-(5-(3,5-Dichloro-4-(trifluoromethoxy)phenyl)-5-(trifluoromethyl)-4,5-dihydro-isoxazol-3-yl)-3,3-dimethylbenzo[c][1,2]oxaborol-1(3H)-ol; or 5-(5-(3,5-Dichlorophenyl)-5-(perfluoroethyl)-4,5-dihydroisoxazol-3-yl)-3,3-dimethylbenzo[c][1,2]oxaborol-1(3H)-ol; or 5-(5-(3,5-Bis(trifluoromethyl)phenyl)-5-(trifluoromethyl)-4,5-dihydroisoxazol-3-yl)-3,3-dimethylbenzo[c][1,2]oxaborol-1(3H)-ol; or 5-(5-(3,5-Dichloro-4-(2,2,2-trifluoroethoxy)phenyl)-5-(trifluoromethyl)-4,5-dihydroisoxazol-3-yl)-3,3-dimethylbenzo[c][1,2]oxaborol-1(3H)-ol; or 3,3-Dimethyl-5-(5-methyl-5-(3,4,5-trichlorophenyl)-4,5-dihydroisoxazol-3-yl)benzo[c][1,2]oxaborol-1(3H)-ol; or (S)-3,3-Dimethyl-5-(5-(3,4,5-trichlorophenyl)-5-(trifluoromethyl)-4,5-dihydroisoxazol-3-yl)benzo[c][1,2]oxaborol-1(3H)-ol; or (R)-3,3-Dimethyl-5-(5-(3,4,5-trichlorophenyl)-5-(trifluoromethyl)-4,5-dihydroisoxazol-3-yl)benzo[c][1,2]oxaborol-1(3H)-ol; or 5-(5-(3-Chloro-4-fluorophenyl)-5-(trifluoromethyl)-4,5-dihydroisoxazol-3-yl)-3,3-dimethylbenzo[c][1,2]oxaborol-1(3H)-ol; or 5-(5-(Fluoromethyl)-5-(3,4,5-trichlorophenyl)-4,5-dihydroisoxazol-3-yl)-3,3-dimethylbenzo[c][1,2]oxaborol-1(3H)-ol; or 5-(5-(4-Bromo-3,5-dichlorophenyl)-5-(trifluoromethyl)-4,5-dihydroisoxazol-3-yl)-3,3-dimethylbenzo[c][1,2]oxaborol-1(3H)-ol; or 5-(5-(3,5-Dichloro-4-methoxyphenyl)-5-(trifluoromethyl)-4,5-dihydroisoxazol-3-yl)-3,3-dimethylbenzo[c][1,2]oxaborol-1(3H)-ol; or 5-(5-(3,4-Dichlorophenyl)-5-(trifluoromethyl)-4,5-dihydroisoxazol-3-yl)-3,3-dimethyl-benzo[c][1,2]oxaborol-1(3H)-ol; or 5-(5-(4-Fluoro-3-(trifluoromethyl)phenyl)-5-(trifluoromethyl)-4,5-dihydroisoxazol-3-yl)-3,3-dimethylbenzo[c][1,2]oxaborol-1(3H)-ol; or 5-(5-(3-Chloro-4,5-difluorophenyl)-5-(trifluoromethyl)-4,5-dihydroisoxazol-3-yl)-3,3-dimethylbenzo[c][1,2]oxaborol-1(3H)-ol; or 5-(5-(3,4-Dichloro-5-fluorophenyl)-5-(trifluoromethyl)-4,5-dihydroisoxazol-3-yl)-3,3-dimethylbenzo[c][1,2]oxaborol-1(3H)-ol; or 5-(5-(3,5-Dibromo-4-chlorophenyl)-5-(trifluoromethyl)-4,5-dihydroisoxazol-3-yl)-3,3-dimethylbenzo[c][1,2]oxaborol-1(3H)-ol; or (S)-5-(5-(3,5-Dichloro-4-fluorophenyl)-5-(trifluoromethyl)-4,5-dihydroisoxazol-3-yl)-3,3-dimethylbenzo[c][1,2]oxaborol-1(3H)-ol; or (R)-5-(5-(3,5-Dichloro-4-fluorophenyl)-5-(trifluoromethyl)-4,5-dihydroisoxazol-3-yl)-3,3-dimethylbenzo[c][1,2]oxaborol-1(3H)-ol; or 5-(5-(4-Chloro-3,5-difluorophenyl)-5-(trifluoromethyl)-4,5-dihydroisoxazol-3-yl)-3,3-dimethylbenzo[c][1,2]oxaborol-1(3H)-ol; or 3,3-Dimethyl-5-(5-(trifluoromethyl)-5-(3,4,5-trifluorophenyl)-4,5-dihydroisoxazol-3-yl)benzo[c][1,2]oxaborol-1(3H)-ol; or 5-(5-(3,5-Dibromo-4-fluorophenyl)-5-(trifluoromethyl)-4,5-dihydroisoxazol-3-yl)-3,3-dimethylbenzo[c][1,2]oxaborol-1(3H)-ol; or 3,3-Bis(fluoromethyl)-5-(5-(3,4,5-trichlorophenyl)-5-(trifluoromethyl)-4,5-dihydroisoxazol-3-yl)benzo[c][1,2]oxaborol-1(3H)-ol; or 3,3-Dimethyl-5-(5-(2,3,4,5-tetrachlorophenyl)-5-(trifluoromethyl)-4,5-dihydroisoxazol-3-yl)benzo[c][1,2]oxaborol-1(3H)-ol; or 5-(5-(3,5-Dichloro-2,4-difluorophenyl)-5-(trifluoromethyl)-4,5-dihydroisoxazol-3-yl)-3,3-dimethylbenzo[c][1,2]oxaborol-1(3H)-ol; or 5-(5-(3,5-Dichlorophenyl)-5-(trifluoromethyl)-4,5-dihydroisoxazol-3-yl)-3,3-diethyl-benzo[c][1,2]oxaborol-1(3H)-ol; or 5-(5-(3,5-Dichlorophenyl)-5-(trifluoromethyl)-4,5-dihydroisoxazol-3-yl)-1H-spiro[benzo[c][1,2]oxaborole-3,1'-cyclopentan]-1-ol; or 5-(5-(3,5-Dichlorophenyl)-5-(trifluoromethyl)-4,5-dihydroisoxazol-3-yl)-1H-spiro[benzo[c][1,2]oxaborole-3,1'-cyclohexan]-1-ol; or 5-(5-(3,5-Dichlorophenyl)-5-(trifluoromethyl)-4,5-dihydroisoxazol-3-yl)-4-fluoro-3,3-dimethylbenzo[c][1,2]oxaborol-1(3H)-ol; or 4-Fluoro-3,3-dimethyl-5-(5-(3,4,5-trichlorophenyl)-5-(trifluoromethyl)-4,5-dihydro isoxazol-3-yl)benzo[c][1,2]oxaborol-1(3H)-ol; or 5-(5-(3,5-dichlorophenyl)-5-(trifluoromethyl)-4,5-dihydroisoxazol-3-yl)-6-fluoro-3,3-dimethylbenzo[c][1,2]oxaborol-1(3H)-ol; or 6-Fluoro-3,3-dimethyl-5-(5-(3,4,5-trichlorophenyl)-5-(trifluoromethyl)-4,5-dihydroisoxazol-3-yl)benzo[c][1,2]oxaborol-1(3H)-ol.

In an exemplary embodiment, the invention provides a combination comprising a compound according to any of the above paragraphs, together with at least one additional therapeutic agent.

In an exemplary embodiment, the invention provides a pharmaceutical formulation comprising: (a) a compound according to any of the above paragraphs; and (b) a pharmaceutically acceptable excipient.

In an exemplary embodiment, according to any of the above paragraphs, the pharmaceutical formulation is a unit dosage form.

In an exemplary embodiment, the salt of a compound according to any of the above paragraphs is a pharmaceutically acceptable salt.

In an exemplary embodiment, the invention is a method of killing and/or preventing the growth of an ectoparasite, comprising: contacting the ectoparasite with an effective amount of a compound according to any of the above paragraphs, thereby killing and/or preventing the growth of the ectoparasite.

In an exemplary embodiment, according to any of the above paragraphs, the ectoparasite is a tick or a flea.

In an exemplary embodiment, according to any of the above paragraphs, the ectoparasite is in or on an animal.

In an exemplary embodiment, the invention is a method of controlling an ectoparasitic infestation in or on an animal in need of treatment thereof, comprising: administering to the animal a therapeutically effective amount of a compound according to any of the above paragraphs, sufficient to control the ectoparasitic infestation.

In an exemplary embodiment, according to any of the above paragraphs, the animal is a dog or a cat.

In an exemplary embodiment, the invention is a use of the compound according to any of the above paragraphs in the manufacture of a medicament for the treatment and/or prophylaxis of ectoparasitic infection.

The invention is further illustrated by the Examples that follow. The Examples are not intended to define or limit the scope of the invention.

All solvents used were commercially available and were used without further purification. Reactions were typically run using anhydrous solvents under an inert atmosphere of $N_2$.

$^1$H, $^{13}$C, and $^{19}$F NMR spectra were recorded at 400 MHz for proton, 100 MHz for carbon-13, and 376 MHz for fluorine-19 on a Varian 300 MercuryPlus station with an Oxford AS400 Spectrometer equipped with a Varian 400 ATB PFG probe. All deuterated solvents typically contained 0.03% to 0.05% v/v tetramethylsilane, which was used as the reference signal (set at δ 0.00 for both $^1$H and $^{13}$C).

Compounds are named using ChemDraw 7.0 or their catalogue name if commercially available.

Mass spectra were recorded on a Waters MS consisting of an Alliance 2795 (LC) and Waters Micromass ZQ detector at 120° C. The mass spectrometer was equipped with an electrospray ion source (ESI) operated in a positive or negative mode. The mass spectrometer was scanned between m/z=100-1000 with a scan time of 0.3 s.

Elemental Analysis for C, H and N composition was performed using a Costech Instrument Elemental Combustion System ECS4010 with a helium flow of 100 mL/min (14 psi), oxygen 20 mL/min (10 psi), air 25 psi and purge of 50 mL/min The reported analyses are an average of two runs.

HPLC analyses were performed on a Water 600 Controller system with a Waters 717 Plus Autosampler and a Waters 2996 Photodiode Array Detector. The column used was an ACE $C_{18}$, 5 μm, 4.6×150 mm A linear gradient was applied, starting at 95% A (A: 0.1% $H_3PO_4$ in water) and ending at 90% B (B: MeCN) over 6 min and then maintained at 90% B until the 10 min mark. The column was then re-equilibrated over 3 min to 95:5 with a total run time of 20 min. The column temperature was at rt with the flow rate of 1.0 mL/min. The Diode Array Detector was scanned from 200-400 nm. For high purity samples requiring baseline subtraction, a linear gradient was applied, starting at 99% A (A: 0.1% $H_3PO_4$ in water) and ending at 90% B (B: MeCN) over 15 min. The column was then re-equilibrated over 3 min to 99% A with a total run time of 23 min. The column temperature was at rt with the flow rate of 1.0 mL/min. The Diode Array Detector was scanned from 200-400 nm. A blank MeOH sample was run immediately prior to the sample of which purity was to be determined: this was then subtracted to obtain the baseline subtracted chromatogram.

Thin layer chromatography (TLC) was performed on Alugram® (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), vanillin (generated by dissolving about 1 g vanillin in 100 mL 10% $H_2SO_4$), potassium permanganate (generated by dissolving 1.5 g $KMnO_4$ and 10 g $K_2CO_3$ in 1.25 mL NaOH and 200 mL $H_2O$), ninhydrin (available commercially from Aldrich), or Magic Stain (generated by thoroughly mixing 25 g $(NH_4)_6Mo_7O_{24} \cdot 4H_2O$, 5 g $(NH_4)_2Ce(IV)(NO_3)_6$ in 450 mL $H_2O$ and 50 mL conc $H_2SO_4$) to visualize the compound. Flash chromatography was preformed using typically 40-63 μm (230-400 mesh) silica gel from Silicycle following analogous techniques to those disclosed by Still et al. Typical solvents used for flash chromatography or thin layer chromatography (TLC) were mixtures of $CHCl_3$/MeOH, $CH_2Cl_2$/MeOH, EtOAc/MeOH and hexane/EtOAc. Reverse phase flash chromatography were performed on a Biotage® using a Biotage $C_{18}$ cartridges and a $H_2O$/MeOH gradient (typically eluting from 5% MeOH/$H_2O$ to 90% MeOH/$H_2O$).

Preparative chromatography was performed on either a Waters Prep LC 4000 System using a Waters 2487 Diode Array or on a Waters LC Module 1 plus. The column used were either a Waters×Terra Prep $C_{18}$, 5 μm, 30×100 mm, Phenomenex Luna $C_{18}$, 5 μm, 21.6×250 mm, or a Phenomenex Gemini $C_{18}$, 5 μm, 100×30 mm Narrow gradients with MeCN/$H_2O$ (water containing either 0.1% TFA, 0.1% AcOH, 0.1% $HCO_2H$ or 0.1% $NH_4OAc$) were used to elute the compound at a flow rate of approximately 20 mL/min and a total run time between 20-30 min.

For enantiomeric excess determination, chiral HPLC analysis was performed on a Waters 600 Controller and Multisolvent Delivery System using a Waters 717+ Autosampler and a Waters 996 Photodiode Array Detector with a Crownpak CR(+) column, eluting with 85:15 pH 1 perchloric acid in $H_2O$/MeOH mobile phase. The pH 1 perchloric acid was generated by adding 16.3 g of 70% perchloric acid to 1 L of distilled $H_2O$.

Starting materials used were either available from commercial sources or prepared according to literature procedures and had experimental data in accordance with those reported. 6-aminobenzo[c][1,2]oxaborol-1(3H)-ol, for example, can be synthesized according to the methods described in U.S. patent application Ser. No. 12/142,692, as well as U.S. Pat. Pubs. US20060234981 and US20070155699.

EXAMPLE 1

1. 5-(5-(3,5-Dichlorophenyl)-5-(trifluoromethyl)-4,5-dihydroisoxazol-3-yl)benzo[c][1,2]oxaborol-1(3H)-ol

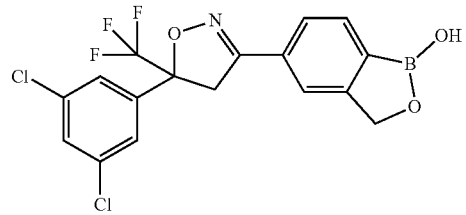 [SMILES: OB1OCc2cc(C3=NOC(c4cc(Cl)cc(Cl)c4)(C(F)(F)F)C3)ccc21]

Step 1: Preparation of methyl 4-bromo-3-methylbenzoate

A stirred suspension of 4-bromo-3-methylbenzoic acid (2.15 g, 10 mmol) in thionyl chloride (10 mL) was refluxed for 4 h, cooled to rt and concentrated under reduced pressure. The residue was dissolved in MeOH (15 mL) and the reaction mixture was refluxed for 2 h. The mixture was cooled to rt and concentrated under reduced pressure. The residue was dissolved in EA (10 mL), washed with water, dried over $MgSO_4$, filtered and concentrated under reduced pressure to give methyl 4-bromo-3-methylbenzoate (2.07 g; yield 69%) as a red solid.

Step 2: Preparation of (4-bromo-3-methylphenyl)methanol

To a solution of methyl 4-bromo-3-methylbenzoate (500 mg, 2.18 mmol) in THF (5.2 mL) at −30° C. was slowly added $LiAlH_4$ (83 mg, 2.18 mmol). The reaction mixture was stirred for 15 min, quenched with a solution of methanol and water (4:1, 10 mL), and stirred at rt for 30 min. The mixture was neutralized with 6 N HCl to pH of 7 and extracted with ethyl acetate (20 mL). The organic layer was dried over $MgSO_4$, filtered and concentrated under reduced pressure to afford (4-bromo-3-methylphenyl)methanol (420 mg; yield 96%) as an oil.

Step 3: Preparation of 4-bromo-3-methylbenzaldehyde

To a solution of (4-bromo-3-methylphenyl)methanol (420 mg, 2.09 mmol) in DCM (6 mL) at rt was added MnO₂ (1.82 g, 20.9 mmol). The reaction mixture was stirred for 12 h, filtered and concentrated under reduced pressure to give 4-bromo-3-methyl-benzaldehyde (372 mg; yield 89%) as an oil.

Step 4: Preparation of 4-bromo-3-methylbenzaldehyde oxime

To a mixture of 4-bromo-3-methyl-benzaldehyde (372 mg, 1.87 mmol) and hydroxylamine hydrochloride (306.5 mg, 4.41 mmol) in ethanol (5 mL) at rt was added Et₃N (0.15 mL). The reaction mixture was heated under reflux for 2 h, cooled to rt and concentrated under reduced pressure. The residue was dissolved in EA (10 mL), washed with water, dried over MgSO₄, filtered and concentrated under reduced pressure to give 4-bromo-3-methylbenzaldehyde oxime (384 mg; yield 96%) as a white solid.

Step 5 and 6: Preparation of 3-(4-bromo-3-methylphenyl)-5-(3,5-dichlorophenyl)-5-(trifluoromethyl)-4,5-dihydroisoxazole A mixture of 4-bromo-3-methylbenzaldehyde oxime (384 mg, 0.5 mmol) and NCS (286.7 mg, 2.14 mmol) in DMF (10 mL) was stirred at 40° C. for 40 min. The mixture was cooled to 0° C. and to it was added 1,3-dichloro-5-(3,3,3-trifluoroprop-1-en-2-yl)benzene (261 mg, 1.08 mmol) followed by Et₃N (0.15 mL). The reaction mixture was stirred at rt for 20 h, poured into water and extracted with EA (10 mL). The organic layer was washed with water, dried over MgSO₄, filtered and concentrated under reduced pressure. The residue was purified by column chromatography over silica gel to give 3-(4-bromo-3-methylphenyl)-5-(3,5-dichlorophenyl)-5-(trifluoromethyl)-4,5-dihydroisoxazole (364.2 mg; yield 82%) as a white solid.

Step 7: Preparation of 3-(4-bromo-3-(bromomethyl)phenyl)-5-(3,5-dichlorophenyl)-5-(trifluoromethyl)-4,5-dihydroisoxazole A mixture of 3-(4-bromo-3-methylphenyl)-5-(3,5-dichlorophenyl)-5-(trifluoromethyl)-4,5-dihydroisoxazole (100 mg, 0.221 mmol), NBS (62.8 mg, 0.35 mmol) and AIBN (cat.) in 1,2-dichloroethane (10 mL) was refluxed for 3.5 h and concentrated under reduced pressure. The residue was purified by column chromatography over silica gel to give crude 3-(4-bromo-3-(bromomethyl)phenyl)-5-(3,5-dichlorophenyl)-5-(trifluoromethyl)-4,5-dihydroisoxazole (50 mg, yield 42%) as an oil.

Step 8: Preparation of 2-bromo-5-(5-(3,5-dichlorophenyl)-5-(trifluoromethyl)-4,5-dihydroisoxazol-3-yl)benzyl acetate A solution of 3-(4-bromo-3-(bromomethyl)phenyl)-5-(3,5-dichlorophenyl)-5-(trifluoromethyl)-4,5-dihydroisoxazole (36 mg, 0.068 mmol) and NaOAc (6 mg, 0.074 mmol) in AcOH (1 mL) was refluxed for 16 h, cooled to rt and concentrated under reduced pressure. The residue was dissolved in EA, washed with H₂O, dried over MgSO₄, filtered and concentrated under reduced pressure to give 2-bromo-5-(5-(3,5-dichlorophenyl)-5-(trifluoromethyl)-4,5-dihydroisoxazol-3-yl)benzyl acetate (29 mg; yield 85%) as a yellow solid.

Step 9: Preparation of 5-(5-(3,5-dichlorophenyl)-5-(trifluoromethyl)-4,5-dihydroisoxazol-3-yl)-2-(4,4,5,5-tetramethyl-1,3,2-dioxaborolan-2-yl)benzyl acetate A mixture of 2-bromo-5-(5-(3,5-dichlorophenyl)-5-(trifluoromethyl)-4,5-dihydro-isoxazol-3-yl)benzyl acetate (25 mg, 0.05 mmol), bis(pinacolato)diboron (25 mg, 0.1 mmol), Pd(dppf)Cl₂ (4 mg, 0.005 mmol) and KOAc (15 mg, 0.15 mmol) in dry 1,4-dioxane (1 mL) was stirred under N₂ at rt for 0.5 h and at 100° C. for 5 h. The reaction mixture was cooled to rt and concentrated under reduced pressure. The residue was dissolved in EA, washed with H₂O, dried over MgSO₄, filtered and concentrated under reduced pressure. The residue was purified by preparative TLC to give 5-(5-(3,5-dichlorophenyl)-5-(trifluoromethyl)-4,5-dihydroisoxazol-3-yl)-2-(4,4,5,5-tetramethyl-1,3,2-dioxaborolan-2-yl)benzyl acetate (24 mg; yield 89%) as a colorless oil.

Step 10: Preparation of 5-(5-(3,5-dichlorophenyl)-5-(trifluoromethyl)-4,5-dihydro-isoxazol-3-yl)benzo[c][1,2]oxaborol-1(3H)-ol A mixture of 5-(5-(3,5-dichlorophenyl)-5-(trifluoromethyl)-4,5-dihydroisoxazol-3-yl)-2-(4,4,5,5-tetramethyl-1,3,2-dioxaborolan-2-yl)benzyl acetate (50 mg, 0.09 mmol) and LiOH·H₂O (15 mg, 0.36 mmol) in THF—H₂O (1 mL/0.2 mL) was stirred at rt for 1 h and diluted with EA (2 mL). The organic phase was dried over MgSO₄, filtered and concentrated under reduced pressure to give a residue that was dissolved in HCl-EtOH (4 N, 5 mL) and H₂O (0.3 mL). The mixture was stirred at 35° C. for 20 h. To it was added conc HCl (1.7 mL) and the reaction mixture was stirred at 60° C. for 20 h. The mixture was cooled to rt, concentrated under reduced pressure. The residue was purified by preparative TLC to give the desired title compound (10 mg; yield 27%) as a white solid. ¹H NMR (400 MHz, CDCl₃): δ 7.81 (d, J=6.8 Hz, 1 H), 7.68 (s, 1 H), 7.63 (d, J=8.0 Hz, 1 H), 7.51 (s, 2 H), 7.43 (d, J=1.2 Hz, 1 H), 5.13 (s, 2 H), 4.12 (m, 1 H), 3.74 (m, 1 H) ppm; MS: m/z=416 (M+1, ESI+).

2. 5-(5-(3,5-Dichlorophenyl)-5-(trifluoromethyl)-4,5-dihydroisoxazol-3-yl)-3,3-dimethyl-benzo[c][1,2]oxaborol-1(3H)-ol

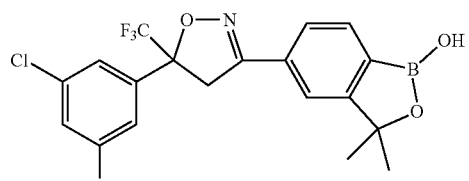

Step 1: Preparation of methyl 2-bromo-5-methylbenzoate

To a solution of 2-bromo-5-methylbenzoic acid (215 mg, 1.0 mmol) in DCM (4 mL) and DMF (1 drop) at 0° C. was slowly added oxalyl chloride (0.13 mL, 1.5 mmol). The reaction mixture was stirred at rt for 1 h and to it was added additional oxalyl chloride (0.13 mL, 1.5 mmol). The reaction mixture was stirred for 1 h, added with MeOH (2 mL) and stirred for 6 h. The mixture was treated with $Na_2CO_3$ to pH of 9 and extracted with DCM (2×10 mL). The combined organic layers were washed with brine, dried over $Na_2SO_4$, filtered and concentrated under reduced pressure. The residue was purified by column chromatography over silica gel eluted with PE-EA (15:1) to give methyl 2-bromo-5-methylbenzoate (210 mg; yield 92%) as colorless oil. $^1$H NMR (400 MHz, $CDCl_3$): δ 7.60 (d, J=1.6 Hz, 1 H), 7.53 (d, J=8.8 Hz, 1 H), 7.15 (q, J=3.2 Hz, 1H), 3.92 (s, 3 H), 2.33 (s, 3 H) ppm.

Step 2: Preparation of 2-(2-bromo-5-methylphenyl)propan-2-ol

To a solution of methyl 2-bromo-5-methylbenzoate (193 mg, 0.84 mmol) in THF (4 mL) was added dropwise MeMgBr (1.1 mL, 3.37 mmol) at 0° C. under argon and then stirred at rt for 3 h. The reaction mixture was quenched with saturated $NH_4Cl$ and extracted with EA. The combined organic layer was washed with $NaHCO_3$ solution and brine, dried over $Na_2SO_4$. The solution was concentrated and the residue was purified by column chromatography over silica gel eluted with PE-EA (30:1~20:1) to provide 2-(2-bromo-5-methylphenyl)propan-2-ol (134 mg; yield 69%) as a white solid. $^1$H NMR (400 MHz, $CDCl_3$): δ 7.49 (q, J=2.0 Hz, 2 H), 6.94 (q, J=2.0 Hz, 1 H), 2.63 (s, 1 H), 2.33 (s, 3 H), 1.76 (s, 6 H) ppm.

Step 3: Preparation of 3,3,5-trimethylbenzo[c][1,2]oxaborol-1(3H)-ol

To a solution of 2-(2-bromo-5-methylphenyl)propan-2-ol (134 mg, 0.585 mmol) in THF (5 mL) at −78° C. was slowly added n-BuLi (1.1 mL, 1.75 mmol). The reaction mixture was stirred for 2 h and to it was added B(OPr-i)$_3$ (0.203 mL, 0.88 mmol). The reaction mixture was allowed to warm to rt and stirred at rt for 6 h. The mixture was cooled to 0° C., treated with 3 N HCl (10 mL), stirred for 3 h and extracted with EA. The organic layer was washed with brine, dried over $Na_2SO_4$, filtered and concentrated under reduced pressure. The residue was purified by column chromatography over silica gel eluted with PE-EA (10:1~5:1) to give 3,3,5-trimethylbenzo[c][1,2]oxaborol-1(3H)-ol (27 mg; yield 26%) as a colorless oil. $^1$H NMR (400 MHz, $CDCl_3$): δ 7.61 (d, J=7.6 Hz, 1 H), 7.20 (d, J=7.2 Hz, 1 H), 7.09 (s, 1 H), 2.44 (s, 3 H), 1.56 (s, 6 H) ppm.

Step 4: Preparation of 1-hydroxy-3,3-dimethyl-1,3-dihydrobenzo[c][1,2]oxaborole-5-carbaldehyde To a solution of 3,3,5-trimethylbenzo[c][1,2]oxaborol-1 (3H)-ol (27 mg, 0.153 mmol) in $CCl_4$ (2 mL) at rt was added benzoyl peroxide (3.7 mg, 0.0153 mmol) followed by NBS (60 mg, 0.337 mmol). The reaction mixture was heated under reflux for 12 h, cooled to rt and treated with $Na_2CO_3$. The aqueous layer was acidified with 3 N HCl to pH of 3 and extracted with EA. The organic layer was washed with brine, dried over $Na_2SO_4$, filtered and concentrated under reduced pressure. The residue was purified by prep-TLC to give 1-hydroxy-3,3-dimethyl-1,3-dihydrobenzo[c][1,2]oxaborole-5-carbaldehyde (12 mg; yield 41%) as white solid. $^1$H NMR (400 MHz, $CDCl_3$): δ 10.12 (s, 1 H), 7.88 (s, 2 H), 7.80 (s, 1 H), 1.62 (s, 6 H) ppm.

Step 5: Preparation of 1-hydroxy-3,3-dimethyl-1,3-dihydrobenzo[c][1,2]oxaborole-5-carbaldehyde oxime To a solution of 1-hydroxy-3,3-dimethyl-1,3-dihydrobenzo[c][1,2]oxaborole-5-carbaldehyde (10 mg, 0.053 mmol) and $NH_2OH·HCl$ (4.4 mg, 0.063 mmol) in THF (4 mL) and $H_2O$ (1 mL) at rt was added NaOAc (6 mg, 0.074 mmol). The reaction mixture was stirred for 3 h and diluted with $H_2O$. The mixture was extracted with EA and the organic layer was separated. The organic solution was washed with brine, dried over $Na_2SO_4$, filtered and concentrated under reduced pressure. The residue was purified by prep-TLC to provide 1-hydroxy-3,3-dimethyl-1,3-dihydrobenzo[c][1,2]oxaborole-5-carbaldehyde oxime (8 mg; yield 74%) as a colorless oil. $^1$H NMR (400 MHz, $CDCl_3$): δ 8.23 (s, 1 H), 7.76 (d, J=7.6 Hz, 1 H), 7.55 (m, 2 H), 2.81 (s, 1 H), 1.61 (s, 6 H) ppm.

Step 6: Preparation of N,1-dihydroxy-3,3-dimethyl-1, 3-dihydrobenzo[c][1,2]oxaborole-5-carbimidoyl chloride To a solution of 1-hydroxy-3,3-dimethyl-1,3-dihydrobenzo[c][1,2]oxaborole-5-carbaldehyde oxime (8 mg, 0.039 mmol) in DMF (1.0 mL) at rt was added NCS (6.2 mg, 0.047 mmol). The reaction mixture was stirred for 2 h, warmed to 40° C. and stirred for 3 h. The mixture was cooled to rt, poured into ice-water (10 mL) and extracted with EA (20 mL). The organic layer was washed with brine, dried over $Na_2SO_4$, filtered and concentrated under reduced pressure to give N,1-dihydroxy-3,3-dimethyl-1,3-dihydrobenzo[c][1,2] oxaborole-5-carbimidoyl chloride (8 mg; yield 86%) as a white solid. $^1$H NMR (400 MHz, $CDCl_3$): δ 12.50 (s, 1 H), 7.90 (s, 1 H), 7.70-7.79 (m, 2 H), 1.61 (s, 6 H) ppm.

Step 7: Preparation of 1,3-dichloro-5-(3,3,3-trifluoroprop-1-en-2-yl)benzene

A mixture of 3,5-dichlorophenylboronic acid (5 g, 26.2 mmol), 2-bromo-3,3,3-trifluoroprop-1-ene (5 g, 28.6 mmol), $K_2CO_3$ (7.24 g, 52.4 mmol) and $Pd(PPh_3)_2Cl_2$ (368 mg) in THF (20 mL) and $H_2O$ (10 mL) was heated at 70° C. in a sealed tube for 4 h. The mixture was cooled to rt and partitioned between ether (50 mL) and $H_2O$ (50 mL). The aqueous layer was extracted with ether (50 mL) and the combined organic layers were dried over $Na_2SO_4$. The solvent was removed under reduced pressure and the crude product was purified by column chromatography over silica gel eluted with hexanes to afford 1,3-dichloro-5-(3,3,3-trifluoroprop-1-en-2-yl)benzene (5.77 g; yield 85%) as a white solid. $^1$H NMR (400 MHz, $CDCl_3$): δ 7.42 (t, J=2.0 Hz, 2 H), 7.34 (d, J=2.0 Hz, 1 H), 6.05 (s, 1 H), 5.82 (s, 1 H) ppm.

Step 8: Preparation of 5-(5-(3,5-dichlorophenyl)-5-(trifluoromethyl)-4,5-dihydro-isoxazol-3-yl)-3,3-dimethyl-benzo[c][1,2]oxaborol-1(3H)-ol To a solution of N,1-dihydroxy-3,3-dimethyl-1,3-dihydrobenzo[c][1,2]oxaborole-5-carbimidoyl chloride (8 mg, 0.033 mmol) and 1,3-dichloro-5-(3,3,3-trifluoroprop-1-en-2-yl)benzene (8.9 mg, 0.0367 mmol) in DMF (1 mL) at rt was added TEA (5.1 μL, 0.0367 mmol). The reaction mixture was stirred for 12 h, poured into ice-water and extracted with EA (10 mL). The organic layer was washed with brine, dried over $Na_2SO_4$, filtered and concentrated under reduced pressure. The residue was purified by prep-TLC to give the title compound 5-(5-(3,5-dichlorophenyl)-5-(trifluoromethyl)-4,5-dihydro-isoxazol-3-yl)-3,3-dimethyl-benzo[c][1,2]oxaborol-1(3H)-ol (9.5 mg; yield 64%) as a light yellow solid. $^1$H NMR (400 MHz, DMSO-$d_6$): δ 9.26 (s, 1 H), 7.66-7.85 (m, 6 H), 4.32-4.96 (m, 2 H), 1.51 (s, 6 H) ppm; MS: m/z=444 (M+1, ESI+).

3. (S)-5-(5-(3,5-dichlorophenyl)-5-(trifluoromethyl)-4,5-dihydroisoxazol-3-yl)-3,3-dimethyl benzo[c][1,2]oxaborol-1(3H)-ol

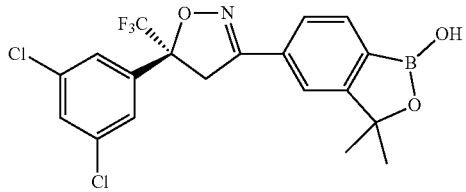 [SMILES: CC1(C)OB(O)c2ccc(C3=NO[C@@](c4cc(Cl)cc(Cl)c4)(C(F)(F)F)C3)cc21]

The title compound was obtained by separation of the racemic mixture of 5-(5-(3,5-dichlorophenyl)-5-(trifluoromethyl)-4,5-dihydroisoxazol-3-yl)-3,3-dimethyl-benzo[c][1,2]oxaborol-1(3H)-ol with chiral column chromatography. MS: m/z=444 (M+1, ESI+). The racemic mixture was dissolved in the solvent of mobile phase and separated by supercritical fluid (SFC) chiral chromatography. The chromatography conditions used were: column CHIRALCEL OJ-H (column size: 0.46 cm I.D.×15 cm length), mobile phase $CO_2$/MeOH=70/30 (w/w), flow rate 2.0 mL/min, detector wave length UV 220 nm, and temperature 35° C.

4. (R)-5-(5-(3,5-dichlorophenyl)-5-(trifluoromethyl)-4,5-dihydroisoxazol-3-yl)-3,3-dimethylbenzo[c][1,2]oxaborol-1(3H)-ol

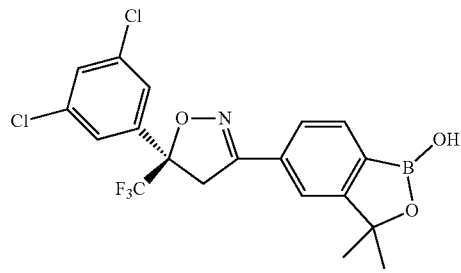 [SMILES: CC1(C)OB(O)c2ccc(C3=NO[C@](c4cc(Cl)cc(Cl)c4)(C(F)(F)F)C3)cc21]

The title compound was obtained by separation of the racemic mixture of 5-(5-(3,5-dichlorophenyl)-5-(trifluoromethyl)-4,5-dihydroisoxazol-3-yl)-3,3-dimethyl-benzo[c][1,2]oxaborol-1(3H)-ol with chiral column chromatography. MS: m/z=444 (M+1, ESI+). The racemic mixture was dissolved in the solvent of mobile phase and separated by supercritical fluid (SFC) chiral chromatography. The chromatography conditions used were: column CHIRALCEL OJ-H (column size: 0.46 cm I.D.×15 cm length), mobile phase $CO_2$/MeOH=70/30 (w/w), flow rate 2.0 mL/min, detector wave length UV 220 nm, and temperature 35° C.

5. 5-(5-(3,5-Dibromophenyl)-5-(trifluoromethyl)-4,5-dihydroisoxazol-3-yl)-3,3-dimethyl-benzo[c][1,2]oxaborol-1(3H)-ol

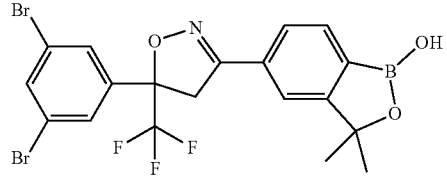 [SMILES: CC1(C)OB(O)c2ccc(C3=NOC(c4cc(Br)cc(Br)c4)(C(F)(F)F)C3)cc21]

Step 1: Preparation of 1,3-dibromo-5-(3,3,3-trifluoroprop-1-en-2-yl)benzene

A mixture of 3,5-dibromophenylboronic acid (2.58 g, 9.2 mmol), 2-bromo-3,3,3-trifluoroprop-1-ene (2.42 g, 13.8 mmol), $K_2CO_3$ (2.54 g, 18.4 mmol) and Pd(PPh$_3$)$_2$Cl$_2$ (129 mg, 0.18 mmol) in THF (12 mL) and $H_2O$ (6 mL) was heated at 80° C. in a sealed tube for 4 h. The mixture was cooled to rt and partitioned between EA (50 mL) and $H_2O$ (50 mL). The aqueous layer was extracted with EA (50 mL) and the combined organic layers were dried over $Na_2SO_4$. The solvent was removed under reduced pressure and the crude product was purified by column chromatography on silica gel to give the crude desired product (2.3 g; 76% yield) as colorless oil.

Step 2: Preparation of 5-(5-(3,5-dibromophenyl)-5-(trifluoromethyl)-4,5-dihydro-isoxazol-3-yl)-3,3-dimethylbenzo[c][1,2]oxaborol-1(3H)-ol To a solution of (Z)-N,1-dihydroxy-3,3-dimethyl-1,3-dihydrobenzo[c][1,2]oxaborole-5-carbimidoyl chloride (850 mg, 3.55 mmol) and 1,3-dibromo-5-(3,3,3-trifluoroprop-1-en-2-yl)benzene (1.75 g, 5.32 mmol) in DMF (10 mL) at rt was added TEA (0.5 mL, 3.55 mmol). The reaction mixture was stirred at rt for 18 h, poured into ice-water and extracted with EA (20 mL). The organic layer was washed with brine, dried over $Na_2SO_4$, filtered and concentrated under reduced pressure. The residue was purified by column chromatography to give the desired title compound 5-(5-(3,5-dibromophenyl)-5-(trifluoromethyl)-4,5-dihydroisoxazol-3-yl)-3,3-dimethylbenzo[c][1,2]oxaborol-1(3H)-ol (600 mg; 32% yield) as a white solid. $^1$H NMR (400 MHz, DMSO-$d_6$): δ 9.22 (s, 1H), 8.06 (d, J=2.0 Hz, 1H), 7.79 (m, 4H), 7.73 (dd, J=8.0 Hz, 0.8 Hz, 1H), 4.45 (d, J=18.8 Hz, 1H), 4.33 (d, J=18 Hz, 1H), 1.50 (d, J=2.8 Hz, 6H) ppm; HPLC purity: 100% at 220 nm and 100% at 254 nm; MS: m/z=534.0 (M+1, ESI+).

6. 5-(5-(3-Chloro-5-(trifluoromethyl)phenyl)-5-(trifluoromethyl)-4,5-dihydroisoxazol-3-yl)-3,3-dimethylbenzo[c][1,2]oxaborol-1(3H)-ol

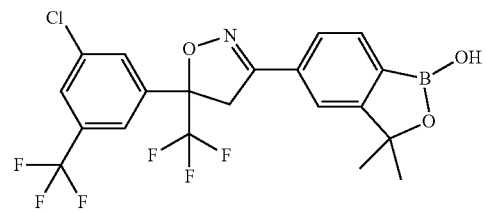 [SMILES: CC1(C)OB(O)c2ccc(C3=NOC(c4cc(Cl)cc(C(F)(F)F)c4)(C(F)(F)F)C3)cc21]

The title compound was prepared by using the same method as described in 5-(5-(3,5-dichlorophenyl)-5-(trifluoromethyl)-4,5-dihydroisoxazol-3-yl)-3,3-dimethyl-benzo[c][1,2]oxaborol-1(3H)-ol with 1-chloro-3-(trifluoromethyl)-5-(3,3,3-trifluoroprop-1-en-2-yl)benzene to replace 1,3-dichloro-5-(3,3,3-trifluoroprop-1-en-2-yl)benzene. It was obtained as a white solid. MS: m/z=478.1 [M+1]⁺.

7. 3,3-Dimethyl-5-(5-(3,4,5-trichlorophenyl)-5-(trifluoromethyl)-4,5-dihydroisoxazol-3-yl)benzo[c][1,2]oxaborol-1(3H)-ol

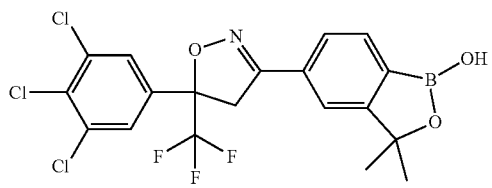 [SMILES: CC1(C)OB(O)c2ccc(C3=NOC(c4cc(Cl)c(Cl)c(Cl)c4)(C(F)(F)F)C3)cc21]

Step 1: Preparation of 1,2,3-trichloro-5-(3,3,3-trifluoroprop-1-en-2-yl)benzene A mixture of 3,4,5-trichlorophenylboronic acid (3.376 g, 15 mmol), 2-bromo-3,3,3-trifluoroprop-1-ene (4.02 g, 23 mmol), $K_2CO_3$ (4.15 g, 30 mmol) and $Pd(PPh_3)_2Cl_2$ (4.15 g, 30 mmol) in THF (16 mL) and $H_2O$ (8 mL) was heated at 80° C. in a sealed tube for 4 h. The mixture was cooled to rt and partitioned between EA (50 mL) and $H_2O$ (50 mL). The aqueous layer was extracted with EA (50 mL) and the combined organic layers were dried over anhydrous $Na_2SO_4$. The solvent was removed under reduced pressure and the crude product was purified by column chromatography on silica gel to give the crude desired product (3.7 g; 90% yield) as a pale yellow solid.

Step 2: Preparation of 1-hydroxy-3,3-dimethyl-1,3-dihydrobenzo[c][1,2]oxaborole-5-carbaldehyde oxime To a mixture of 1-hydroxy-3,3-dimethyl-1,3-dihydrobenzo[c][1,2]oxaborole-5-carbaldehyde (560 mg, 2.95 mmol) and $NH_2OH \cdot HCl$ (246 mg, 3.54 mmol) in THF (6 mL) and $H_2O$ (1.5 mL) at rt was added NaOAc (339 mg, 4.13 mmol). The reaction mixture was stirred at rt for 16 h, diluted with $H_2O$ and extracted with EA (10 mL×2). The combined organic layers were washed with brine, dried over $Na_2SO_4$, filtered and concentrated under reduced pressure to give the desired product (620 mg, 100% yield) as a white solid.

Step 3: Preparation of (Z)-N,1-dihydroxy-3,3-dimethyl-1,3-dihydrobenzo[c][1,2]oxaborole-5-carbimidoyl chloride To a solution of 1-hydroxy-3,3-dimethyl-1,3-dihydrobenzo[c][1,2]oxaborole-5-carbaldehyde oxime (1.38 g, 6.73 mmol) in DMF (15 mL) at rt was added NCS (1.07 g, 8.03 mmol). The reaction mixture was warmed to 45° C., stirred for 3 h and cooled to rt. The mixture was poured into ice-water (20 mL) and extracted with EA (20 mL×2). The combined organic layers were washed with brine, dried over $Na_2SO_4$, filtered and concentrated under reduced pressure to give the desired product (1.7 g, 100% yield) as a white solid.

Step 4: Preparation of 3,3-dimethyl-5-(5-(3,4,5-trichlorophenyl)-5-(trifluoromethyl)-4,5-dihydroisoxazol-3-yl)benzo[c][1,2]oxaborol-1(3H)-ol To a solution of N,1-dihydroxy-3,3-dimethyl-1,3-dihydrobenzo[c][1,2]oxaborole-5-carbimidoyl chloride (850 mg, 3.55 mmol) and 1,2,3-trichloro-5-(3,3,3-trifluoroprop-1-en-2-yl)benzene (1.47 g, 5.32 mmol) in DMF (10 mL) at rt was added TEA (0.5 mL, 3.55 mmol). The reaction mixture was stirred at rt for 18 h, poured into ice-water and extracted with EA (20 mL). The organic layer was washed with brine, dried over $Na_2SO_4$, filtered and concentrated under reduced pressure. The residue was purified by column chromatography to give the desired title compound 3,3-dimethyl-5-(5-(3,4,5-trichlorophenyl)-5-(trifluoromethyl)-4,5-dihydroisoxazol-3-yl)benzo[c][1,2]oxaborol-1(3H)-ol (510 mg; 30% yield) as a white solid. ¹H NMR (400 MHz, DMSO-$d_6$): δ 9.25 (s, 1H), 7.86 (s, 2H), 7.78 (s, 2H), 7.72 (d, J=7.2 Hz, 1H), 4.46 (d, J=19.2 Hz, 1H), 4.35 (d, J=18.4 Hz, 1H), 1.49 (s, 6H) ppm; HPLC purity: 95.3% at 220 nm and 96.8% at 254 nm; MS: m/z=478.4 (M+, ESI+).

8. 5-(5-(3,5-dichloro-4-fluorophenyl)-5-(trifluoromethyl)-4,5-dihydroisoxazol-3-yl)-3,3-dimethyl-benzo[c][1,2]oxaborol-1(3H)-ol

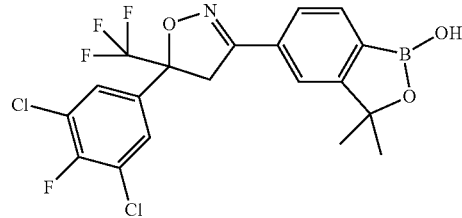 [SMILES: CC1(C)OB(O)c2ccc(C3=NOC(c4cc(Cl)c(F)c(Cl)c4)(C(F)(F)F)C3)cc21]

Step 1: Preparation of 2-(3,5-dichloro-4-fluorophenyl)-4,4,5,5-tetramethyl-1,3,2-dioxaborolane 4,4,4',4',5,5,5',5'-Octamethyl[2,2'-bi-1,3,2-dioxaborolane] (2.0 g, 7.88 mmol), 2,6-bis(1-methylethyl)-N-(2-pyridinylmethylene)benzenamine (0.080 g, 0.30 mmol), and bis(1,5-cyclooctadiene)diiridium dichloride (0.132 g, 0.20 mmol) were added to a solution of 1,3-dichloro-2-fluorobenzene (2.0 g, 12.12 mmol) in heptane (40 mL). The reaction mixture turned from yellow to forest green to brick red within the first minute. The reaction mixture was refluxed for 18 h. The mixture was then partitioned between EA and water, and the aqueous extract was washed twice with EA. The organic extracts were combined, dried over $Na_2SO_4$, and concentrated under reduced pressure. The solid residue was purified by chromatography on silica gel eluted with PE-EA (10:1) to give 2-(3,5-dichloro-4-fluorophenyl)-4,4,5,5-tetramethyl-1,3,2-dioxaborolane (2.56 g, yield 72.5%) as a white solid. ¹H NMR (500 MHz, CDCl₃): δ 7.646 (d, J=6.5 Hz, 2H), 1.266 (s, 12 H) ppm.

Step 2: Preparation of 1,3-dichloro-2-fluoro-5-(3,3,3-trifluoroprop-1-en-2-yl)benzene A mixture of 2-(3,5-dichloro-4-fluorophenyl)-4,4,5,5-tetramethyl-1,3,2-dioxaborolane (2.56 g, 8.83 mmol), 2-bromo-3,3,3-trifluoroprop-1-ene (1.85 g, 10.6 mmol), $Cs_2CO_3$ (11.5 mL, 2M, 17.7 mmol) and $Pd(PPh_3)_2Cl_2$ (200 mg) in THF (30 mL) was heated at 70° C. in a sealed tube for 4 h. The mixture was cooled to rt and partitioned between ether and $H_2O$. The aqueous layer was extracted with EA and the combined organic layers were dried over $Na_2SO_4$. The solvent was removed under reduced pressure and the crude product was purified by column chromatography on silica gel eluted with hexanes to give 1,3-dichloro-2-fluoro-5-(3,3,3-trifluoroprop-1-en-2-yl)benzene (1.3 g; yield 56%) as colorless oil. $^1$H NMR (500 MHz, $CDCl_3$): δ 7.412 (d, J=6.5 Hz, 2 H), 6.057 (s, 1 H), 5.806 (s, 1 H) ppm.

Step 3: Preparation of 5-(5-(3,5-dichloro-4-fluorophenyl)-5-(trifluoromethyl)-4,5-dihydroisoxazol-3-yl)-3,3-dimethyl-benzo[c][1,2]oxaborol-1(3H)-ol To a solution of the crude compound N,1-dihydroxy-3,3-dimethyl-1,3-dihydrobenzo[c][1,2]oxaborole-5-carbimidoyl chloride (383 mg, 1.60 mmol) and 1,3-dichloro-2-fluoro-5-(3,3,3-trifluoroprop-1-en-2-yl)benzene (455 mg, 1.76 mmol) in DMF (12 mL) at rt was added TEA (445 μL, 3.20 mmol). The reaction mixture was stirred for 12 h, poured into ice-water and extracted with EA. The organic layer was washed with brine, dried over $Na_2SO_4$, filtered and concentrated under reduced pressure. The residue was purified by prep-TLC eluted with PE-EA (3:2) and then purified by combiflash to give the title compound 5-(5-(3,5-dichloro-4-fluorophenyl)-5-(trifluoromethyl)-4,5-dihydroisoxazol-3-yl)-3,3-dimethylbenzo[c][1,2]oxaborol-1(3H)-ol (180 mg; yield 24% over the 3 steps from the aldehyde) as a white solid. $^1$H NMR (500 MHz, DMSO-$d_6$): δ 9.236 (s, 1 H), 7.803 (d, J=6.5 Hz, 2 H), 7.757-7.770 (m, 2H), 7.693-7.710 (m, 1H), 4.414 (d, J=18.0 Hz, 1 H), 4.316 (d, J=18.0 Hz, 1 H), 1.481 (s, 6 H) ppm; HPLC purity: 99.13% at 220 nm and 99.15% at 254 nm; MS: m/z=461.9 (M+1, ESI+).

9. 5-(5-(3,5-Dichloro-4-methylphenyl)-5-(trifluoromethyl)-4,5-dihydroisoxazol-3-yl)-3,3-dimethyl-benzo[c][1,2]oxaborol-1(3H)-ol

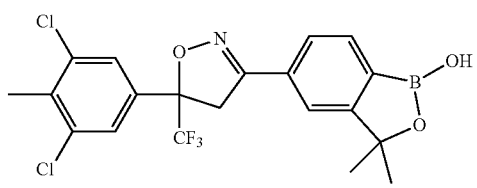 [SMILES: Cc1c(Cl)cc(C2(C(F)(F)F)CC(c3ccc4c(c3)C(C)(C)OB4O)=NO2)cc1Cl]

Preparation of 1,3-dichloro-5-iodo-2-methylbenzene

To the mixture of LDA (5 mL, 8.6 mmol) in THF (20 mL) was added compound 1,3-dichloro-5-iodobenzene (2.35 g, 8.6 mmol) under −78° C. Then the mixture was added to the pre-cooled solution of $(CH_3)_2SO_4$ (12 mL, 10.3 mmol) in THF (10 mL) under −78° C. The solution was concentrated under vacuum. The residue was diluted with EA, washed with 1N HCl, 1N NaOH, brine, dried over $Na_2SO_4$, concentrated under vacuum to give the desired product (2.3 g, 93% yield).

Preparation of 2-(3,5-dichloro-4-methylphenyl)-4,4,5,5-tetramethyl-1,3,2-dioxaborolane The mixture of 1,3-dichloro-5-iodo-2-methylbenzene (287 mg, 1.0 mmol), KOAc (294 mg, 3.0 mmol), $Pin_2B_2$ (280 mg, 1.1 mmol) and Pd(dppf)$Cl_2$ (73 mg, 0.1 mmol) in DMF (5 mL) was stirred at 80° C. for 1 h. It was partitioned between EA and $H_2O$. The organic layer was washed with $H_2O$, brine, dried over $Na_2SO_4$, concentrated under vacuum. The residue was purified by column chromatography to give the desired product (179 mg, 62% yield).

Preparation of 1,3-dichloro-2-methyl-5-(3,3,3-trifluoroprop-1-en-2-yl)benzene

The mixture of 2-(3,5-dichloro-4-methylphenyl)-4,4,5,5-tetramethyl-1,3,2-dioxaborolane (160 mg, 0.56 mmol), $K_2CO_3$ (232 mg, 1.68 mmol), compound 2-bromo-3,3,3-trifluoroprop-1-ene (146 mg, 0.84 mmol) and Pd(PPh$_3$)$_2$Cl$_2$ (39 mg, 0.1 mmol) in THF/$H_2O$ (2/1 mL) was stirred in a sealed tube at 80° C. for 3 h. It was partitioned between EA and $H_2O$. The organic layer was washed with brine, dried over $Na_2SO_4$, concentrated under vacuum. The residue was purified by column chromatography to give the desired product (78 mg, 55% yield).

Preparation of 5-(5-(3,5-dichloro-4-methylphenyl)-5-(trifluoromethyl)-4,5-dihydroisoxazol-3-yl)-3,3-dimethylbenzo[c][1,2]oxaborol-1(3H)-ol The mixture of (E)-1-hydroxy-3,3-dimethyl-1,3-dihydrobenzo[c][1,2]oxaborole-5-carbaldehyde oxime (62 mg, 0.3 mmol) and NCS (48 mg, 0.36 mmol) in DMF (2 mL) was stirred at rt overnight. To the mixture was added 1,3-dichloro-2-methyl-5-(3,3,3-trifluoroprop-1-en-2-yl)benzene (75 mg, 0.3 mmol) and $Et_3N$ (0.1 mL) and the mixture was stirred at rt for 4 h. It was partitioned between EA and $H_2O$. The organic layer was washed with $H_2O$, brine, dried over $Na_2SO_4$, concentrated under vacuum. The residue was purified to give the desired product (30 mg, 21.8% yield). $^1$H NMR (400 MHz, DMSO-$d_6$): δ 9.20 (s, 1H), 7.77-7.70 (m, 3H), 7.63 (s, 2H), 4.42 (d, J=18.4 Hz, 1H), 4.30 (d, J=18.4 Hz, 1H), 2.45 (s, 3H), 1.48 (d, J=2.4 Hz, 6H), ppm; HPLC purity: 98.6% at 220 nm and 98.9% at 254 nm; MS: m/z=458.5 (M+1, ESI+).

10. 5-(5-(3,5-Dichloro-4-(trifluoromethyl)phenyl)-5-(trifluoromethyl)-4,5-dihydro isoxazol-3-yl)-3,3-dimethyl-benzo[c][1,2]oxaborol-1(3H)-ol

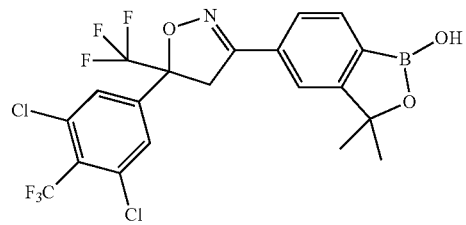 [SMILES: CC1(C)OB(O)c2ccc(C3=NOC(c4cc(Cl)c(C(F)(F)F)c(Cl)c4)(C(F)(F)F)C3)cc21]

Step 1: Preparation of 2-(3,5-dichloro-4-(trifluoromethyl)phenyl)-4,4,5,5-tetramethyl-1,3,2-dioxaborolane 4,4,4',4',5,5,5',5'-Octamethyl[2,2'-bi-1,3,2-dioxaborolane] (0.50 g, 1.97 mmol), 2,6-bis(1-methylethyl)-N-(2-pyridinylmethylene)benzenamine (0.020 g, 0.075 mmol), and bis(1,5-cyclooctadiene)diiridium dichloride (0.033 g, 0.049 mmol) were added to a solution of 1,3-dichloro-2-(trifluoromethyl)benzene (0.65 g, 3.02 mmol) in heptane (10 mL). The reaction mixture turned from yellow to forest green to brick red within the first minute. The reaction mixture was refluxed for 18 h. The mixture was then partitioned between EA and water, and the aqueous extract was washed twice with EA. The organic extracts were combined, dried over $Na_2SO_4$, and concentrated under reduced pressure. The solid residue was purified by chromatography on silica gel eluted with PE-EA (8:1) to give 2-(3,5-dichloro-4-(trifluoromethyl)phenyl)-4,4,5,5-tetramethyl-1,3,2-dioxaborolane (0.89 g, yield 86%) as a white solid. $^1$H NMR (500 MHz, $CDCl_3$): δ 7.721 (s, 2H), 1.278 (s, 12 H) ppm.

Step 2: Preparation of 1,3-dichloro-2-(trifluoromethyl)-5-(3,3,3-trifluoroprop-1-en-2-yl)benzene A mixture of 2-(3,5-dichloro-4-(trifluoromethyl)phenyl)-4,4,5,5-tetramethyl-1,3,2-dioxaborolane (0.62 g, 1.8 mmol), 2-bromo-3,3,3-trifluoroprop-1-ene (0.38 g, 2.16 mmol), $Cs_2CO_3$ (1.8 mL, 2M, 3.6 mmol) and $Pd(PPh_3)_2Cl_2$ (38 mg) in THF (10 mL) was heated at 70° C. in a sealed tube for 4 h. The mixture was cooled to rt and partitioned between ether and $H_2O$. The aqueous layer was extracted with EA and the combined organic layers were dried over $Na_2SO_4$. The solvent was removed under reduced pressure and the crude product was purified by column chromatography on silica gel eluted with hexanes to give 1,3-dichloro-2-(trifluoromethyl)-5-(3,3,3-trifluoroprop-1-en-2-yl)benzene (0.295 g; yield 53%) as colorless oil. $^1$H NMR (500 MHz, $CDCl_3$): δ 7.433 (s, 2H), 6.073 (s, 1 H), 5.846 (s, 1 H) ppm.

Step 3: Preparation of 5-(5-(3,5-dichloro-4-(trifluoromethyl)phenyl)-5-(trifluoromethyl)-4,5-dihydro-isoxazol-3-yl)-3,3-dimethyl-benzo[c][1,2]oxaborol-1(3H)-ol To a solution of crude N,1-dihydroxy-3,3-dimethyl-1,3-dihydrobenzo[c][1,2]oxaborole-5-carbimidoyl chloride (93 mg, 0.39 mmol) and 1,3-dichloro-2-(trifluoromethyl)-5-(3,3,3-trifluoroprop-1-en-2-yl)benzene (133 mg, 0.43 mmol) in DMF (5 mL) at rt was added TEA (60 μL, 0.43 mmol). The reaction mixture was stirred for 12 h, poured into ice-water and extracted with EA. The organic layer was washed with brine, dried over $Na_2SO_4$, filtered and concentrated under reduced pressure. The residue was purified by prep-TLC eluted with PE-EA (3:2) and then purified by combiflash to give the title compound 5-(5-(3,5-dichloro-4-(trifluoromethyl)phenyl)-5-(trifluoromethyl)-4,5-dihydro-isoxazol-3-yl)-3,3-dimethyl-benzo[c][1,2]oxaborol-1(3H)-ol (50 mg; yield 25% over 3 steps) as a white solid. $^1$H NMR (500 MHz, DMSO-$d_6$): δ 9.220 (s, 1 H), 7.837 (s, 2 H), 7.716-7.731 (m, 2 H), 7.650-7.666 (m, 1H), 4.423 (d, J=18.0 Hz, 1 H), 4.311 (d, J=18.0 Hz, 1 H), 1.432 (s, 6 H) ppm; HPLC purity: 99.3% at 220 nm and 99.4% at 254 nm.

11. 5-(5-(3,5-Dichloro-4-(difluoromethyl)phenyl)-5-(trifluoromethyl)-4,5-dihydro isoxazol-3-yl)-3,3-dimethyl-benzo[c][1,2]oxaborol-1(3H)-ol

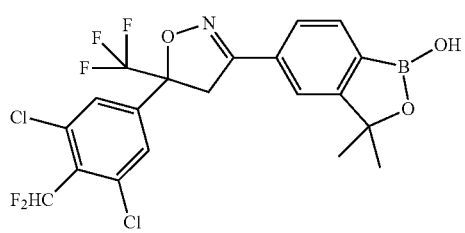 [SMILES: CC1(C)OB(O)c2ccc(C3=NOC(c4cc(Cl)c(C(F)F)c(Cl)c4)(C(F)(F)F)C3)cc21]

Step 1: Preparation of 1,3-dichloro-2-(difluoromethyl)benzene

Compound 2,6-dichlorobenzaldehyde (3.94 g, 22.5 mmol) was placed in a Teflon-coated flask and dissolved in DCM (200 mL). BAST (9.96 g, 45 mmol) was slowly added and the reaction mixture was stirred at rt overnight. The reaction mixture was then slowly added to a vigorously stirring $NaHCO_3$-saturated aqueous solution (400 mL) under cooling with ice. After 1 h the phases were separated and the aqueous layer was extracted with DCM three times. The combined organic layers were washed twice with water, dried over $Na_2SO_4$, filtered and evaporated to dryness. The residue was purified by column chromatography on silica gel eluted with PE-EA (15:1) to give 1,3-dichloro-2-(difluoromethyl)benzene (3.56 g; yield 80%) as colorless oil. $^1$H NMR (500 MHz, $CDCl_3$): δ 7.044 (t, J=53.5 Hz, 1 H), 7.207 (m, 3 H) ppm.

Step 2: Preparation of 2-(3,5-dichloro-4-(difluoromethyl)phenyl)-4,4,5,5-tetramethyl-1,3,2-dioxaborolane 4,4,4',4',5,5,5',5'-Octamethyl[2,2'-bi-1,3,2-dioxaborolane] (0.91 g, 3.56 mmol), 2,6-bis(1-methylethyl)-N-(2-pyridinylmethylene)benzenamine (0.036 g, 0.135 mmol), and bis(1,5-cyclooctadiene)diiridium dichloride (0.06 g, 0.089 mmol) were added to a solution of 1,3-dichloro-2-(difluoromethyl)benzene (1.08 g, 5.48 mmol) in heptane (18 mL). The reaction mixture turned from yellow to forest green to brick red within the first minute. The reaction mixture was refluxed for 18 h. The mixture was then partitioned between EA and water, and the aqueous extract was washed twice with EA. The organic extracts were combined, dried over $Na_2SO_4$, and concentrated under reduced pressure. The solid residue was purified by chromatography on silica gel eluted with PE-EA (8:1) to give 2-(3,5-dichloro-4-(difluoromethyl)phenyl)-4,4,5,5-tetramethyl-1,3,2-dioxaborolane (1.30 g, yield 73%) as a white solid. $^1$H NMR (500 MHz, $CDCl_3$): δ 7.678 (s, 2H), 7.061 (t, J=52.5 Hz, 1 H), 1.275 (s, 12 H) ppm.

Step 3: Preparation of 1,3-dichloro-2-(difluoromethyl)-5-(3,3,3-trifluoroprop-1-en-2-yl)benzene A mixture of 2-(3,5-dichloro-4-(difluoromethyl)phenyl)-4,4,5,5-tetramethyl-1,3,2-dioxa-borolane (0.58 g, 1.8 mmol), 2-bromo-3,3,3-trifluoroprop-1-ene (0.45 g, 2.5 mmol), $Cs_2CO_3$ (1.8 mL, 2M, 3.6 mmol) and $Pd(PPh_3)_2Cl_2$ (38 mg) in THF (10 mL) was heated at 70° C. in a sealed tube for 4 h. The mixture was cooled to rt and partitioned between ether and $H_2O$. The aqueous layer was extracted with EA and the combined organic layers were dried over $Na_2SO_4$. The solvent was removed under reduced pressure and the crude product was purified by column chromatography on silica gel eluted with hexanes to give 1,3-dichloro-2-(difluoromethyl)-5-(3,3,3-trifluoroprop-1-en-2-yl)benzene (0.33 g; yield 62%) as colorless oil. $^1$H NMR (500 MHz, $CDCl_3$): δ 7.381 (s, 2H), 7.045 (t, J=53.0 Hz, 1 H), 6.049 (s, 1 H), 5.820 (s, 1 H) ppm.

Step 4: Preparation of 5-(5-(3,5-dichloro-4(difluoromethyl)phenyl)-5-(trifluoro methyl)-4,5-dihydro-isoxazol-3-yl)-3,3-dimethyl-benzo[c][1,2]oxaborol-1(3H)-ol To a solution of crude N,1-dihydroxy-3,3-dimethyl-1,3-dihydrobenzo[c][1,2]oxaborole-5-carbimidoyl chloride (156 mg, 0.65 mmol) and 1,3-dichloro-2-(difluoromethyl)-5-(3,3,3-trifluoroprop-1-en-2-yl)benzene (210 mg, 0.72 mmol) in DMF (8 mL) at rt was added TEA (100 μL, 0.72 mmol). The reaction mixture was stirred for 12 h, poured into ice-water and extracted with EA. The organic layer was washed with brine, dried over $Na_2SO_4$, filtered and concentrated under reduced pressure. The residue was purified by prep-TLC eluted with PE-EA (3:2) and then purified by combiflash to give the title compound 5-(5-(3,5-dichloro-4(difluoromethyl)phenyl)-5-(trifluoromethyl)-4,5-dihydro-isoxazol-3-yl)-3,3-dimethyl-benzo[c][1,2]oxaborol-1(3H)-ol (90 mg; yield 28% over 3 steps) as a white solid. $^1$H NMR (500 MHz, DMSO-$d_6$): δ 9.268 (s, 1 H), 7.796 (s, 2H), 7.757-7.771 (m, 2 H), 7.694-7.710 (m, 1H), 7.389 (t, J=52.0 Hz, 1 H), 4.451 (d, J=18.0 Hz, 1 H), 4.344 (d, J=18.0 Hz, 1 H), 1.476 (s, 6 H); HPLC purity: 99.28% at 220 nm and 100% at 254 nm; MS: m/z=494.0 (M+1, ESI+).

12. 5-(5-(3,5-Dichloro-4-(trifluoromethoxy)phenyl)-5-(trifluoromethyl)-4,5-dihydro-isoxazol-3-yl)-3,3-dimethylbenzo[c][1,2]oxaborol-1(3H)-ol

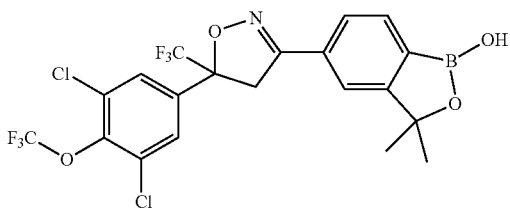 [SMILES: CC1(C)OB(O)c2ccc(C3=NOC(c4cc(Cl)c(OC(F)(F)F)c(Cl)c4)(C(F)(F)F)C3)cc21]

Step 1: Preparation of 2,6-diisopropyl-N-(pyridin-2-ylmethylene)aniline 2,6-Diisopropylaniline (2.0 g, 11.3 mmol) was added to a solution of picolinaldehyde (1.2 g, 11.3 mmol) in toluene (200 mL) in a round bottom flask equipped with a Dean-Stark trap, followed by the addition of a catalytic amount of p-toluenesulfonic acid (0.1 g). The reaction mixture was refluxed for 18 h to remove water. The reaction mixture was cooled to rt, and then washed once with water (100 mL), and the toluene was removed under reduced pressure. The resulting residue was purified by chromatography on silica gel to give the desired product (1.2 g, 40% yield) as a pale green solid.

Step 2: Preparation of 2-(3,5-dichloro-4-(trifluoromethoxy)phenyl)-4,4,5,5-tetramethyl-1,3,2-dioxaborolane 4,4,4',4',5,5,5',5'-Octamethyl-2,2'-bi(1,3,2-dioxaborolane) (1.0 g, 7.88 mmol), 2,6-diisopropyl-N-(pyridin-2-ylmethylene)aniline (40 mg, 0.15 mmol), and bis(1,5-cyclooctadiene)diiridium dichloride ($C_{16}H_{24}Cl_2Ir_2$, 61 mg, 0.10 mmol) were added to a solution of 1,3-dichloro-2-(trifluoromethoxy)benzene (1.37 g, 11.81 mmol) in n-heptane (20 mL). The reaction mixture was refluxed for 3 h. The reaction mixture was then partitioned between EA and water, and the aqueous layer extract twice with EA. The combined organic layers were washed with brine, dried over $Na_2SO_4$, filtered and concentrated under reduced pressure. The residue was purified by column chromatography to give the desired product (1.2 g, 28.5% yield) as white solid.

Step 3: Preparation of 1,3-dichloro-2-(trifluoromethoxy)-5-(3,3,3-trifluoroprop-1-en-2-yl)benzene A mixture of 2-(3,5-dichloro-4-(trifluoromethoxy)phenyl)-4,4,5,5-tetramethyl-1,3,2-dioxaborolane (1.2 g, 3.36 mmol), 2-bromo-3,3,3-trifluoroprop-1-ene (647 mg, 3.70 mmol), $K_2CO_3$ (927 mg, 6.72 mmol) and $Pd(PPh_3)_2Cl_2$ (47.2 mg, 0.067 mmol) in THF (10 mL) and $H_2O$ (6 mL) was heated at 80° C. in a sealed tube for 4 h. The mixture was cooled to rt and partitioned between EA (50 mL) and $H_2O$ (50 mL). The aqueous layer was extracted with EA (50 mL) and the combined organic layers were dried over $Na_2SO_4$. The solvent was removed under reduced pressure and the crude product was purified by column chromatography on silica gel to give the crude desired product (780 mg; 72% yield) as colorless oil.

Step 4: Preparation of 5-(5-(3,5-dichloro-4-(trifluoromethoxy)phenyl)-5-(trifluoromethyl)-4,5-dihydroisoxazol-3-yl)-3,3-dimethylbenzo[c][1,2]oxaborol-1(3H)-ol To a solution of (Z)-N,1-dihydroxy-3,3-dimethyl-1,3-dihydrobenzo[c][1,2]oxaborole-5-carbimidoyl chloride (378 mg, 1.58 mmol) and 1,3-dichloro-2-(trifluoromethoxy)-5-(3,3,3-trifluoroprop-1-en-2-yl)benzene (567 mg, 1.74 mmol) in DMF (10 mL) at rt was added TEA (176 mg, 1.74 mmol). The reaction mixture was stirred at rt for 18 h, poured into ice-water and extracted with EA (20 mL). The organic layer was washed with brine, dried over $Na_2SO_4$, filtered and concentrated under reduced pressure. The residue was purified by column chromatography to give the final desired title compound 5-(5-(3,5-dichloro-4-(trifluoromethoxy)phenyl)-5-(trifluoromethyl)-4,5-dihydroisoxazol-3-yl)-3,3-dimethylbenzo[c][1,2]oxaborol-1(3H)-ol (310 mg; 37% yield) as a white solid. $^1$H NMR (400 MHz, DMSO-$d_6$): δ 9.22 (s, 1H), 7.91 (s, 2H), 7.76 (d, J=7.6 Hz, 2H), 7.70 (d, J=8.4 Hz, 1H), 4.46 (d, J=18.4 Hz, 1H), 4.37 (d, J=18.0 Hz, 1H), 1.48 (s, 6H) ppm; HPLC purity: 97.1% at 220 nm and 99.0% at 254 nm; MS: m/z=528.4 (M+, ESI+).

13. 5-(5-(3,5-Dichlorophenyl)-5-(perfluoroethyl)-4,5-dihydroisoxazol-3-yl)-3,3-dimethylbenzo[c][1,2]oxaborol-1(3H)-ol

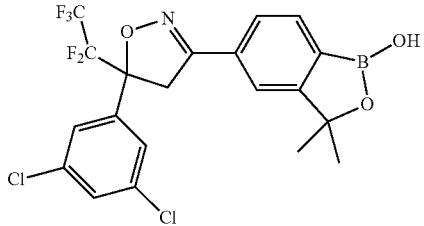 [SMILES: CC1(C)OB(O)c2ccc(C3=NOC(c4cc(Cl)cc(Cl)c4)(C(F)(F)C(F)(F)F)C3)cc21]

Step 1: Preparation of 1,3-dichloro-5-(3,3,4,4,4-pentafluorobut-1-en-2-yl)benzene A mixture of 3,5-dichlorophenylboronic acid (793 mg, 4.15 mmol), 2-bromo-3,3,4,4,4-pentafluorobut-1-ene (1.0 g, 4.57 mmol), $K_2CO_3$ (1.14 g, 8.3 mmol) and $Pd(PPh_3)_2Cl_2$ (58 mg, 0.08 mmol) in THF (4 mL) and $H_2O$ (2 mL) was heated at 80° C. in a sealed tube for 4 h. The mixture was cooled to rt and partitioned between EA (50 mL) and $H_2O$ (50 mL). The aqueous layer was extracted with EA (50 mL) and the combined organic layers were dried over $Na_2SO_4$. The solvent was removed under reduced pressure and the crude product was purified by column chromatography on silica gel to give the crude desired product (800 mg; 66% yield) as colorless oil.

Step 2: Preparation of 3,3-dimethyl-5-(5-(3,5-dichlorophenyl)-5-(perfluoroethyl)-4,5-dihydroisoxazol-3-yl)benzo[c][1,2]oxaborol-1(3H)-ol To a solution of N,1-dihydroxy-3,3-dimethyl-1,3-dihydrobenzo[c][1,2]oxaborole-5-carbimidoyl chloride (378 mg, 1.58 mmol) and 1,3-dichloro-5-(3,3,4,4,4-pentafluorobut-1-en-2-yl)benzene (506 mg, 1.74 mmol) in DMF (5 mL) at rt was added TEA (176 mg, 1.74 mmol). The reaction mixture was stirred at rt for 18 h, poured into ice-water and extracted with EA (20 mL). The organic layer was washed with brine, dried over $Na_2SO_4$, filtered and concentrated under reduced pressure. The residue was purified by column chromatography to give the final desired title compound 5-(5-(3,5-dichlorophenyl)-5-(perfluoroethyl)-4,5-dihydroisoxazol-3-yl)-3,3-dimethylbenzo[c][1,2]oxaborol-1(3H)-ol (180 mg; 23% yield) as a white solid. $^1$H NMR (400 MHz, DMSO-$d_6$): δ 9.22 (s, 1H), 7.82 (s, 2H), 7.77-7.70 (m, 3H), 7.60 (s, 1H), 4.55 (d, J=18.4 Hz, 1H), 4.32 (d, J=17.2 Hz, 1H), 1.48 (s, 6H) ppm; HPLC purity: 97.7% at 220 nm and 99.5% at 254 nm; MS: m/z=496.3 (M+, ESI+).

14. 5-(5-(3,5-Bis(trifluoromethyl)phenyl)-5-(trifluoromethyl)-4,5-dihydroisoxazol-3-yl)-3,3-dimethylbenzo[c][1,2]oxaborol-1(3H)-ol

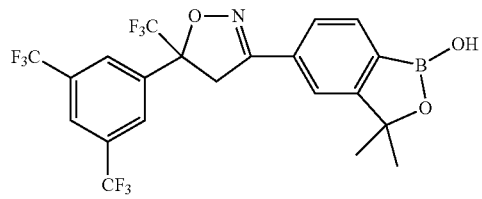 [SMILES: CC1(C)OB(O)c2ccc(C3=NOC(c4cc(C(F)(F)F)cc(C(F)(F)F)c4)(C(F)(F)F)C3)cc21]

Step 1: Preparation of 1,3-bis(trifluoromethyl)-5-(3,3,3-trifluoroprop-1-en-2-yl)benzene

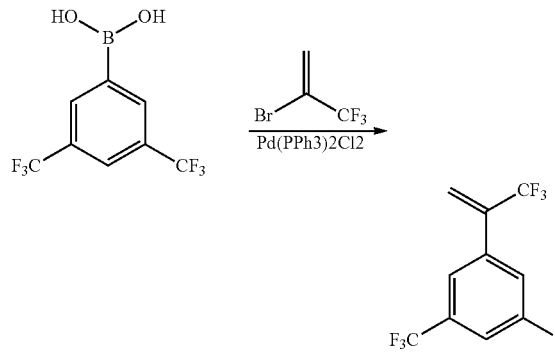

A mixture of 3,5-bis(trifluoromethyl)phenylboronic acid (2.2 g, 8.5 mmol), 2-bromo-3,3,3-trifluoroprop-1-ene (1.79 g, 10.2 mmol), Pd(PPh$_3$)$_2$Cl$_2$ (179 mg, 0.26 mmol), $K_2CO_3$ (2.35 g, 17 mmol), and Cu$_2$O (37 mg, 0.26 mmol) in THF (6 mL) and $H_2O$ (3 mL) in a tube sealed under $N_2$ was heated at 80° C. for 4 h, cooled to rt and partitioned between EA and water, extracted with EA (3×20 mL). The combined organic layer was washed with brine, dried over $Na_2SO_4$, filtered and concentrated under reduced pressure. The residue was purified by column chromatography over silica gel eluted with PE to afford 1,3-bis(trifluoromethyl)-5-(3,3,3-trifluoroprop-1-en-2-yl)benzene (1.5 g, yield 55%) as oil.

Step 2: Preparation of 5-(4-(3,5-bis(trifluoromethyl)phenyl)-4-(trifluoromethyl)-4,5-dihydro-isoxazol-5-yl)-3,3-dimethylbenzo[c][1,2]oxaborol-1(3H)-ol

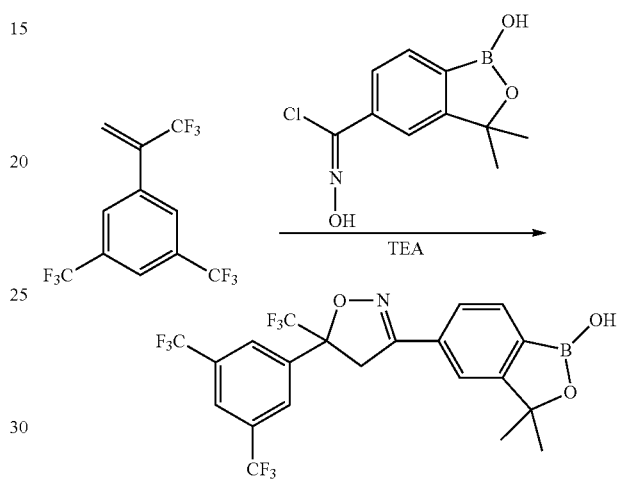

To a mixture of 1,3-bis(trifluoromethyl)-5-(3,3,3-trifluoroprop-1-en-2-yl)benzene (400 mg, 1.67 mmol), N,1-dihydroxy-3,3-dimethyl-1,3-dihydrobenzo[c][1,2]oxaborole-5-carbimidoyl chloride (770 mg, 2.51 mmol) in DMF (3 mL) was added TEA (169 mg, 1.67 mmol). The mixture was stirred at rt for 12 h, quenched with water, extracted with EA (3×20 mL). The combined organic layer was washed with brine, dried over $Na_2SO_4$, filtered and concentrated under reduced pressure. The residue was purified by prep-HPLC to afford 5-(4-(3,5-bis(trifluoromethyl)phenyl)-4-(trifluoromethyl)-4,5-dihydroisoxazol-5-yl)-3,3-dimethylbenzo[c][1,2]oxaborol-1(3H)-ol (200 mg, yield 26%) as solid. $^1$H NMR (400 MHz, DMSO-$d_6$): δ 9.22 (s, 1 H), 8.35 (s, 1 H), 8.21 (s, 1 H), 7.77 (s, 1 H), 7.75 (s, 1H), 7.72 (s, 1H), 4.58-4.42 (q, J=18 Hz, 2H), 1.48 (s, 6 H) ppm; MS: m/z=512.5 (M+1, ESI+).

15. 5-(5-(3,5-Dichloro-4-(2,2,2-trifluoroethoxy)phenyl)-5-(trifluoromethyl)-4,5-dihydroisoxazol-3-yl)-3,3-dimethylbenzo[c][1,2]oxaborol-1(3H)-ol

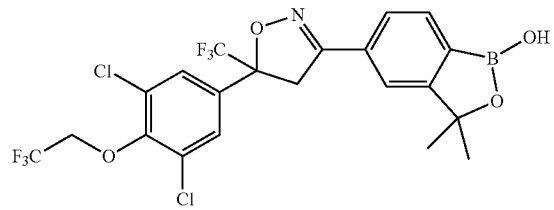 [SMILES: CC1(C)OB(O)c2ccc(C3=NOC(c4cc(Cl)c(OCC(F)(F)F)c(Cl)c4)(C(F)(F)F)C3)cc21]

Step 1: Preparation of 1,3-dichloro-2-iodo-5-nitrobenzene

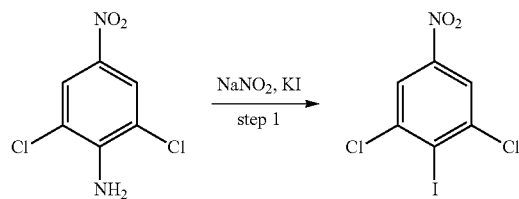 [SMILES: Nc1c(Cl)cc([N+](=O)[O-])cc1Cl ; O=[N+]([O-])c1cc(Cl)c(I)c(Cl)c1]

2,6-Dichloro-4-nitroaniline (20.0 g, 97.7 mmol) was reacted with NaNO₂ in HCl (6N) at 0° C. Then the mixture was added to aqueous KI solution. The crude product was purified by column chromatography over silica gel eluted with PE to give the desired product (12.0 g, 33% yield) as pale yellow solid.

Step 2: Preparation of 1,3-dichloro-5-nitro-2-(2,2,2-trifluoroethoxy)benzene

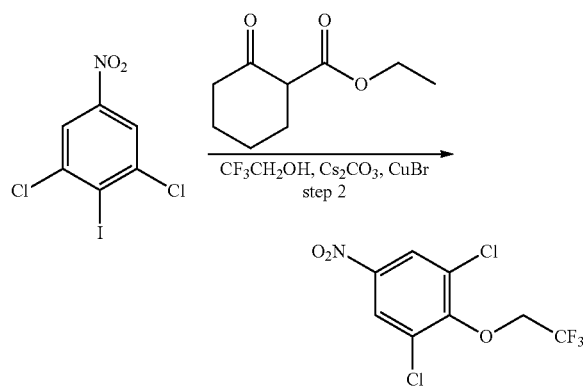

A Mixture of Cs₂CO₃ (17.22 g, 52.84 mmol), CuBr (361 mg, 2.52 mmol) and ethyl 2-oxocyclohexanecarboxylate (856 mg, 5.03 mmol) in DMSO (30 mL) under N₂ was stirred for 0.5 h at rt. Then a solution of 1,3-dichloro-2-iodo-5-nitrobenzene (8.0 g, 25.16 mmol) and 2,2,2-trifluoroethanol (3.02 g, 30.19 mmol) in DMSO (20 mL) was added to it. The reaction mixture was stirred at 80° C. for 18 h and cooled to room temperature, and then directly passed through celite. After rinsed with 250 ml of EA, the combined filter was washed by brine, dried over anhydrous Na₂SO₄, concentrated under reduced pressure. The residue was purified by column chromatography over silica gel eluted with PE:EA (100:1) to provide 1,3-dichloro-5-nitro-2-(2,2,2-trifluoroethoxy)benzene (1.93 g, yield 12.6%) as pale yellow solid.

Step 3: Preparation of 3,5-dichloro-4-(2,2,2-trifluoroethoxy)aniline

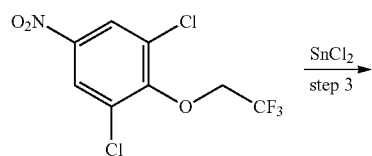

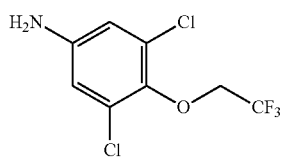

To a solution of 1,3-dichloro-5-nitro-2-(2,2,2-trifluoroethoxy)benzene (1.90 g, 6.55 mmol) in MeOH (20 mL) and 12 N HCl (20 mL) at rt, SnCl₂ (3.72 g, 19.66 mmol) was slowly added to it and then the reaction mixture was stirred overnight at rt. To the reaction mixture was slowly added 3N NaOH to pH=10 and then extracted with EA. The combined organic layers were washed with brine, dried over anhydrous Na₂SO₄, and concentrated under reduced pressure. The residue was purified by column chromatography over silica gel eluted with PE:EA (6:1) to provide 3,5-dichloro-4-(2,2,2-trifluoroethoxy)aniline (1.60 g, yield 94%) as pale yellow oil.

Step 4: Preparation of 1,3-dichloro-2-(2,2,2-trifluoroethoxy)benzene

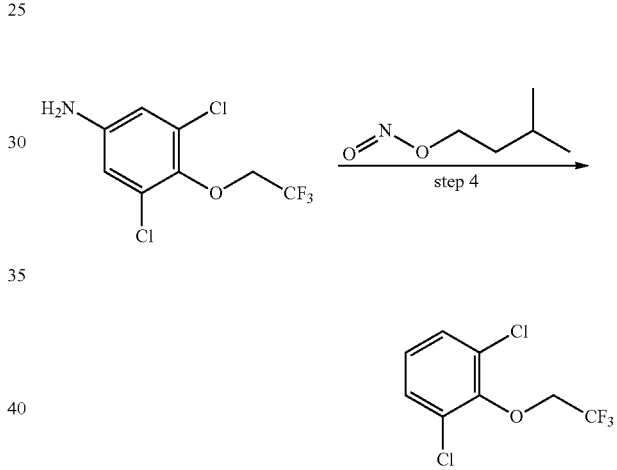

3,5-Dichloro-4-(2,2,2-trifluoroethoxy)aniline (1.60 g, 6.15 mmol) in THF (20 mL) was added isopentyl nitrite (2.94 g, 17.22 mmol) dropwise. The resulting solution was refluxed for 6 h and the solvent was removed under reduced pressure. The residue was purified by column chromatography over silica gel eluted with PE to provide 1,3-dichloro-2-(2,2,2-trifluoroethoxy)benzene as colorless oil.

Step 5: Preparation of 2-(3,5-dichloro-4-(2,2,2-trifluoroethoxy)phenyl)-4,4,5,5-tetramethyl-1,3,2-dioxaborolane

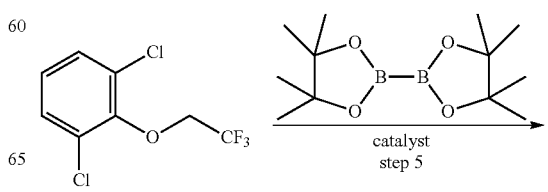

-continued

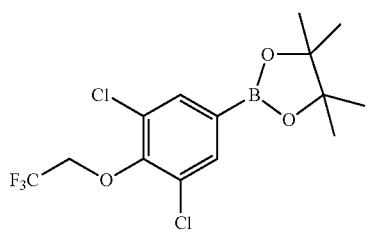

4,4,4',4',5,5,5',5'-Octamethyl-2,2'-bi(1,3,2-dioxaborolane) (925 mg, 3.65 mmol), 2,6-diisopropyl-N-(pyridin-2-ylmethylene)aniline (36.5 mg, 0.137 mmol), and bis(1,5-cyclooctadiene)-diiridium dichloride ($C_{16}H_{24}Cl_2Ir_2$, 61.3 mg, 0.091 mmol) were added to a solution of 1,3-dichloro-2-(2,2,2-trifluoroethoxy)benzene (1.34 g, 2.35 mmol) in n-heptane (30 mL). The reaction mixture was refluxed for 3 h. The reaction mixture was then partitioned between EA and water, and the aqueous layer was extracted twice with EA. The combined organic layers were washed with brine, dried over $Na_2SO_4$, filtered and concentrated under reduced pressure. The residue was purified by column chromatography over silica gel eluted with PE:EA (100:1) to give 2-(3,5-dichloro-4-(2,2,2-trifluoroethoxy)phenyl)-4,4,5,5-tetramethyl-1,3,2-dioxaborolane (530 mg, yield 39.2%) as white solid.

Step 6: Preparation of 1,3-dichloro-2-(2,2,2-trifluoroethoxy)-5-(3,3,3-trifluoroprop-1-en-2-yl)benzene

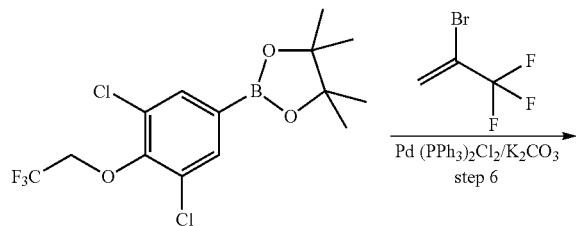

A mixture of 2-(3,5-dichloro-4-(2,2,2-trifluoroethoxy)phenyl)-4,4,5,5-tetramethyl-1,3,2-dioxaborolane (530 mg, 1.43 mmol), 2-bromo-3,3,3-trifluoroprop-1-ene (275 mg, 1.57 mmol), $K_2CO_3$ (395 mg, 2.86 mmol) and $Pd(PPh_3)_2Cl_2$ (20 mg, 0.029 mmol) in THF (3 mL) and $H_2O$ (3 mL) was heated at 80° C. in a sealed tube for 3 h. The mixture was cooled to rt and partitioned between EA (50 mL) and $H_2O$ (50 mL). The aqueous layer was extracted with EA (50 mL) and the combined organic layers were dried over $Na_2SO_4$. The solvent was removed under reduced pressure and the crude product was purified by column chromatography on silica gel eluted with PE to give 1,3-dichloro-2-(2,2,2-trifluoroethoxy)-5-(3,3,3-trifluoroprop-1-en-2-yl)benzene (360 mg; yield 74%) as colorless oil.

Step 7: Preparation of 5-(5-(3,5-dichloro-4-(2,2,2-trifluoroethoxy)phenyl)-5-(trifluoromethyl)-4,5-dihydroisoxazol-3-yl)-3,3-dimethylbenzo[c][1,2]oxaborol-1(3H)-ol

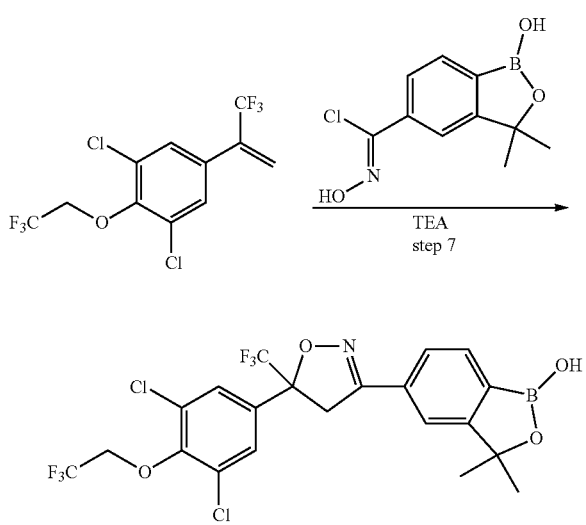 [SMILES: C=C(c1cc(Cl)c(OCC(F)(F)F)c(Cl)c1)C(F)(F)F ; CC1(C)OB(O)c2ccc(/C(Cl)=N/O)cc21 ; CC1(C)OB(O)c2ccc(C3=NOC(c4cc(Cl)c(OCC(F)(F)F)c(Cl)c4)(C(F)(F)F)C3)cc21]

To a solution of (Z)-N,1-dihydroxy-3,3-dimethyl-1,3-dihydrobenzo[c][1,2]oxaborole-5-carbimidoyl chloride (253 mg, 1.06 mmol) and 1,3-dichloro-2-(2,2,2-trifluoroethoxy)-5-(3,3,3-trifluoroprop-1-en-2-yl)benzene (360 mg, 1.06 mmol) in DMF (10 mL) at rt was added TEA (107 mg, 1.06 mmol). The reaction mixture was stirred at rt for 18 h, poured into ice-water and extracted with EA (20 mL). The organic layer was washed with brine, dried over $Na_2SO_4$, filtered and concentrated under reduced pressure. The residue was purified by column chromatography over silica gel eluted with PE:EA (6:1) to give the final title compound (105 mg; yield 18.3%) as a white solid. $^1$H NMR (400 MHz, DMSO-$d_6$): δ 9.20 (s, 1H), 7.76-7.69 (m, 5H), 4.80 (q, J=8.8 Hz, 2H), 4.37 (q, J=18.4 Hz, 2H), 1.48 (s, 6H) ppm; HPLC purity: 96.2% at 220 nm and 98.3% at 254 nm; MS: m/z=542.2 (M+, ESI+).

16. 3,3-Dimethyl-5-(5-methyl-5-(3,4,5-trichlorophenyl)-4,5-dihydroisoxazol-3-yl)benzo[c][1,2]oxaborol-1(3H)-ol

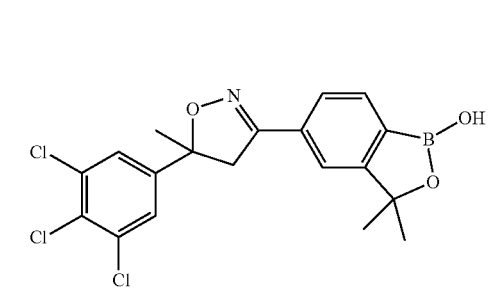 [SMILES: CC1(C)OB(O)c2ccc(C3=NOC(C)(c4cc(Cl)c(Cl)c(Cl)c4)C3)cc21]

Step 1: Preparation of 1,2,3-trichloro-5-(prop-1-en-2-yl)benzene

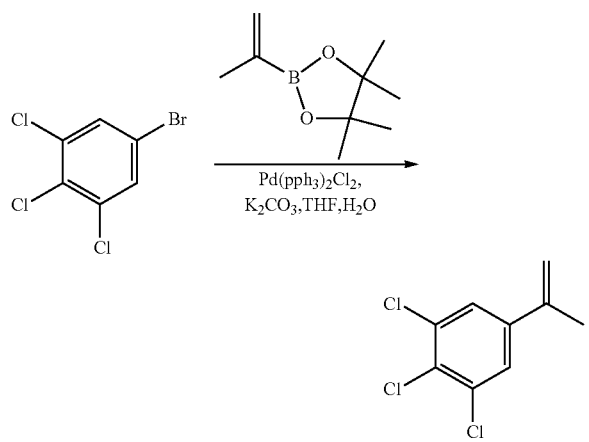

To a mixture of 5-bromo-1,2,3-trichlorobenzene (3.64 g, 14 mmol), 4,4,5,5-tetramethyl-2-(prop-1-en-2-yl)-1,3,2-dioxaborolane (2.5 g, 15 mmol) and Pd(PPh$_3$)$_2$Cl$_2$ (983 mg, 1.4 mmol) in THF (50 ml) and H$_2$O (5 ml) at rt was added K$_2$CO$_3$ (5.8 g, 42 mmol). The mixture was refluxed overnight and then concentrated under reduced pressure. The residue was purified by column chromatography over silica gel eluted with PE:EA (5:1 to 2:1) to give the desired intermediate (2.5 g, yield 81%) as a yellow oil: $^1$H NMR (300 MHz, CDCl$_3$): δ 7.44 (s, 2H), 5.39 (s, 1H), 5.19-5.18 (t, 1H), 2.10 (s, 3H) ppm.

Step 2: Preparation of 3,3-dimethyl-5-(5-methyl-5-(3,4,5-trichlorophenyl)-4,5-dihydroisoxazol-3-yl)benzo[c][1,2]oxaborol-1(3H)-ol

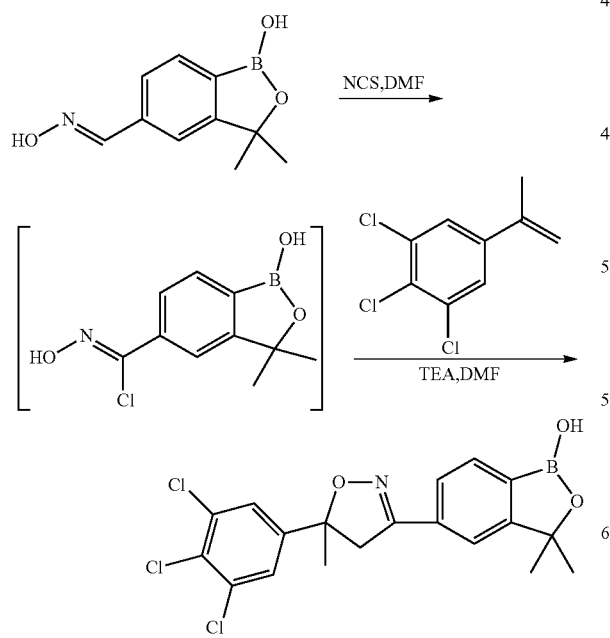

To a solution of (E)-1-hydroxy-3,3-dimethyl-1,3-dihydrobenzo[c][1,2]oxaborole-5-carbaldehyde oxime (500 mg, 2.44 mmol) in DMF (10 mL) at rt was added NCS (392 mg, 2.93 mmol). The reaction mixture was warmed to 45° C., stirred for 2.5 h and cooled to rt. To a solution of 1,2,3-trichloro-5-(prop-1-en-2-yl)benzene (277 mg, 1.26 mmol) and TEA (140.4 mg, 1.39 mmol) in DMF (15 mL) was added the above mixture dropwise at 0° C. The mixture was stirred at this temperature for 1 h and then at rt overnight. The mixture was acidified with HCl (3 N) to pH of 2 and then poured into water followed by extraction with EA (100 ml×2). The combined organic layers were washed with brine, dried over Na$_2$SO$_4$, filtered and concentrated under reduced pressure. The residue was purified by prep-TLC eluted with PE:EA (2:1) to give the final title compound (200 mg, yield 37.5%) as a white solid: $^1$H NMR (300 MHz, DMSO-d$_6$): δ 9.14 (s, 1H), 7.73-7.62 (m, 5H), 3.79-3.63 (q, 2H), 1.75 (s, 3 H), 1.46 (s, 6H). MS: m/z=424 [M+H]+.

17. (S)-3,3-Dimethyl-5-(5-(3,4,5-trichlorophenyl)-5-(trifluoromethyl)-4,5-dihydroisoxazol-3-yl)benzo[c][1,2]oxaborol-1(3H)-ol

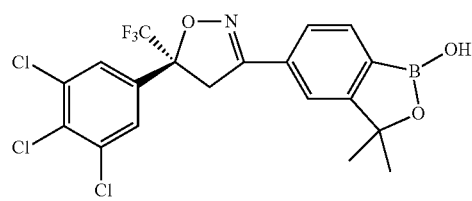 [SMILES: CC1(C)OB(O)c2ccc(C3=NO[C@@](c4cc(Cl)c(Cl)c(Cl)c4)(C(F)(F)F)C3)cc21]

The title compound was obtained by separation of the racemic mixture of 3,3-dimethyl-5-(5-(3,4,5-trichlorophenyl)-5-(trifluoromethyl)-4,5-dihydroisoxazol-3-yl)benzo[c][1,2]oxaborol-1(3H)-ol with chiral column chromatography. The racemic mixture was dissolved in the solvent of mobile phase and separated by supercritical fluid (SFC) chiral chromatography. The chromatography conditions used were: column CHIRALCEL OJ-H (column size: 0.46 cm I.D.×15 cm length), mobile phase CO$_2$/MeOH=70/30 (w/w), flow rate 2.0 mL/min, detector wave length UV 220 nm, and temperature 35° C.

18. (R)-3,3-Dimethyl-5-(5-(3,4,5-trichlorophenyl)-5-(trifluoromethyl)-4,5-dihydroisoxazol-3-yl)benzo[c][1,2]oxaborol-1(3H)-ol

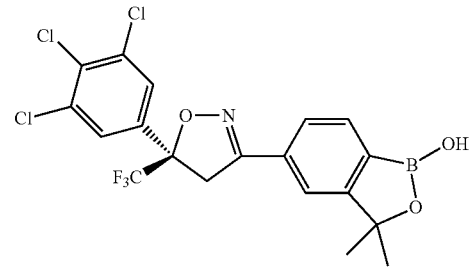 [SMILES: CC1(C)OB(O)c2ccc(C3=NO[C@](c4cc(Cl)c(Cl)c(Cl)c4)(C(F)(F)F)C3)cc21]

The title compound was obtained by separation of the racemic mixture of 3,3-dimethyl-5-(5-(3,4,5-trichlorophenyl)-5-(trifluoromethyl)-4,5-dihydroisoxazol-3-yl)benzo[c][1,2]oxaborol-1(3H)-ol with chiral column chromatography. The racemic mixture was dissolved in the solvent of mobile phase and separated by supercritical fluid (SFC) chiral chromatography. The chromatography conditions used were: column CHIRALCEL OJ-H (column size: 0.46 cm I.D.×15 cm length), mobile phase $CO_2$/MeOH=70/30 (w/w), flow rate 2.0 mL/min, detector wave length UV 220 nm, and temperature 35° C.

19. 5-(5-(3-Chloro-4-fluorophenyl)-5-(trifluoromethyl)-4,5-dihydroisoxazol-3-yl)-3,3-dimethylbenzo[c][1,2]oxaborol-1(3H)-ol

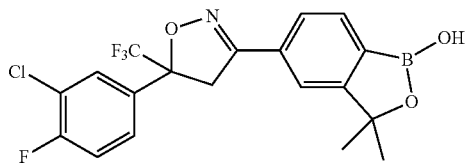 [SMILES: CC1(C)OB(O)c2ccc(C3=NOC(c4ccc(F)c(Cl)c4)(C(F)(F)F)C3)cc21]

Step 1: Preparation of 2-chloro-1-fluoro-4-(3,3,3-trifluoroprop-1-en-2-yl)benzene

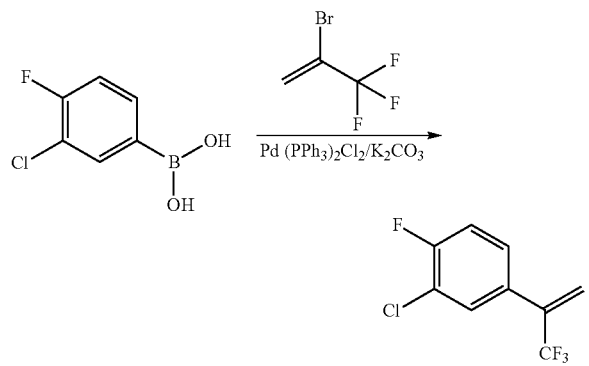

A mixture of (3-chloro-4-fluorophenyl) boronic acid (300 mg, 1.72 mmol), 2-bromo-3,3,3-trifluoroprop-1-ene (331 mg, 1.89 mmol), $K_2CO_3$ (474 mg, 3.44 mmol) and $Pd(PPh_3)_2Cl_2$ (25 mg, 0.035 mmol) in THF (2 mL) and $H_2O$ (1 mL) was heated at 80° C. in a sealed tube for 3 h. The mixture was cooled to rt and partitioned between EA (20 mL) and $H_2O$ (20 mL). The aqueous layer was extracted with EA (20 mL) and the combined organic layers were dried over $Na_2SO_4$. The solvent was removed under reduced pressure and the crude product was purified by column chromatography on silica gel elute with PE to give 2-chloro-1-fluoro-4-(3,3,3-trifluoroprop-1-en-2-yl)benzene (240 mg, 62.3% yield) as colorless oil.

Step 2: Preparation of 5-(5-(3-chloro-4-fluorophenyl)-5-(trifluoromethyl)-4,5-dihydroisoxazo-1-3-yl)-3,3-dimethylbenzo[c][1,2]oxaborol-1(3H)-ol

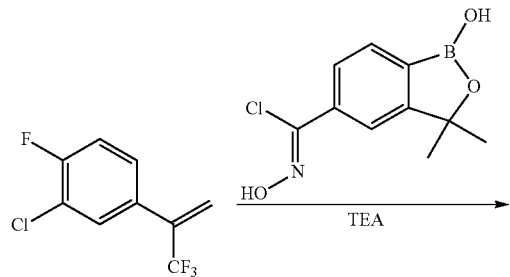

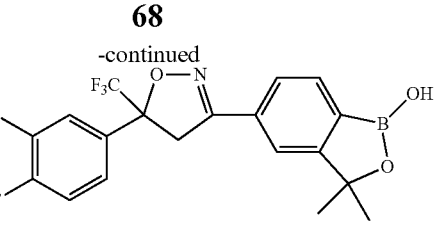

To a solution of (Z)-N,1-dihydroxy-3,3-dimethyl-1,3-dihydrobenzo[c][1,2]oxaborole-5-carbimidoyl chloride (239 mg, 1.0 mmol) and 2-chloro-1-fluoro-4-(3,3,3-trifluoroprop-1-en-2-yl)benzene (240 mg, 1.07 mmol) in DMF (5 mL) at rt was added TEA (108 mg, 1.07 mmol). The reaction mixture was stirred at rt for 18 h, poured into ice-water and extracted with EA (20 mL). The organic layer was washed with brine, dried over $Na_2SO_4$, filtered and concentrated under reduced pressure. The residue was purified by column chromatography over silica gel eluted with PE:EA (6:1) to give the final title compound 5-(5-(3-chloro-4-fluorophenyl)-5-(trifluoromethyl)-4,5-dihydroisoxazol-3-yl)-3,3-dimethylbenzo[c][1,2]oxaborol-1(3H)-ol (140 mg; yield 30.6%) as a white solid. $^1$H NMR (400 MHz, DMSO-$d_6$): δ 9.21 (s, 1H), 7.80-7.70 (m, 4H), 7.64-7.60 (m, 2H), 4.43 (d, J=18.4 Hz, 1H), 4.27 (d, J=18.4 Hz, 1H), 1.48 (s, 6H) ppm; HPLC purity: 96.0% at 220 nm and 96.4% at 254 nm; MS: m/z=428.1 (M+, ESI+).

20. 5-(5-(Fluoromethyl)-5-(3,4,5-trichlorophenyl)-4,5-dihydroisoxazol-3-yl)-3,3-dimethylbenzo[c][1,2]oxaborol-1(3H)-ol

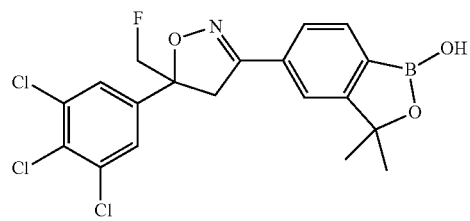 [SMILES: CC1(C)OB(O)c2ccc(C3=NOC(CF)(c4cc(Cl)c(Cl)c(Cl)c4)C3)cc21]

Step 1: Preparation of 1,2,3-trichloro-5-(3-fluoroprop-1-en-2-yl)benzene

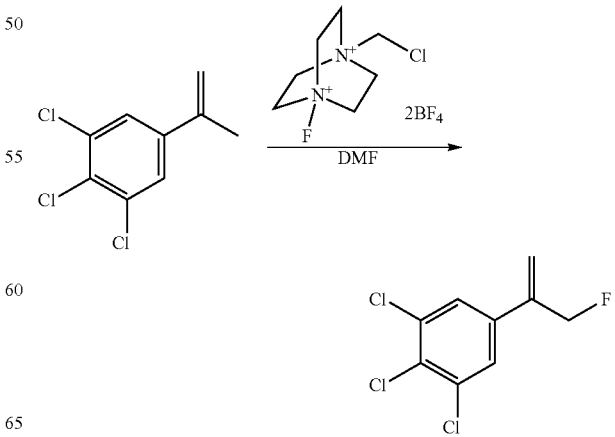

To a mixture of 1,2,3-trichloro-5-(prop-1-en-2-yl)benzene (660 mg, 3 mmol) and 1-(chloromethyl)-4-fluoro-1,4-diazabicyclo[2.2.2]octane-1,4-diium bis(tetrafluoroborate) (1.115 g, 3.15 mmol) in DMF (25 ml). The mixture was stirred at 75° C. for 3 h. The mixture was washed with H₂O and extracted with EA (30 ml×2). The mixture was concentrated under reduced pressure. The residue was purified by column chromatography over silica gel eluted with PE:EA (7:1 to 5:1) to give the desired product (260 mg, yield 36%).

Step 2: Preparation of 5-(5-(fluoromethyl)-5-(3,4,5-trichlorophenyl)-4,5-dihydroisoxazol-3-yl)-3,3-dimethylbenzo[c][1,2]oxaborol-1(3H)-ol

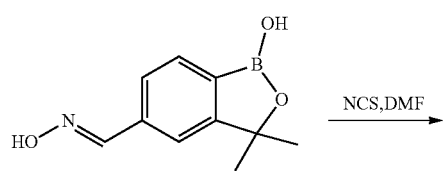

To a solution of (E)-1-hydroxy-3,3-dimethyl-1,3-dihydrobenzo[c][1,2]oxaborole-5-carbaldehyde oxime (225.5 mg, 1.1 mmol) in DMF (10 mL) at rt was added NCS (177 mg, 1.32 mmol). The reaction mixture was warmed to 45° C., stirred for 2.5 h and cooled to rt. To a solution of 1,2,3-trichloro-5-(3-fluoroprop-1-en-2-yl)benzene (260 mg, 1.1 mmol) and TEA (122.2 mg, 1.21 mmol) in DMF (20 mL) was added the above mixture dropwise at 0° C. The mixture was stirred at this temperature for 1 h and then at rt overnight. The mixture was acidified with HCl (3 N) to pH of 2 and then poured into water followed by extraction with EA (100 ml×2). The combined organic layers were washed with brine, dried over Na₂SO₄, filtered and concentrated under reduced pressure. The residue was purified by prep-TLC eluted with PE:EA (2:1) to give the final title compound (200 mg, yield 41%) as a white solid: ¹H NMR (300 MHz, DMSO-d₆): δ 9.14 (s, 1H), 7.77 (s, 2H), 7.69-7.68 (m, 3H), 4.91 (s, 1H), 4.75 (s, 1H), 3.80 (s, 2H), 1.45 (s, 6H). MS: m/z=443 [M+H]+.

21. 5-(5-(4-Bromo-3,5-dichlorophenyl)-5-(trifluoromethyl)-4,5-dihydroisoxazol-3-yl)-3,3-dimethylbenzo[c][1,2]oxaborol-1(3H)-ol

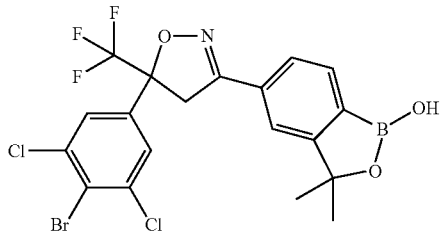 [SMILES: CC1(C)OB(O)c2ccc(C3=NOC(c4cc(Cl)c(Br)c(Cl)c4)(C(F)(F)F)C3)cc21]

Step 1: Preparation of 2-(4-bromo-3,5-dichlorophenyl)-4,4,5,5-tetramethyl-1,3,2-dioxaborolane

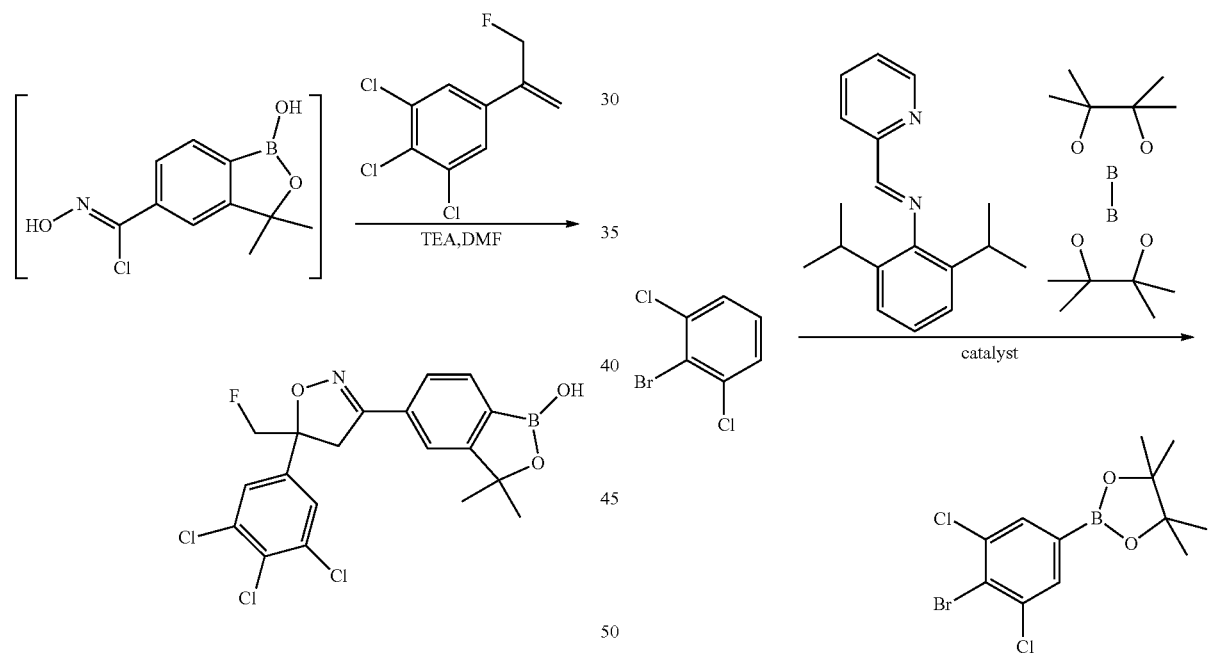

4,4,4',4',5,5,5',5'-Octamethyl[2,2'-bi-1,3,2-dioxaborolane] (4.88 g, 19.2 mmol), 2,6-bis(1-methylethyl)-N-(2-pyridinylmethylene)benzenamine (0.195 g, 0.73 mmol), and bis(1,5-cyclooctadiene)diiridium(I) dichloride (0.32 g, 0.48 mmol) were added to a solution of 1,3-dichloro-2-bromobenzene (6.6 g, 29.5 mmol) in heptane (10 mL). The reaction mixture color changed from yellow to forest green to brick red within the first minute. The reaction mixture was refluxed for 18 h. The mixture was then partitioned between EA and water, and the aqueous extract was washed twice with EA. The organic extracts were combined, dried over Na₂SO₄, and concentrated under reduced pressure. The solid residue was purified by column chromatography over silica gel eluted with PE-EA (8:1) to give 2-(3,5-dichloro-4-(bromo)phenyl)-

4,4,5,5-tetramethyl-1,3,2-dioxaborolane (7 g, yield 68%) as a white solid. ¹H NMR (400 MHz, CDCl₃): δ 7.75 (s, 2H), 1.34 (s, 12H) ppm.

Step 2: Preparation of 2-bromo-1,3-dichloro-5-(3,3,3-trifluoroprop-1-en-2-yl)benzene

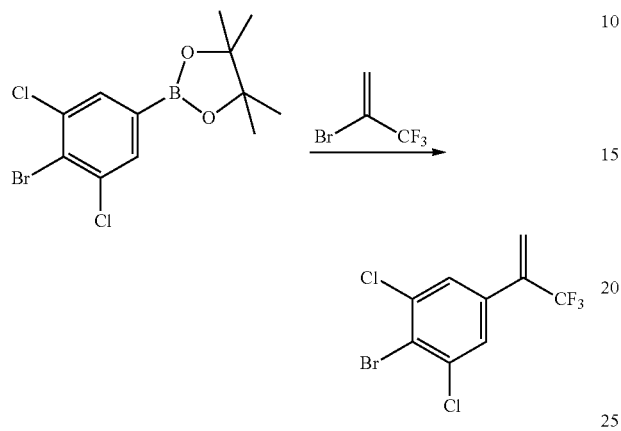

A mixture of 2-(3,5-dichloro-4-(bromo)phenyl)-4,4,5,5-tetramethyl-1,3,2-dioxaborolane (1 g, 2.86 mmol), 2-bromo-3,3,3-trifluoroprop-1-ene (0.60 g, 3.43 mmol), Cs₂CO₃ (2.86 mL, 2M, 5.72 mmol) and Pd(PPh₃)₂Cl₂ (60 mg) in THF (30 mL) was heated at 70° C. in a sealed tube for 4 h. The mixture was cooled to rt and partitioned between ether and H₂O. The aqueous layer was extracted with EA and the combined organic layers were dried over Na₂SO₄. The solvent was removed under reduced pressure and the crude product was purified by column chromatography over silica gel eluted with hexanes to give 1,3-dichloro-2-(trifluoromethyl)-5-(3,3,3-trifluoro-prop-1-en-2-yl)benzene (0.6 g; yield 66.7%) as colorless oil. ¹H NMR (400 MHz, DMSO-d₆): δ 7.72 (s, 2H), 6.38 (s, 1 H), 6.28 (s, 1 H) ppm.

Step 3: Preparation of 5-(5-(4-bromo-3,5-dichlorophenyl)-5-(trifluoromethyl)-4,5-dihydro-isoxazol-3-yl)-3,3-dimethylbenzo[c][1,2]oxaborol-1(3H)-ol

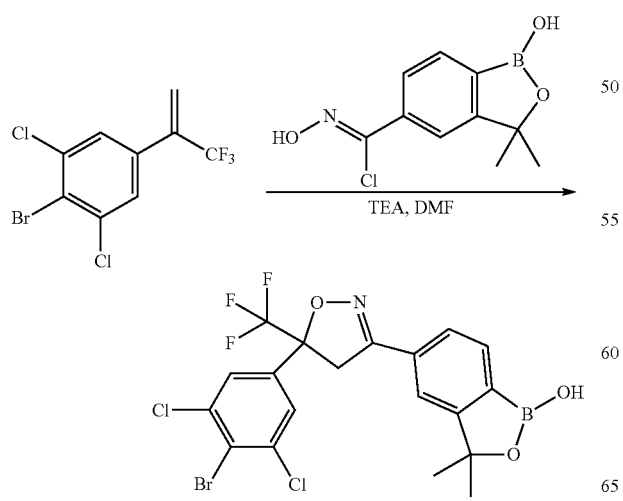

To a solution of N,1-dihydroxy-3,3-dimethyl-1,3-dihydrobenzo[c][1,2]oxaborole-5-carbimidoyl chloride (0.25 g, 1.04 mmol) and 1,3-dichloro-2-(trifluoromethyl)-5-(3,3,3-trifluoroprop-1-en-2-yl)benzene (400 mg, 1.26 mmol) in DMF (10 mL) at rt was added TEA (0.43 mL, 3.12 mmol). The reaction mixture was stirred for 12 h, poured into ice-water and extracted with EA. The organic layer was washed with brine, dried over Na₂SO₄, filtered and concentrated under reduced pressure. The residue was purified by prep-TLC eluted with PE-EA (3:2) and then purified by prep-TLC to give the title compound (126 mg, yield 19.2%) as a white solid. ¹H NMR (400 MHz, DMSO-d₆): δ 9.29 (s, 1 H), 7.80-7.69 (m, 5 H), 4.45 (d, J=18.4 Hz, 1 H), 4.35 (d, J=18.4 Hz, 1 H), 1.48 (s, 3H), 1.47 (s, 3H) ppm; HPLC purity: 95.4% at 214 nm and 98.7% at 254 nm MS: m/z=582 (M-1, ESI-).

22. 5-(5-(3,5-Dichloro-4-methoxyphenyl)-5-(trifluoromethyl)-4,5-dihydroisoxazol-3-yl)-3,3-dimethyl-benzo[c][1,2]oxaborol-1(3H)-ol

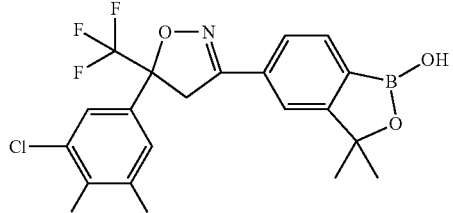

Step 1: Preparation of 4-bromo-2,6-dichlorophenol

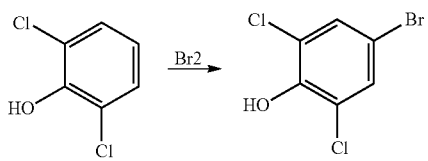

A stirred solution of 2,6-dichlorophenol (20 g, 123.4 mmol) in acetonitrile (200 mL) was cooled to 0° C. and bromine (23.7 g) in acetonitrile (50 mL) was added dropwise. The red solution was stirred at 0° C. for 2 h and a saturated aqueous solution of sodium sulphite was added until the red color disappeared. The phases were separated and the aqueous phase was extracted three times with ethyl acetate. Concentration of the combined organic phases gave a yellow oil, which was purified on a silica gel column (heptane/ethyl acetate, 10:1) to give 17.8 g of 4-bromo-2,6-dichlorophenol as a white solid. Yield: 60%; ¹H NMR (400 MHz, CDCl₃): δ 7.42 (s, 2H), 5.9 (br s, 1H) ppm.

Step 2: Preparation of 5-bromo-1,3-dichloro-2-methoxybenzene

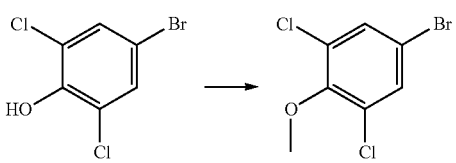

A mixture of 4-bromo-2,6-dichlorophenol (10 g, 41.67 mmol), K$_2$CO$_3$ (11.5 g, 83.3 mmol) and CH$_3$I (8.88 g, 62.5 mmol) in DMF (100 mL) was stirred at rt for 16 h. TLC (EtOAc/petroleum ether=1:2) indicated complete consumption of 4-bromo-2,6-dichlorophenol. The reaction mixture was poured into water (300 mL). The aqueous phase was extracted with EtOAc (2×100 mL). The combined organic phases were dried over anhydrous Na$_2$SO$_4$, and concentrated in vacuo to give crude 5-bromo-1,3-dichloro-2-methoxybenzene, which was purified by column chromatography (silica gel, EtOAc/petroleum ether=1:5) to yield the ether product (9 g, yield 84.9%) as a white solid. $^1$H NMR (400 MHz, CDCl$_3$): δ 7.45 (s, H), 3.91 (s, 3H) ppm.

Step 3: Preparation of 2-(3,5-dichloro-4-methoxyphenyl)-4,4,5,5-tetramethyl-1,3,2-dioxaborolane

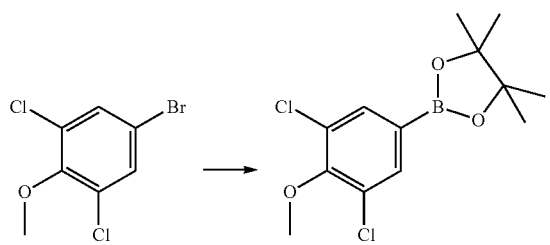 [SMILES: COc1c(Cl)cc(Br)cc1Cl ; COc1c(Cl)cc(B2OC(C)(C)C(C)(C)O2)cc1Cl]

A mixture of 5-bromo-1,3-dichloro-2-methoxybenzene (1 g, 3.94 mmol), bis(pinacolato)diboron (1.46 g, 5.83 mmol), Pd(dppf)Cl$_2$ (0.135 g, 0.19 mmol), KOAc (1.13 g, 11.6 mmol) in 1,4-dioxane (20 mL) was degassed with N$_2$ for 5 min. The reaction mixture was stirred at 70° C. for 16 h. TLC (EtOAc/Petroleum ether=1:5) indicated complete consumption of the bromo starting material. The reaction mixture was poured into water (40 mL) and extracted with EtOAc (3×70 mL). The combined organic phases were dried over anhydrous Na$_2$SO$_4$, and concentrated in vacuo to give crude product, which was purified by column chromatography (silica gel, EtOAc/petroleum ether=1:10) to get the pure boron compound (0.5 g, yield 42.4%) as a white solid. $^1$H NMR (400 MHz, CDCl$_3$): δ 7.71 (s, 2 H), 3.91 (s, 3 H), 1.33 (s, 12 H) ppm.

Step 4: Preparation of 1,3-dichloro-2-methoxy-5-(3,3,3-trifluoroprop-1-en-2-yl)benzene

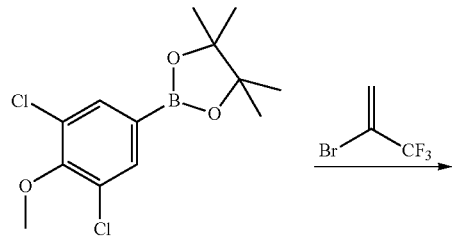

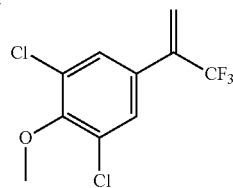

A mixture of 2-(3,5-dichloro-4-(methoxy)phenyl)-4,4,5,5-tetramethyl-1,3,2-dioxaborolane (0.4 g, 1.33 mmol), 2-bromo-3,3,3-trifluoroprop-1-ene (0.28 g, 1.59 mmol), Cs$_2$CO$_3$ (1.33 mL, 2M, 2.66 mmol) and Pd(PPh$_3$)$_2$Cl$_2$ (28 mg) in THF (30 mL) was heated at 70° C. in a sealed tube for 4 h. The mixture was cooled to rt and partitioned between ether and H$_2$O. The aqueous layer was extracted with EA and the combined organic layers were dried over Na$_2$SO$_4$. The solvent was removed under reduced pressure and the crude product was purified by column chromatography over silica gel eluted with hexanes to give 1,3-dichloro-2-(trifluoromethyl)-5-(3,3,3-trifluoro-prop-1-en-2-yl)benzene (0.2 g, yield 56%) as colorless oil. $^1$H NMR (400 MHz, CDCl$_3$): δ 7.39 (s, 2 H), 6.00 (s, 1 H), 5.78 (s, 1 H), 3.93 (s, 3 H) ppm.

Step 5: Preparation of 5-(5-(3,5-dichloro-4-methoxyphenyl)-5-(trifluoromethyl)-4,5-dihydroisoxazol-3-yl)-3,3-dimethylbenzo[c][1,2]oxaborol-1(3H)-ol

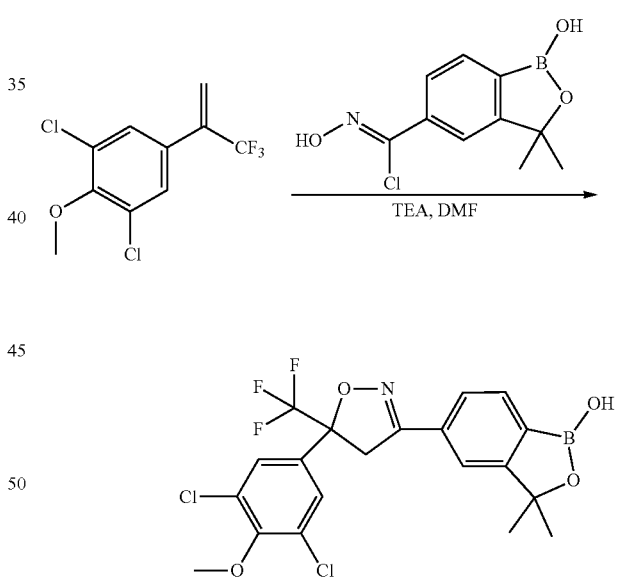

To a solution of crude compound N,1-dihydroxy-3,3-dimethyl-1,3-dihydrobenzo[c][1,2]oxa-borole-5-carbimidoyl chloride (0.29 g, 1.23 mmol) and 1,3-dichloro-2-methoxy-5-(3,3,3-trifluoroprop-1-en-2-yl)benzene (0.4 g, 1.48 mmol) in DMF (10 mL) at rt was added TEA (0.51 mL, 3.67 mmol). The reaction mixture was stirred for 12 h, poured into icewater and extracted with EA. The organic layer was washed with brine, dried over Na$_2$SO$_4$, filtered and concentrated under reduced pressure. The residue was purified by prep-TLC eluted with PE-EA (3:2) and then purified by preparative TLC to give the title compound (110 mg, yield 15.6%) as a white solid. $^1$H NMR (400 MHz, DMSO-d$_6$): δ 9.27 (s, 1 H), 7.82-7.75 (m, 5 H), 4.46 (d, J=18.4 Hz, 1 H), 4.36 (d, J=18.4 Hz, 1 H), 3.93 (s, 3 H), 1.53 (s, 6 H) ppm; MS: m/z=472 (M−1, ESI−).

23. 5-(5-(3,4-Dichlorophenyl)-5-(trifluoromethyl)-4,5-dihydroisoxazol-3-yl)-3,3-dimethyl-benzo[c][1,2]oxaborol-1(3H)-ol

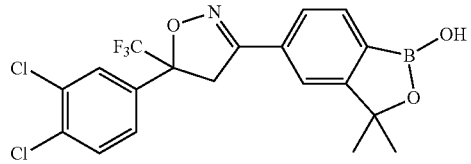

Step 1: Preparation of 1,2-dichloro-4-(3,3,3-trifluoroprop-1-en-2-yl)benzene

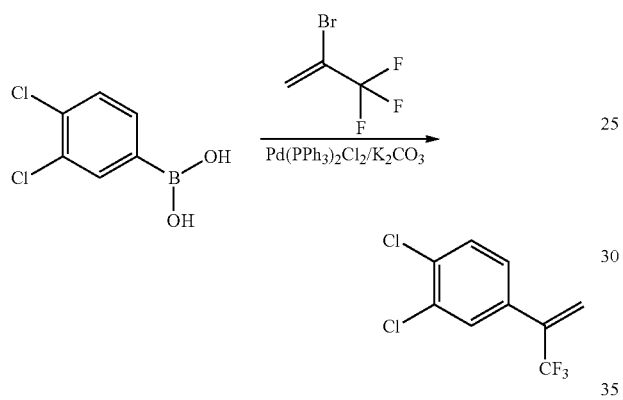

A mixture of (3,4-dichlorophenyl)boronic acid (500 mg, 2.62 mmol), 2-bromo-3,3,3-trifluoroprop-1-ene (501 mg, 2.88 mmol), $K_2CO_3$ (723 mg, 5.24 mmol) and $Pd(PPh_3)_2Cl_2$ (36 mg, 0.052 mmol) in THF (2 mL) and $H_2O$ (1 mL) was heated at 80° C. in a sealed tube for 3 hours. The mixture was cooled to rt and partitioned between EA (20 mL) and $H_2O$ (20 mL). The aqueous layer was extracted with EA (20 mL) and the combined organic layers were dried over $Na_2SO_4$. The solvent was removed under reduced pressure and the crude product was purified by column chromatography over silica gel eluted with PE to give 1,2-dichloro-4-(3,3,3-trifluoroprop-1-en-2-yl)-benzene (400 mg, 63.3% yield) as colorless oil.

Step 2: Preparation of 5-(5-(3,4-dichlorophenyl)-5-(trifluoromethyl)-4,5-dihydro-isoxazol-3-yl)-3,3-dimethylbenzo[c][1,2]oxaborol-1(3H)-ol

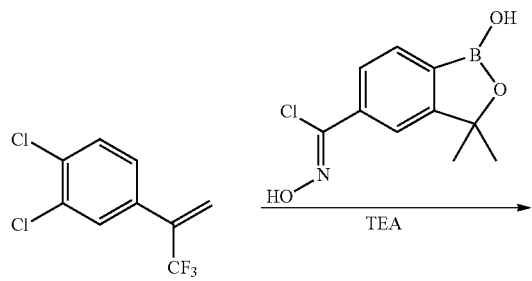

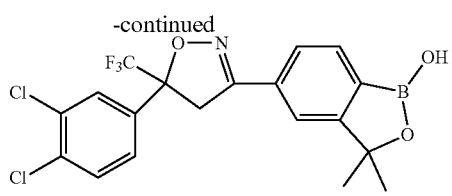

To a solution of (Z)-N,1-dihydroxy-3,3-dimethyl-1,3-dihydrobenzo[c][1,2]oxaborole-5-carbimidoyl chloride (397 mg, 1.66 mmol) and 1,2-dichloro-4-(3,3,3-trifluoroprop-1-en-2-yl)benzene (400 mg, 1.66 mmol) in DMF (5 mL) at rt was added TEA (168 mg, 1.66 mmol). The reaction mixture was stirred at rt for 18 h, poured into ice-water and extracted with EA (20 mL). The organic layer was washed with brine, dried over $Na_2SO_4$, filtered and concentrated under reduced pressure. The residue was purified by column chromatography over silica gel eluted with PE:EA (6:1) to give the final title compound 5-(5-(3,4-dichlorophenyl)-5-(trifluoromethyl)-4,5-dihydroisoxazol-3-yl)-3,3-dimethyl-benzo[c][1,2]oxaborol-1(3H)-ol (180 mg; yield 24.4%) as a white solid. $^1$H NMR (400 MHz, DMSO-$d_6$): δ 9.20 (s, 1H), 7.83-7.60 (m, 5H), 4.45 (d, J=18.8 Hz, 1H), 4.26 (d, J=18.4 Hz, 1H), 1.48 (s, 6H) ppm; HPLC purity: 96.8% at 220 nm and 97.5% at 254 nm; MS: m/z=444.3 (M+, ESI+).

24. 5-(5-(4-Fluoro-3-(trifluoromethyl)phenyl)-5-(trifluoromethyl)-4,5-dihydroisoxazol-3-yl)-3,3-dimethylbenzo[c][1,2]oxaborol-1(3H)-ol

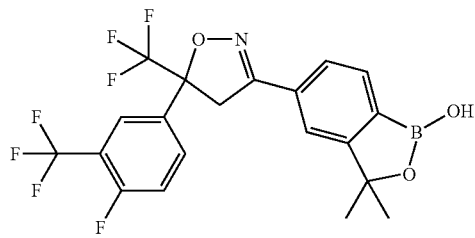 [SMILES: CC1(C)OB(O)c2ccc(C3=NOC(c4ccc(F)c(C(F)(F)F)c4)(C(F)(F)F)C3)cc21]

Step 1: Preparation of 2-(4-fluoro-3-(trifluoromethyl)phenyl)-1,3,2-dioxaborolane

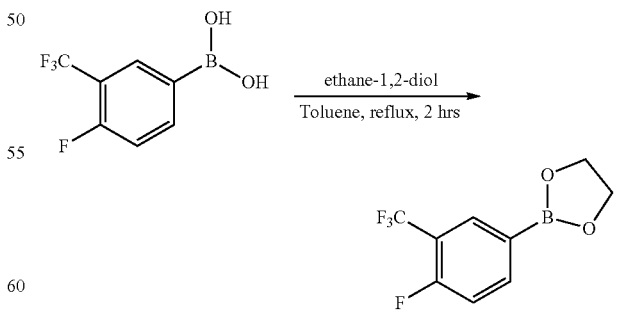

The mixture of 4-fluoro-3-(trifluoromethyl)phenylboronic acid (2.08 g, 10 mmol) and ethane-1,2-diol (3.72 g, 60 mmol) in toluene (150 ml) was refluxed with a Dean-stark trap for 2 h, then cooled to rt. The solvent was concentrated to dryness to afford the crude product (2.7 g, 100%). $^1$H NMR (300

MHz, CDCl$_3$): δ 8.08-8.05 (d, 1H), 8.01-7.96 (t, 1H), 7.24-7.17 (t, 1H), 4.40 (s, 4H) ppm.

Step 2: Preparation of 1-fluoro-2-(trifluoromethyl)-4-(3,3,3-trifluoroprop-1-en-2-yl)benzene

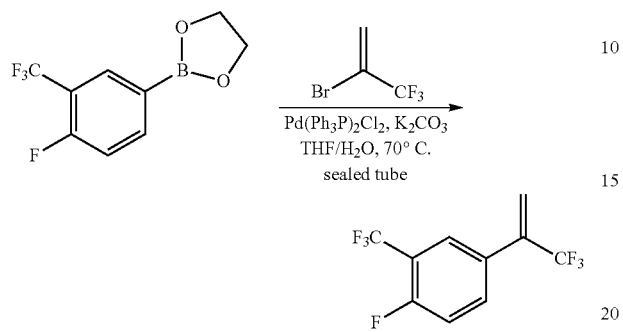

The mixture of 2-(4-fluoro-3-(trifluoromethyl)phenyl)-1,3,2-dioxaborolane (2.34 g, 10 mmol), 2-bromo-3,3,3-trifluoroprop-1-ene (2.10 g, 12 mmol), Pd(Ph$_3$P)$_2$Cl$_2$ (0.281 g, 0.4 mmol) and K$_2$CO$_3$ (2.76 g, 20 mmol) in THF (30 mL) and H$_2$O (15 mL) was heated at 70° C. overnight. Then the reaction mixture was cooled down to rt, added water and extracted with ethyl acetate, washed with brine, dried with Na$_2$SO$_4$, concentrated to dryness to afford the crude product. It was further purified by column chromatography eluted with PE to afford the desired product (0.6 g, yield 23.3%) as light yellow oil. $^1$H NMR (300 MHz, CDCl$_3$): δ 7.69-7.62 (m, 2H), 7.27-7.21 (t, 1H), 6.05 (d, 1H), 5.80 (d, 1H) ppm.

Step 3: Preparation of 5-(5-(4-fluoro-3-(trifluoromethyl)phenyl)-5-(trifluoromethyl)-4,5-dihydroisoxazol-3-yl)-3,3-dimethylbenzo[c][1,2]oxaborol-1(3H)-ol

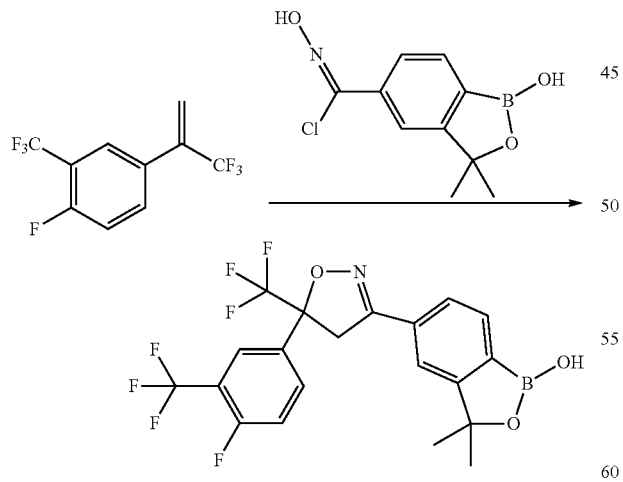

To a solution of (Z)-N,1-dihydroxy-3,3-dimethyl-1,3-dihydrobenzo[c][1,2]oxaborole-5-carbimidoyl chloride (522 mg, 2.18 mmol) in DMF (5 mL) was successively added 1-fluoro-2-(trifluoromethyl)-4-(3,3,3-trifluoroprop-1-en-2-yl)benzene (563 mg, 2.18 mmol) and TEA (440 mg, 4.36 mmol) below −10° C. The mixture was stirred at rt overnight, poured into 1N HCl solution and extracted with EA (30 mL×3). The combined organic layers were washed with brine, dried over Na$_2$SO$_4$, filtered and concentrated under reduced pressure. The residue was purified by pre-TLC eluted with PE:EA (1:1, 1% HOAc) and pre-HPLC to give the final title compound (200 mg, yield 20.0%) as white solid: $^1$H NMR (300 MHz, DMSO-d$_6$): δ 9.20 (s, 1H), 8.03-8.00 (m, 1H), 7.91-7.89 (d, J=12 Hz, 1H), 7.77-7.68 (m, 4H), 4.52-4.46 (d, J=18 Hz, 1H), 4.36-4.30 (d, J=18 Hz, 1H), 1.48 (s, 6H). LC-MS: 462 [M+H]+.

25. 5-(5-(3-Chloro-4,5-difluorophenyl)-5-(trifluoromethyl)-4,5-dihydroisoxazol-3-yl)-3,3-dimethylbenzo[c][1,2]oxaborol-1(3H)-ol

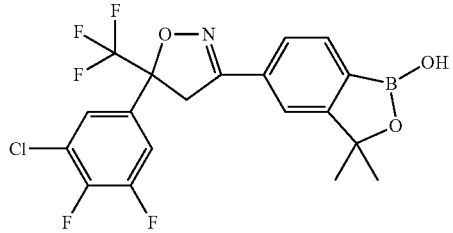 [SMILES: CC1(C)OB(O)c2ccc(C3=NOC(c4cc(F)c(F)c(Cl)c4)(C(F)(F)F)C3)cc21]

Step 1: Preparation of 3-chloro-4,5-difluoroaniline

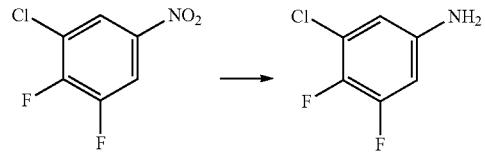 [SMILES: O=[N+]([O-])c1cc(F)c(F)c(Cl)c1 ; Nc1cc(F)c(F)c(Cl)c1]

1-Chloro-2,3-difluoro-5-nitrobenzene (3 g, 15.6 mmol) was added to acetic acid (10 mL) and methanol (250 mL). To this mixture was added iron powder (3.0 g) in portions, stirred for 2 h at 60-65° C., cooled to room temperature, and filtered. The filterate was stripped to a brown solid, which was extracted with ethyl acetate (3×200 mL), washed with 1N NaOH (3×100 mL), and brine (2×100 mL). The organic layer was dried over anhydrous magnesium sulfate, filtered and stripped down to yield the product as a pale yellow solid (2.6 g). Yield 100%; $^1$H NMR (400 MHz, CDCl$_3$): δ 6.41 (m, 2 H), 3.65 (br s, 2 H) ppm.

Step 2: Preparation of 5-bromo-1-chloro-2,3-difluorobenzene

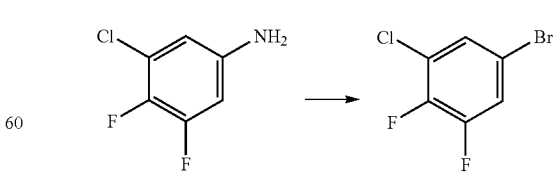

To a solution of 3-chloro-4,5-difluoroaniline (2.1 g, 12.96 mmol) in hydrobromic acid (40% in H$_2$O, 18.7 mL) was added dropwise a solution of sodium nitrite (0.96 g, 13.6 mol) in 7.5 mL H$_2$O at 0° C. Then the mixture was poured into a solution of copper(I) bromide (3.5 g, 23.7 mmol) in hydrobromic acid (40% in H₂O, 15 mL) at 0° C. The cooling bath was then removed and the mixture was heated at 60° C. overnight. After cooling, the mixture was basified with a solution 2N NaOH solution to pH=9 and diluted with CH₂Cl₂. After separation, the combined organic layers were washed with brine, dried over Na₂SO₄ and then concentrated to get crude product, which was purified by column with PE/EtOAc (from 100:1 to 20:1) as eluant to afford 2 g product. Yield 68.3%; ¹H NMR (400 MHz, CDCl₃): δ 7.37-7.35 (m, 1 H), 7.30-7.25 (m, 1 H) ppm.

Step 3: Preparation of 2-(3-chloro-4,5-difluorophenyl)-4,4,5,5-tetramethyl-1,3,2-dioxaborolane

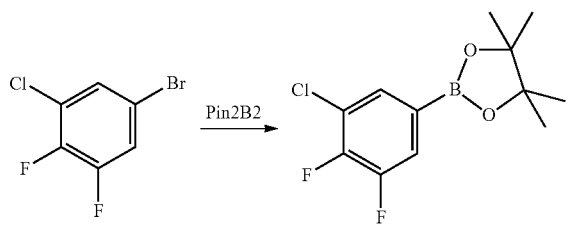 [SMILES: Fc1cc(Br)cc(Cl)c1F ; CC1(C)OB(c2cc(F)c(F)c(Cl)c2)OC1(C)C]

A mixture of 5-bromo-1-chloro-2,3-difluorobenzene (2 g, 8.85 mmol), bis(pinacolato)diboron (3.30 g, 13.1 mmol), Pd(dppf)Cl₂ (0.30 g, 0.43 mmol), KOAc (2.54 g, 26.1 mmol) in 1,4-dioxane (20 mL) was degassed with N₂ for 5 min. The reaction mixture was stirred at 70° C. for 16 h. TLC (EtOAc/Petroleum ether=1:5) indicated complete consumption of the bromo compound. The reaction mixture was poured into water (40 mL) and extracted with EtOAc (3×70 mL). The combined organic phases were dried over anhydrous Na₂SO₄, and concentrated in vacuo to give the residue, which was purified by column chromatography (silica gel, EtOAc/petroleum ether=1:10) to get the product (1.3 g, yield 54.2%) as a white solid. ¹H NMR (400 MHz, CDCl₃): δ 7.61-7.55 (m, 1 H), 7.51-7.46 (m, 1 H), 1.38 (s, 12 H) ppm.

Steps 4 and 5: Preparation of 5-(5-(3-chloro-4,5-difluorophenyl)-5-(trifluoromethyl)-4,5-dihydroisoxazol-3-yl)-3,3-dimethylbenzo[c][1,2]oxaborol-1(3H)-ol

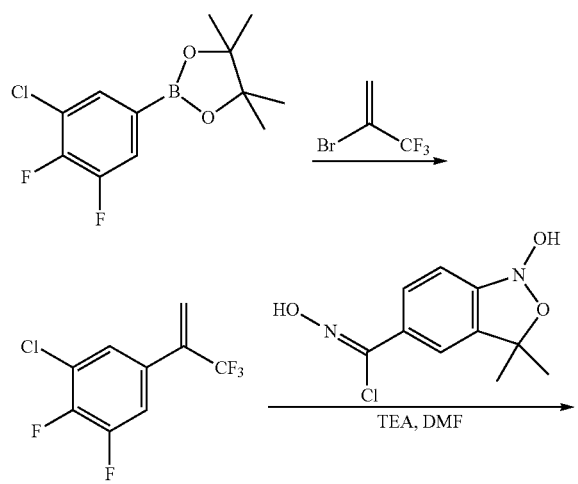

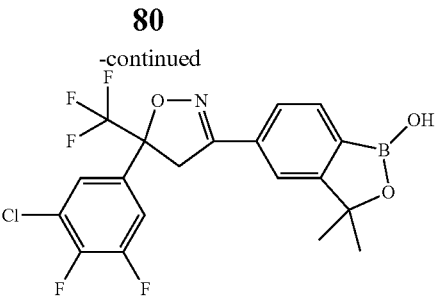

A mixture of 2-(3-chloro-4,5-difluorophenyl)-4,4,5,5-tetramethyl-1,3,2-dioxaborolane (1.2 g, 4.38 mmol), 2-bromo-3,3,3-trifluoroprop-1-ene (920 mg, 5.26 mmol, 1.2 eq), Na₂CO₃ (1.39 g, 13.14 mmol, 3 eq) and Pd(dppf)Cl₂ (358 mg, 10% mol) in DME (50 mL) and water (2 mL) was heated at 70 to 80° C. for 2 h. The mixture was cooled to 0° C. with ice-water bath, and then used to next step without work-up. To the reaction mixture were added TEA (1.33 g, 1.83 mL, 13.14 mmol, 3 eq) and N,1-dihydroxy-3,3-dimethyl-1,3-dihydrobenzo[c][1,2]oxaborole-5-carbimidoyl chloride (841 mg, 3.50 mmol, 0.8 eq) at 0° C. The reaction mixture was stirred for 12 h at rt, poured into ice-water and extracted with EA. The organic layer was washed with brine, dried over anhydrous Na₂SO₄, filtered and concentrated under reduced pressure. The residue was purified by silica gel column and prep-HPLC to give 125 mg final title product. ¹H NMR (400 MHz, DMSO-d₆): δ 9.22 (s, 1 H), 7.76-7.66 (m, 5 H), 4.43 (d, J=18.4 Hz, 1 H), 4.31 (d, J=18.4 Hz, 1 H), 1.48 (s, 6 H) ppm; MS: m/z=444/504 (M−1, ESI−).

26. 5-(5-(3,4-Dichloro-5-fluorophenyl)-5-(trifluoromethyl)-4,5-dihydroisoxazol-3-yl)-3,3-dimethylbenzo[c][1,2]oxaborol-1(3H)-ol

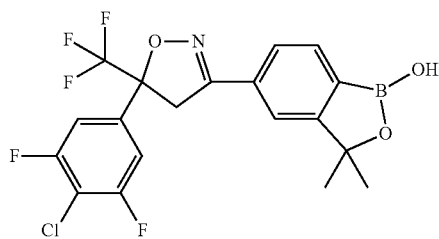 [SMILES: CC1(C)OB(O)c2ccc(C3=NOC(c4cc(F)c(Cl)c(F)c4)(C(F)(F)F)C3)cc21]

Step 1: Preparation of 2-(3,4-dichloro-5-fluorophenyl)-4,4,5,5-tetramethyl-1,3,2-dioxaborolane

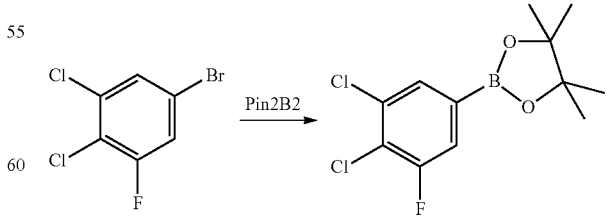

A mixture of 5-bromo-1,2-dichloro-3-fluorobenzene (2 g, 8.3 mmol), bis(pinacolato)diboron (3.1 g, 12.4 mmol), Pd(dppf)Cl₂ (0.33 g, 0.41 mmol), KOAc (2.4 g, 24.7 mmol) in 1,4-dioxane (50 mL) was degassed with N₂ for 5 minutes. The reaction mixture was stirred at 70° C. for 16 h. TLC (EtOAc/Petroleum ether=1:5) indicated complete consumption of the bromo starting material. The reaction mixture was poured into water (40 mL) and extracted with EtOAc (3×70 mL). The combined organic phases were dried over anhydrous Na₂SO₄, and concentrated in vacuo to give a crude residue, which was purified by column chromatography (silica gel, EtOAc/petroleum ether=1:10) to give the boron intermediate (2.0 g, yield: 83.3%) as a white solid.

Steps 2 and 3: Preparation of 5-(5-(3,4-dichloro-5-fluorophenyl)-5-(trifluoromethyl)-4,5-dihydroisoxazol-3-yl)-3,3-dimethylbenzo[c][1,2]oxaborol-1(3H)-ol

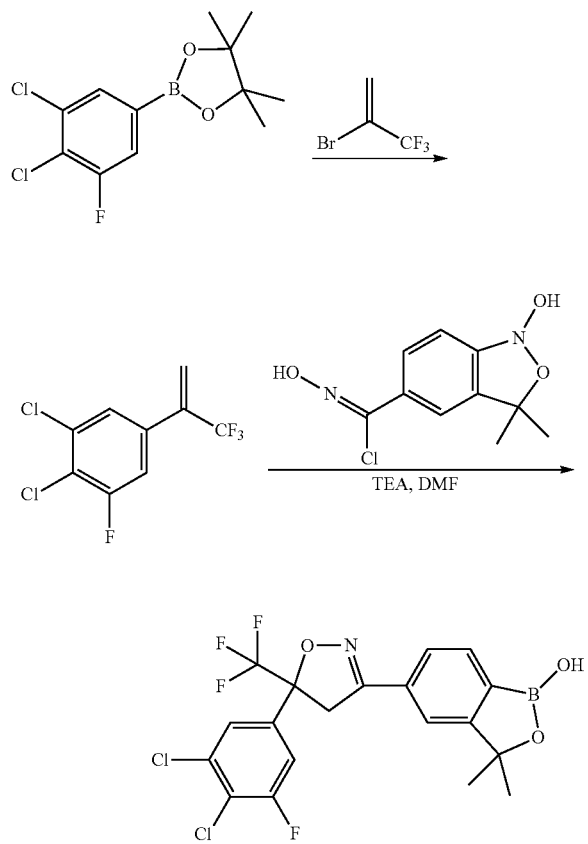

A mixture of 2-(3,4-dichloro-5-fluorophenyl)-4,4,5,5-tetramethyl-1,3,2-dioxaborolane (0.5 g, 1.73 mmol), 2-bromo-3,3,3-trifluoroprop-1-ene (0.38 g, 2.16 mmol), Cs₂CO₃ (1.8 mL, 2M, 3.6 mmol) and Pd(PPh₃)₂Cl₂ (38 mg) in THF (10 mL) was heated at 70° C. in a sealed tube for 4 h. The mixture was cooled to rt, and then N,1-dihydroxy-3,3-dimethyl-1,3-dihydrobenzo[c][1,2]oxaborole-5-carbimidoyl chloride (345 mg, 1.44 mmol) in DMF (20 mL) at rt and TEA (0.6 mL, 4.32 mmol) were added. The reaction mixture was stirred for 12 h, poured into ice-water and extracted with EA. The organic layer was washed with brine, dried over Na₂SO₄, filtered and concentrated under reduced pressure. The residue was purified by column eluted with PE-EA (10:1 to 3:1) and then purified by prep-TLC to give 80 mg of the title compound as a white solid (yield 10%). ¹H NMR (400 MHz, DMSO-d₆): δ 9.23 (s, 1 H), 7.77-7.69 (m, 5 H), 4.44 (d, J=18.8 Hz, 1 H), 4.32 (d, J=18.8 Hz, 1 H), 1.47 (s, 6 H) ppm; MS: m/z=462 (M+1, ESI+).

27. 5-(5-(3,5-Dibromo-4-chlorophenyl)-5-(trifluoromethyl)-4,5-dihydroisoxazol-3-yl)-3,3-dimethyl-benzo[c][1,2]oxaborol-1(3H)-ol

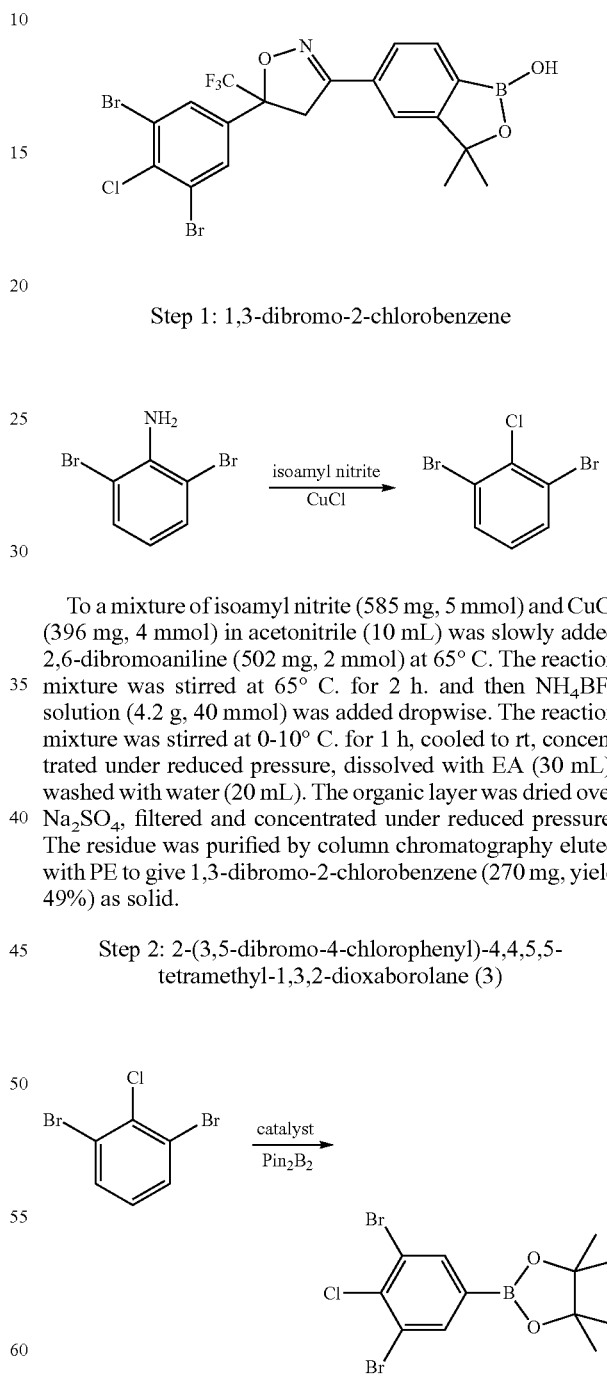

Step 1: 1,3-dibromo-2-chlorobenzene

To a mixture of isoamyl nitrite (585 mg, 5 mmol) and CuCl (396 mg, 4 mmol) in acetonitrile (10 mL) was slowly added 2,6-dibromoaniline (502 mg, 2 mmol) at 65° C. The reaction mixture was stirred at 65° C. for 2 h. and then NH₄BF₄ solution (4.2 g, 40 mmol) was added dropwise. The reaction mixture was stirred at 0-10° C. for 1 h, cooled to rt, concentrated under reduced pressure, dissolved with EA (30 mL), washed with water (20 mL). The organic layer was dried over Na₂SO₄, filtered and concentrated under reduced pressure. The residue was purified by column chromatography eluted with PE to give 1,3-dibromo-2-chlorobenzene (270 mg, yield 49%) as solid.

Step 2: 2-(3,5-dibromo-4-chlorophenyl)-4,4,5,5-tetramethyl-1,3,2-dioxaborolane (3)

To a solution of 1,3-dibromo-2-chlorobenzene (270 mg, 1 mmol) in n-heptane (15 mL) was added Pin₂B₂ (170 mg, 0.67 mmol), cycloocta-1,5-diene iridium salt (11 mg, 0.017 mmol) and 2,6-diisopropyl-N-(pyridin-2-ylmethylene)aniline (7 mg, 0.025 mmol). The mixture was refluxed for 4 h under N₂, cooled to rt, quenched with water, extracted with EA (3×50 mL). The combined organic layer was washed with brine, dried over $Na_2SO_4$, filtered and concentrated under reduced pressure. The residue was purified by column chromatography eluted with PE:EA=80:1 to give 2-(3,5-dibromo-4-chlorophenyl)-4,4,5,5-tetramethyl-1,3,2-dioxaborolane (265 mg, yield 67%) as solid.

Step 3: 1,3-dibromo-2-chloro-5-(3,3,3-trifluoroprop-1-en-2-yl)benzene

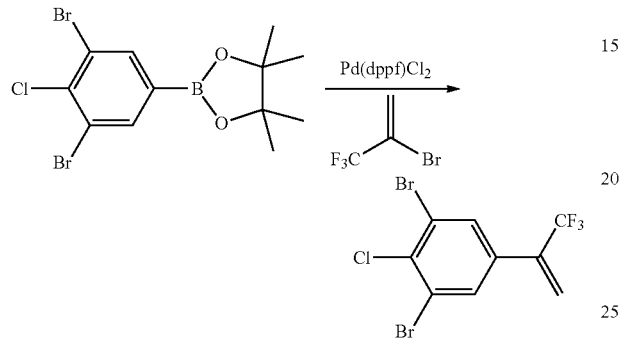

A mixture of 2-(3,5-dibromo-4-chlorophenyl)-4,4,5,5-tetramethyl-1,3,2-dioxaborolane (260 mg, 0.66 mmol), 2-bromo-3,3,3-trifluoroprop-1-ene (172 mg, 0.98 mmol), Pd(dppf)Cl$_2$ (91 mg, 0.13 mmol), K$_2$CO$_3$ (182 mg, 1.32 mmol) in THF (2 mL) and water (0.5 mL) was heated at 80° C. in a sealed vial under N$_2$ atmosphere for 12 h, cooled to rt, quenched with water, extracted with EA (3×10 mL). The combined organic layer was washed with brine, dried over Na$_2$SO$_4$, filtered and concentrated under reduced pressure. The residue was purified by column chromatography eluted with PE to give 1,3-dibromo-2-chloro-5-(3,3,3-trifluoroprop-1-en-2-yl)benzene (135 mg, yield 56%) as oil.

Step 4: 5-(5-(3,5-dibromo-4-chlorophenyl)-5-(trifluoromethyl)-4,5-dihydroisoxazol-3-yl)-3,3-dimethylbenzo[c][1,2]oxaborol-1(3H)-ol

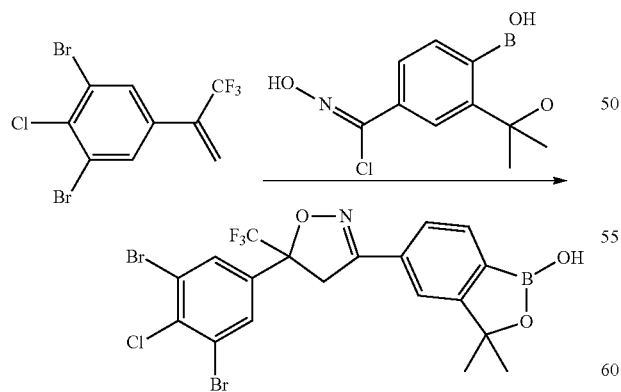

To a solution of N,1-dihydroxy-3,3-dimethyl-1,3-dihydrobenzo[c][1,2]oxaborole-5-carbimidoyl chloride (68 mg, 0.28 mmol) in DMF was added 1,3-dibromo-2-chloro-5-(3,3,3-trifluoroprop-1-en-2-yl)benzene (132 mg, 0.36 mmol) and TEA (31 mg, 0.36 mmol) at rt. The mixture was stirred at 25° C. for 12 h, quenched with water, extracted with EA (3×10 mL). The combined organic layer was washed with brine, dried over Na$_2$SO$_4$, filtered and concentrated under reduced pressure. The residue was purified by column chromatography eluted with PE:EA=5:1 to give the final title compound 5-(5-(3,5-dibromo-4-chlorophenyl)-5-(trifluoromethyl)-4,5-dihydroisoxazol-3-yl)-3,3-dimethyl-benzo[c][1,2]oxaborol-1(3H)-ol (38 mg; yield 22%) as solid. $^1$H NMR (400 MHz, DMSO-d$_6$): δ 9.21 (s, 1H), 7.96 (s, 2H), 7.76-7.69 (m, 3H), 4.45-4.30 (q, 2H), 1.48 (s, 6H) ppm; MS: m/z=568 (M+1, ESI+).

28. (S)-5-(5-(3,5-Dichloro-4-fluorophenyl)-5-(trifluoromethyl)-4,5-dihydroisoxazol-3-yl)-3,3-dimethylbenzo[c][1,2]oxaborol-1(3H)-ol

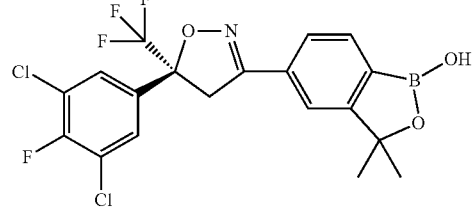

The title compound was obtained by separation of the racemic mixture of 545-(3,5-dichloro-4-fluorophenyl)-5-(trifluoromethyl)-4,5-dihydroisoxazol-3-yl)-3,3-dimethyl-benzo[c][1,2]oxaborol-1(3H)-ol with chiral column chromatography. The racemic mixture was dissolved in the solvent of mobile phase and separated by supercritical fluid (SFC) chiral chromatography. The chromatography conditions used were: column CHIRALCEL OJ-H (column size: 0.46 cm I.D.×15 cm length), mobile phase CO$_2$/MeOH=70/30 (w/w), flow rate 2.0 mL/min, detector wave length UV 220 nm, and temperature 35° C.

29. (R)-5-(5-(3,5-Dichloro-4-fluorophenyl)-5-(trifluoromethyl)-4,5-dihydroisoxazol-3-yl)-3,3-dimethylbenzo[c][1,2]oxaborol-1(3H)-ol

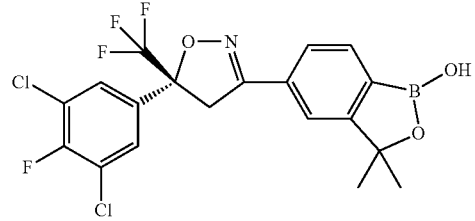 [SMILES: CC1(C)OB(O)c2ccc(C3=NO[C@](c4cc(Cl)c(F)c(Cl)c4)(C(F)(F)F)C3)cc21]

The title compound was obtained by separation of the racemic mixture of 5-(5-(3,5-dichloro-4-fluorophenyl)-5-(trifluoromethyl)-4,5-dihydroisoxazol-3-yl)-3,3-dimethyl-benzo[c][1,2]oxaborol-1(3H)-ol with chiral column chromatography. The racemic mixture was dissolved in the solvent of mobile phase and separated by supercritical fluid (SFC) chiral chromatography. The chromatography conditions used were: column CHIRALCEL OJ-H (column size: 0.46 cm I.D.×15

30. 5-(5-(4-Chloro-3,5-difluorophenyl)-5-(trifluoromethyl)-4,5-dihydroisoxazol-3-yl)-3,3-dimethylbenzo[c][1,2]oxaborol-1(3H)-ol

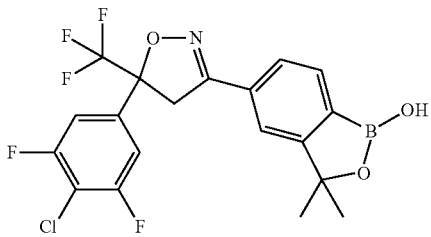 [SMILES: CC1(C)OB(O)c2ccc(C3=NOC(c4cc(F)c(Cl)c(F)c4)(C(F)(F)F)C3)cc21]

The title compound was synthesized by the following scheme:

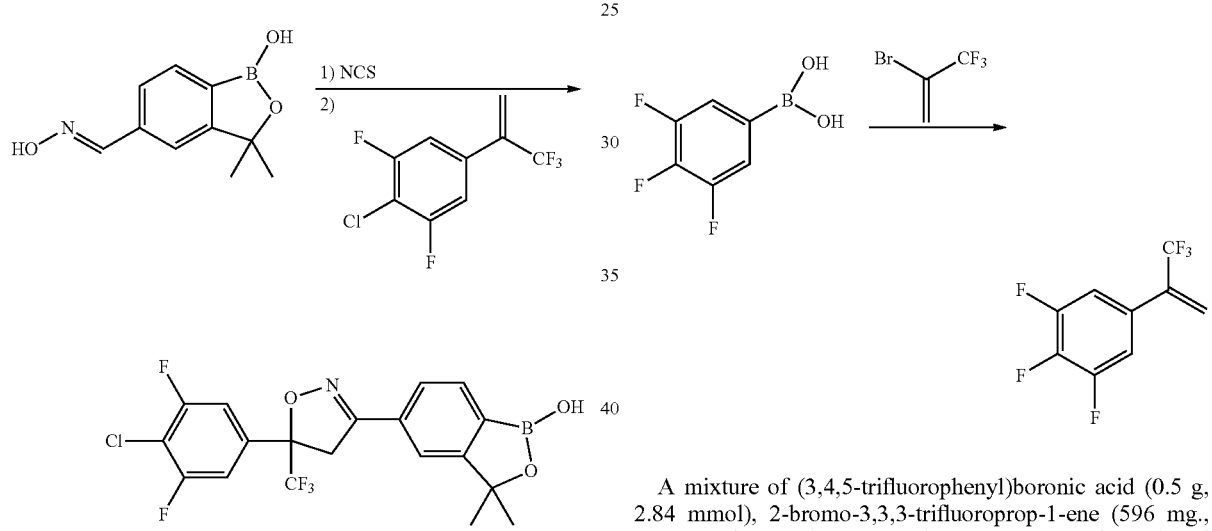

To a solution of (E)-1-hydroxy-3,3-dimethyl-1,3-dihydrobenzo[c][1,2]oxaborole-5-carbaldehyde oxime (200 mg, 0.98 mmol) in DMF (7 mL) at rt was added NCS (157 mg, 1.17 mmol). The reaction mixture was warmed to 45° C., stirred for 2.5 h and cooled to rt. This mixture was added dropwise to a solution of 2-chloro-1,3-difluoro-5-(3,3,3-trifluoroprop-1-en-2-yl)benzene (237 mg, 0.98 mmol) and TEA (218 mg, 2.16 mmol) in DMF (7 mL) at 0° C. The mixture was stirred at this temperature for 1 h, and then at rt overnight. The mixture was acidified with 3 N HCl to pH of 2, then poured into water and extracted with EA (50 mL×2). The combined organic layers were washed with brine, dried over $Na_2SO_4$, filtered and concentrated under reduced pressure. The residue was purified by prep-TLC (PE:EA=2:1) to give the final title compound (150 mg, yield 35%) as white solid. $^1$H NMR (300 MHz, DMSO-$d_6$): δ 9.24 (s, 1H), 7.82-7.73 (m, 3H), 7.71-7.60 (m, 2H), 4.50 (d, J=18.3 Hz, 1H), 4.44 (d, J=18.3 Hz, 1H), 1.51 (s, 3H), 1.50 (s, 3H) ppm; HPLC purity: 95.5% at 214 nm and 97.8% at 254 nm; MS: m/z=446 (M+1, ESI+).

31. 3,3-Dimethyl-5-(5-(trifluoromethyl)-5-(3,4,5-trifluorophenyl)-4,5-dihydroisoxazol-3-yl)benzo[c][1,2]oxaborol-1(3H)-ol

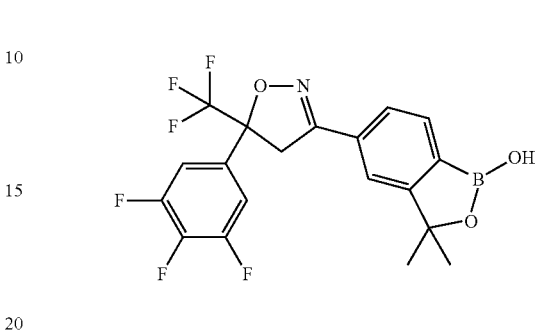

Step 1: Preparation of 1,2,3-trifluoro-5-(3,3,3-trifluoroprop-1-en-2-yl)benzene

A mixture of (3,4,5-trifluorophenyl)boronic acid (0.5 g, 2.84 mmol), 2-bromo-3,3,3-trifluoroprop-1-ene (596 mg., 3.41 mmol, 1.2 eq), $Na_2CO_3$ (0.90 g, 8.52 mmol, 3 eq) and Pd(dppf)Cl$_2$ (232 mg, 10% mol) in DME (20 mL) and water (2 mL) was heated at 70 to 80° C. for 2 h. The mixture was cooled to 0° C. with ice-water bath, and then used to next step without further purification.

Step 2: Preparation of 3,3-dimethyl-5-(5-(trifluoromethyl)-5-(3,4,5-trifluorophenyl)-4,5-dihydroisoxazol-3-yl)benzo[c][1,2]oxaborol-1(3H)-ol

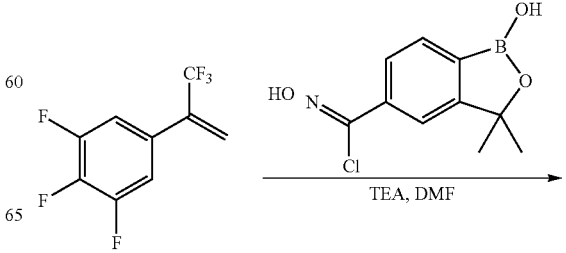

-continued

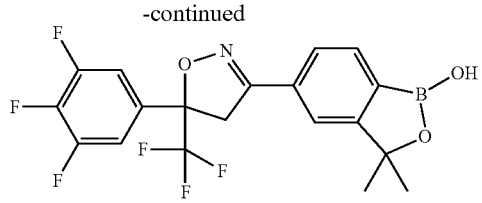

To a solution of 1,2,3-trifluoro-5-(3,3,3-trifluoroprop-1-en-2-yl)benzene in DMF were added TEA (0.86 g, 1.18 mL, 8.52 mmol, 3 eq) and N,1-dihydroxy-3,3-dimethyl-1,3-dihydrobenzo[c][1,2]oxaborole-5-carbimidoyl chloride (545 mg, 2.27 mmol, 0.8 eq) at 0° C. The reaction mixture was stirred for 12 h at rt, poured into ice-water and extracted with EA. The organic layer was washed with brine, dried over anhydrous $Na_2SO_4$, filtered and concentrated under reduced pressure. The residue was purified by silica column and prep-HPLC to give 105 mg pure product. $^1$H NMR (400 MHz, DMSO-$d_6$): δ 9.23 (s, 1H), 7.76-7.59 (m, 5H), 4.43 (d, J=18.4 Hz, 1H), 4.28 (d, J=18.4 Hz, 1H), 1.48 (s, 3H), 1.47 (s, 3H) ppm; HPLC purity: 99.6% at 254 nm; MS: m/z=430 (M+1, ESI+).

32. 5-(5-(3,5-Dibromo-4-fluorophenyl)-5-(trifluoromethyl)-4,5-dihydroisoxazol-3-yl)-3,3-dimethylbenzo[c][1,2]oxaborol-1(3H)-ol

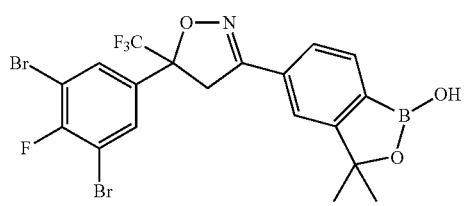 [SMILES: CC1(C)OB(O)c2ccc(C3=NOC(c4cc(Br)c(F)c(Br)c4)(C(F)(F)F)C3)cc21]

Step 1: 1,3-dibromo-2-fluorobenzene

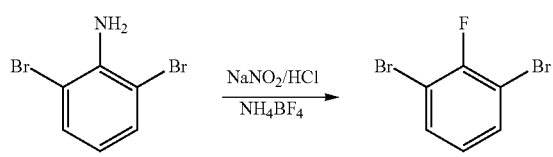

To a mixture of 2,6-dibromoaniline (5.0 g, 20 mmol) and HCl (12 N, 10 mL) was added $NaNO_2$ (2.1 g, 30 mmol) at 0° C. The reaction mixture was stirred at 0-10° C. for 1 h, and then $NH_4BF_4$ solution (4.2 g, 40 mmol) was added dropwise. The reaction mixture was stirred at 0-10° C. for 1 h. The precipitate was filtered and dried. The residue obtained was heated to 220° C. for 2 h, cooled to rt and dissolved with EA (150 mL), washed with NaOH (2 N, 200 mL). The organic layer was dried over $Na_2SO_4$, filtered and concentrated under reduced pressure to give 1,3-dibromo-2-fluorobenzene (1.45 g, yield 29%).

Step 2: 2-(3,5-dibromo-4-fluorophenyl)-4,4,5,5-tetramethyl-1,3,2-dioxaborolane

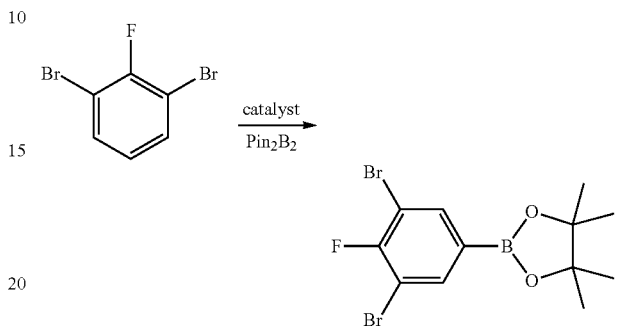

To a solution of 1,3-dibromo-2-fluorobenzene (1.43 g, 5.63 mmol) in n-heptane (100 mL) was added $Pin_2B_2$ (953 mg, 3.75 mmol), cycloocta-1,5-diene iridium salt (63 mg, 0.094 mmol) and 2,6-diisopropyl-N-(pyridin-2-ylmethylene) aniline (37 mg, 0.14 mmol). The mixture was refluxed for 4 h under $N_2$, cooled to rt, quenched with water, extracted with EA (3×50 mL). The combined organic layer was washed with brine, dried over $Na_2SO_4$, filtered and concentrated under reduced pressure. The residue was purified by column chromatography eluted with PE: EA=80:1 to give 2-(3,5-dibromo-4-fluorophenyl)-4,4,5,5-tetramethyl-1,3,2-dioxaborolane (1.046 g, yield 49%) as solid.

Step 3: 1,3-dibromo-2-fluoro-5-(3,3,3-trifluoroprop-1-en-2-yl)benzene

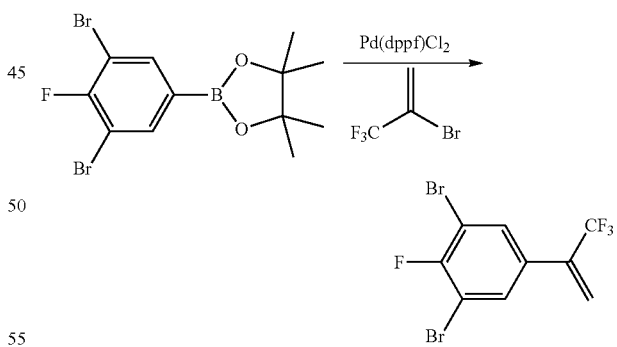

A mixture of 2-(3,5-dibromo-4-fluorophenyl)-4,4,5,5-tetramethyl-1,3,2-dioxaborolane (300 mg, 0.79 mmol), 2-bromo-3,3,3-trifluoroprop-1-ene (207 mg, 1.18 mmol), Pd(dppf)$Cl_2$ (112 mg, 0.16 mmol), $K_2CO_3$ (218 mg, 1.58 mmol) in THF (2 mL) and water (1 mL) was heated at 80° C. in a sealed vial under $N_2$ atmosphere for 12 h, cooled to rt, quenched with water, extracted with EA (3×10 mL). The combined organic layer was washed with brine, dried over $Na_2SO_4$, filtered and concentrated under reduced pressure. The residue was purified by column chromatography eluted with PE to give 1,3-dibromo-2-fluoro-5-(3,3,3-trifluoroprop-1-en-2-yl)benzene (100 mg, yield 30%) as solid.

Step 4: 5-(5-(3,5-dibromo-4-fluorophenyl)-5-(trifluoromethyl)-4,5-dihydroisoxazol-3-yl)-3,3-dimethylbenzo[c][1,2]oxaborol-1(3H)-ol

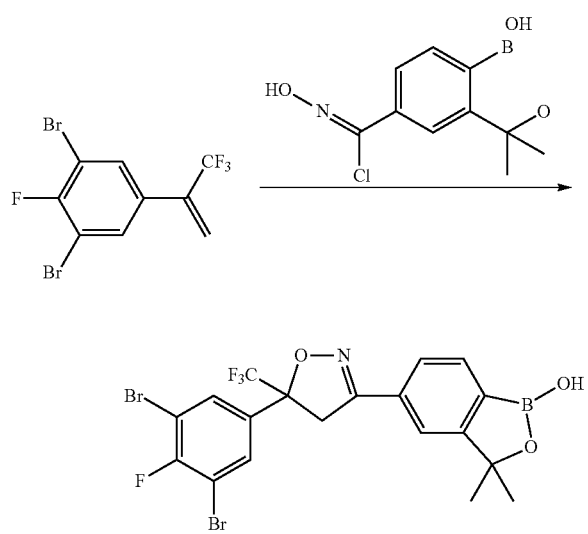

To a solution of N,1-dihydroxy-3,3-dimethyl-1,3-dihydrobenzo[c][1,2]oxaborole-5-carbimidoyl chloride (34 mg, 0.14 mmol) in DMF (3 mL) was added 1,3-dibromo-2-fluoro-5-(3,3,3-trifluoro-prop-1-en-2-yl)benzene (50 mg, 0.14 mmol) and TEA (15 mg, 0.14 mmol) at rt. The mixture was stirred at 25° C. for 12 h, quenched with water, extracted with EA (3×10 mL). The combined organic layer was washed with brine, dried over $Na_2SO_4$, filtered and concentrated. The residue was purified by column chromatography eluted with PE:EA (5:1) to give the final title compound 5-(5-(3,5-dibromo-4-fluorophenyl)-5-(trifluoromethyl)-4,5-dihydroisoxazol-3-yl)-3,3-dimethylbenzo[c][1,2]oxaborol-1(3H)-ol (50 mg; yield 59%) as solid. $^1$H NMR (400 MHz, DMSO-$d_6$): δ 9.22 (s, 1H), 7.92-7.68 (m, 5H), 4.45-4.40 (q, J=22 Hz, 1H), 4.34-4.30 (q, J=22 Hz, 1H), 1.48 (s, 6H) ppm; HPLC purity: 96.9% at 220 nm and 98.4% at 254 nm; MS: m/z=552.0 (M+1, ESI+).

33. 3,3-Bis(fluoromethyl)-5-(5-(3,4,5-trichlorophenyl)-5-(trifluoromethyl)-4,5-dihydroisoxazol-3-yl)benzo[c][1,2]oxaborol-1(3H)-ol

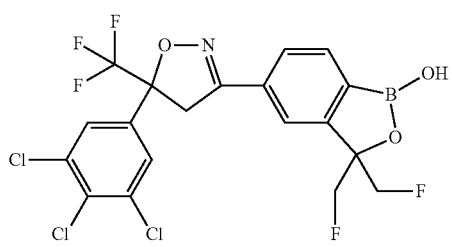 [SMILES: OB1OC(CF)(CF)c2cc(C3=NOC(c4cc(Cl)c(Cl)c(Cl)c4)(C(F)(F)F)C3)ccc21]

Step 1: Preparation of 2-iodo-4-methylaniline

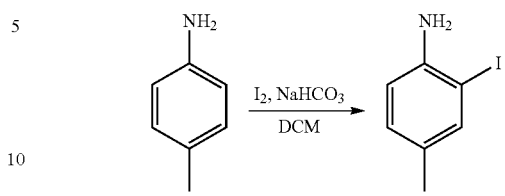

To a solution of 4-methylaniline (53.5 g, 500 mmol) in DCM (200 mL) was added a solution of $NaHCO_3$ (50.4 g) in water (500 mL), and then $I_2$ (127 g) was added. The mixture was stirred at rt overnight. The mixture was treated with aqueous $NaHSO_3$ and extracted with DCM. The combined organic layers were washed with brine, dried over $Na_2SO_4$, and then concentrated in vacuo to afford the product as brown oil (110 g, yield 95%). $^1$H NMR (300 MHz, CDCl$_3$): δ 7.48 (dd, J=1.8 & 0.6 Hz, 1H), 6.96 (dd, J=8.1 & 1.8 Hz, 1H), 6.67 (d, J=8.1 Hz, 1H), 3.98 (bs, 2H), 2.22 (s, 3H) ppm.

Step 2: Preparation of 1-bromo-2-iodo-4-methylbenzene

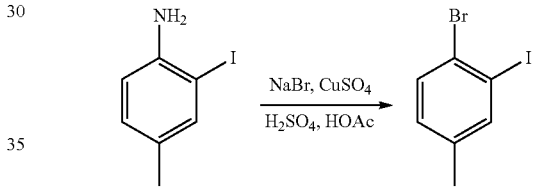

To a mixture of 2-iodo-4-methylaniline (50 g, 214.55 mmol) in HOAc (250 mL), $H_2SO_4$ (10 mL), and $H_2O$ (40 mL) was added a solution of $NaNO_2$ (14.5 g) in $H_2O$ (80 mL) at 0° C. The solution was stirred for 1.5 h. This was defined as mixture A. In another round bottom flask, a mixture of NaBr (107 g), $CuSO_4$ (32.2 g), Cu (38.9 g), $H_2SO_4$ (39 mL), and $H_2O$ (25 mL) was refluxed for 1.5 h. To this mixture was added mixture A, and the solution was then refluxed for 3 h. The solution was treated with water and extracted with EA (500 mL×3). The combined organic layers were washed with brine, dried over Na2SO4, and then concentrated in vacuo. Purification by column chromatography over silica gel eluted with PE afforded the product as colorless oil (43 g, yield 68%). $^1$H NMR (300 MHz, CDCl$_3$): δ 7.69 (m, 1H), 7.47 (d, J=8.1 Hz, 1H), 7.00 (m, 1H), 2.26 (s, 3H) ppm.

Step 3: Preparation of 2-(2-bromo-5-methylphenyl)-1,3-difluoropropan-2-ol

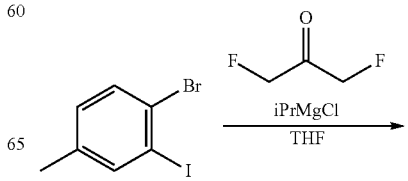

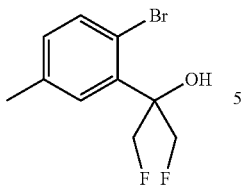

To a solution of 1-bromo-2-iodo-4-methylbenzene (18.5 g, 62.3 mmol) in THF (50 mL) at 0° C. was slowly added i-PrMgCl (12 mL, 23.47 mmol). After stirring for 1 h at 0° C., the reaction temperature was cooled to −70° C. Then a solution of 1,3-difluoropropan-2-one (1.7 g, 18.05 mmol) in dry THF (5 mL) was added. The mixture was stirred at −70° C. for 1 h, and then dry ice bath was removed. The solution was acidified with 2 N HCl and extracted with EA (60 mL×2). The combined organic layers were washed with brine, dried over Na$_2$SO$_4$, filtered and concentrated under reduced pressure. The residue was purified by column chromatography over silica gel eluted with PE:EA (25:1) to give the desired product (2.5 g, yield 53%) as colorless oil. $^1$H NMR (300 MHz, CDCl$_3$): δ 7.61 (d, J=1.8 Hz, 1H), 7.46 (d, J=8.1 Hz, 1H), 7.02-6.99 (m, 1H), 5.13-5.09 (m, 1H), 5.02-4.94 (m, 2H), 4.87-4.82 (m, 1H), 3.27 (bs, 1H), 2.33 (s, 3H) ppm.

Step 4: Preparation of 1-bromo-2-(2-(ethoxymethoxy)-1,3-difluoropropan-2-yl)-4-methylbenzene

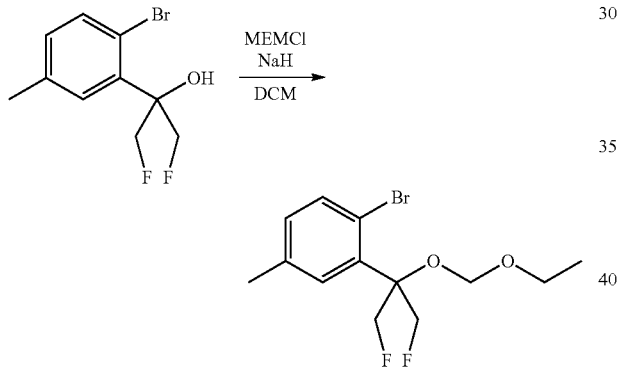

NaH (362 mg, 9.05 mmol) was added to a solution of 2-(2-bromo-5-methylphenyl)-1,3-difluoropropan-2-ol (2.0 g, 7.54 mmol) in THF (10 mL) slowly at 0° C. MEMCl (1.41 g, 11.32 mmol) was added dropwise. The mixture was stirred at rt overnight. The mixture was diluted with H$_2$O and extracted with EA (50 mL×2). The combined organic layers were washed with brine, dried over Na$_2$SO$_4$, filtered and concentrated under reduced pressure. The residue was purified by column chromatography over silica gel eluted with PE:EA (10:1 to 6:1) to give the product (1.8 g, yield 68%) as colorless oil.

Step 5: Preparation of 3,3-bis(fluoromethyl)-5-methylbenzo[c][1,2]oxaborol-1(3H)-ol

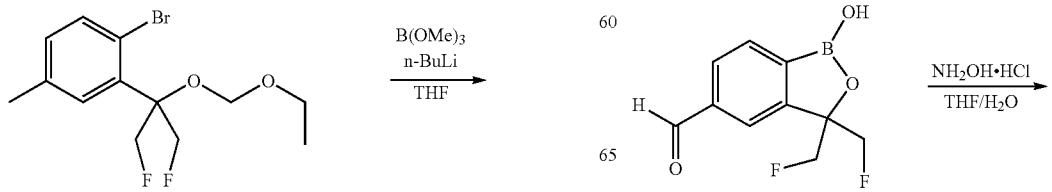

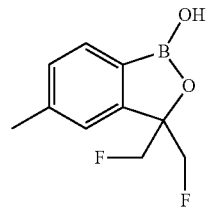

To a solution of 1-bromo-2-(2-(ethoxymethoxy)-1,3-difluoropropan-2-yl)-4-methylbenzene (1.8 g, 5.10 mmol) in THF (15 mL) at −78° C. was slowly added n-BuLi (5.1 mL, 12.75 mmol). After stirring for 10 min, a solution of B(OMe)$_3$ (1.06 g, 10.2 mmol) in dry THF (5 mL) was added dropwise. The mixture was stirred at −78° C. for 0.5 h, and then dry ice bath was removed. The solution was acidified with HCl (4 N) and extracted with EA (100 mL×2). The combined organic layers were washed with brine, dried over Na$_2$SO$_4$, filtered and concentrated under reduced pressure. The residue was purified by column chromatography over silica gel eluted with PE:EA (5:1 to 3:1) to give the desired compound (350 mg, yield 32%) as white solid.

Step 6: Preparation of 3,3-bis(fluoromethyl)-1-hydroxy-1,3-dihydrobenzo[c][1,2]oxaborole-5-carbaldehyde

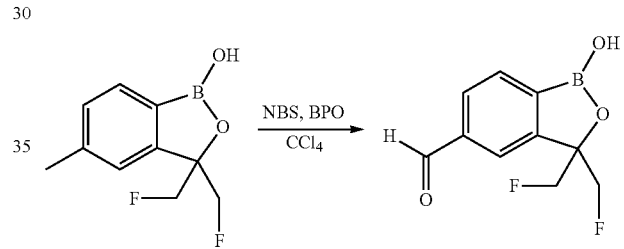

A solution of 3,3-bis(fluoromethyl)-5-methylbenzo[c][1,2]oxaborol-1(3H)-ol (350 mg, 1.65 mmol), NBS (647 mg, 3.63 mmol), and BPO (40 mg, 0.17 mmol) in CCl$_4$ (10 mL) was refluxed overnight. After treating with aqueous Na$_2$CO$_3$, the aqueous phase was acidified with HCl (3 N) to pH of 3, and then extracted with EA. The organic layer was washed with brine, dried over Na$_2$SO$_4$, filtered and concentrated under reduced pressure to afford the crude product (400 mg) as a yellow solid that was used directly in the next step without purification. $^1$H NMR (300 MHz, CDCl$_3$): δ 10.09 (s, 1H), 7.98-7.94 (m, 3H), 4.79-4.74 (m, 2H), 4.63-4.59 (m, 2H).

Step 7: Preparation of (E)-3,3-bis(fluoromethyl)-1-hydroxy-1,3-dihydrobenzo[c][1,2]oxaborole-5-carbaldehyde oxime

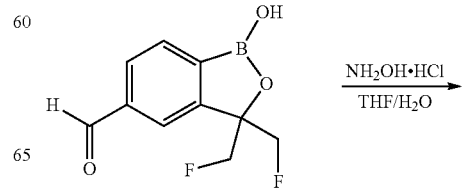

-continued

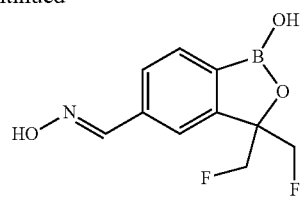

To a mixture of 3,3-bis(fluoromethyl)-1-hydroxy-1,3-dihydrobenzo[c][1,2]oxaborole-5-carbaldehyde (400 mg, 1.77 mmol) and NH$_2$OH.HCl (148 mg, 2.12 mmol) in THF (25 mL) and H$_2$O (5 mL) at rt was added NaOAc (203 mg, 2.48 mmol). The mixture was stirred at rt overnight, diluted with H$_2$O and extracted with EA (50 mL×2). The combined organic layers were washed with brine, dried over Na$_2$SO$_4$, filtered and concentrated under reduced pressure. The crude product (440 mg) was used directly in the next step without purification.

Step 8: Preparation of 3,3-bis(fluoromethyl)-5-(5-(3,4,5-trichlorophenyl)-5-(trifluoromethyl)-4,5-dihydro-isoxazol-3-yl)benzo[c][1,2]oxaborol-1(3H)-ol

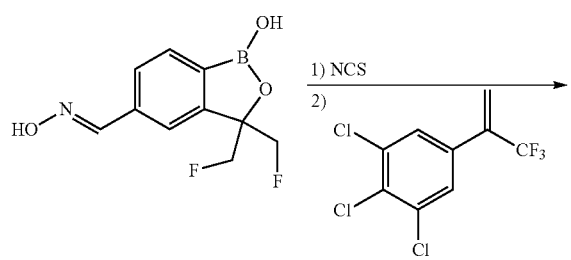

To a solution of (E)-3,3-bis(fluoromethyl)-1-hydroxy-1,3-dihydrobenzo[c][1,2]oxaborole-5-carbaldehyde oxime (440 mg, 1.83 mmol) in DMF (10 mL) at rt was added NCS (294 mg, 2.19 mmol). The reaction mixture was warmed to 45° C., stirred for 2.5 h and cooled to rt. To a solution of 1,2,3-trichloro-5-(3,3,3-trifluoroprop-1-en-2-yl)benzene (577 mg, 2.10 mmol) and TEA (403 mg, 4.0 mmol) in DMF (10 mL) was added the above mixture dropwise at 0° C. The mixture was stirred at 0° C. for 1 h, then stirred at rt overnight. The mixture was acidified with HCl (3 N) to pH of 2, then poured into water and extracted with EA (50 mL×2). The combined organic layers were washed with brine, dried over Na$_2$SO$_4$, filtered and concentrated under reduced pressure. The residue was purified by prep-TLC (PE:EA=2:1) to give the final title compound (150 mg, 16%) as white solid. $^1$H NMR (300 MHz, DMSO-d$_6$): δ 9.74 (s, 1H), 7.96-7.80 (m, 5H), 4.89- 4.80 (m, 2H), 4.73-4.64 (m, 2H), 4.46 (d, J=17.4 Hz, 1H), 4.35 (d, J=17.4 Hz, 1H) ppm; HPLC purity: 95.3% at 214 nm; MS: m/z=516 (M+1, ESI+).

34. 3,3-Dimethyl-5-(5-(2,3,4,5-tetrachlorophenyl)-5-(trifluoromethyl)-4,5-dihydroisoxazol-3-yl)benzo[c][1,2]oxaborol-1(3H)-ol

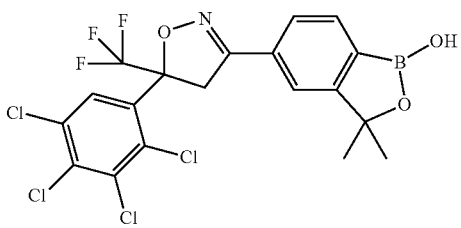 [SMILES: CC1(C)OB(O)c2ccc(C3=NOC(c4cc(Cl)c(Cl)c(Cl)c4Cl)(C(F)(F)F)C3)cc21]

To the solution of N,1-dihydroxy-3,3-dimethyl-1,3-dihydrobenzo[c][1,2]oxaborole-5-carbimidoyl chloride (0.526 mmol) in DMF (3 mL) was added 1,2,3,4-tetrachloro-5-(3,3,3-trifluoroprop-1-en-2-yl)benzene (245 mg, 0.789 mmol) and TEA (106 mg, 1.052 mmol) at rt. The mixture was stirred at 25° C. for 12 h, quenched with water, extracted with EA (3×10 mL). The combined organic layer was washed with brine, dried over Na$_2$SO$_4$, filtered and concentrated under reduced pressure. The residue was purified by prep-HPLC to give the final title compound 3,3-dimethyl-5-(5-(2,3,4,5-tetrachlorophenyl)-5-(trifluoromethyl)-4,5-dihydroisoxazol-3-yl)benzo[c][1,2]oxaborol-1(3H)-ol (52 mg; yield 13%) as a solid. $^1$H NMR (400 MHz, DMSO-d$_6$): δ 9.20 (s, 1H), 7.98 (s, 1H), 7.83 (s, 1H), 7.76-7.47 (d, J=3.2 Hz, 2H), 4.67-4.63 (d, J=18 Hz, 1H), 4.37-4.35 (d, J=18.8 Hz, 1H), 1.49 (s, 3H), 1.48 (s, 3H) ppm; MS: m/z=514 (M+1, ESI+).

35. 5-(5-(3,5-Dichloro-2,4-difluorophenyl)-5-(trifluoromethyl)-4,5-dihydroisoxazol-3-yl-3,3-dimethylbenzo[c][1,2]oxaborol-1(3H)-ol

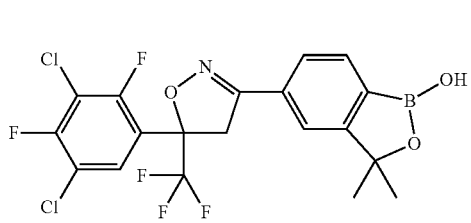 [SMILES: CC1(C)OB(O)c2ccc(C3=NOC(c4cc(Cl)c(F)c(Cl)c4F)(C(F)(F)F)C3)cc21]

Step 1: Preparation of 1-bromo-3,5-dichloro-2,4-difluorobenzene

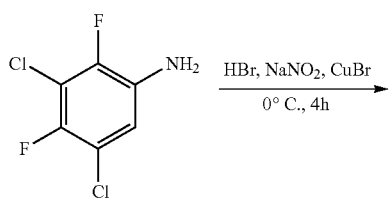

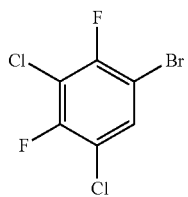

To a solution of 3,5-dichloro-2,4-difluorobenzenamine (9.9 g, 50.0 mmol) in HBr (200 mL) was added a solution of NaNO₂ (3.45 g, 50.0 mmol) in H₂O (80 mL) slowly under salt ice-bath, then the mixture was stirred for 2 h, and CuBr (7.15 g, 50.0 mmol) was added at 0° C. The mixture was stirred for additional 2 h, and then poured into water (100 mL), extracted with DCM, dried over NaSO₄, filtered and concentrated under reduced pressure. The resulting residue was purified by chromatography over silica gel eluted with PE to give compound 1-bromo-3,5-dichloro-2,4-difluorobenzene (6.2 g, yield 48%) as a colorless oil. ¹H NMR (400 MHz, CDCl₃): δ 7.49 (t, J=7.2 Hz, 1H) ppm.

Step 2: Preparation of 2-(3,5-dichloro-2,4-difluorophenyl)-4,4,5,5-tetramethyl-1,3,2-dioxaborolane

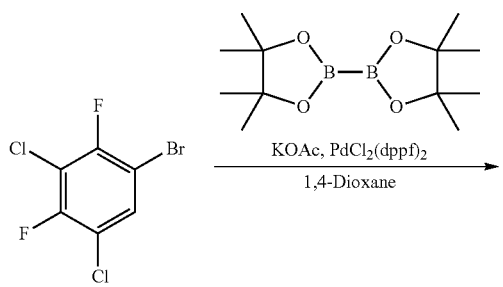

A mixture of 1-bromo-3,5-dichloro-2,4-difluorobenzene (6.2 g, 23.75 mmol), bis(pinacolato)-diboron (18.1 g, 71.25 mmol), Pd(dppf)Cl₂ (521 mg, 0.713 mmol) and KOAc (6.98 g, 71.25 mmol) in 1,4-dioxane (150 mL) was stirred at 80° C. overnight under argon. Water (200 mL) was added and the mixture was extracted three times with ethyl acetate. The combined extracts were washed with water and brine, dried over Na₂SO₄, filtered and concentrated under reduced pressure. The residue was purified by column chromatography over silica gel eluted with PE-EA (10:1) to give 2-(3,5-dichloro-2,4-difluorophenyl)-4,4,5,5-tetramethyl-1,3,2-dioxaborolane as a white solid.

Step 3: Preparation of 1,3-dichloro-2,4-difluoro-5-(3,3,3-trifluoroprop-1-en-2-yl)-benzene

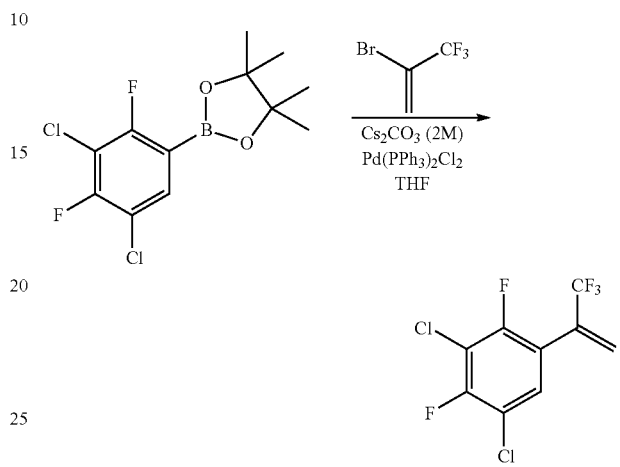

A mixture of 2-(3,5-dichloro-2,4-difluorophenyl)-4,4,5,5-tetramethyl-1,3,2-dioxaborolane (7.34 g, 23.75 mmol), 2-bromo-3,3,3-trifluoroprop-1-ene (5.82 g, 33.25 mmol), Cs₂CO₃ (15.5 g, 47.5 mmol) and Pd(PPh₃)₂Cl₂ (400 mg) in THF (30 mL) and water (15 mL) was heated at 70° C. in a sealed tube for 4 h under argon. The mixture was cooled to rt and partitioned between EA and H₂O. The aqueous layer was extracted with EA and the combined organic layers were dried over Na₂SO₄. The solvent was removed and the residue was purified by column chromatography on silica gel eluted with hexanes to give crude compound of 1,3-dichloro-2,4-difluoro-5-(3,3,3-trifluoroprop-1-en-2-yl)benzene (3.93 g) as a colorless oil. It was used in next step without further purification.

Step 4: Preparation of 5-(5-(3,5-dichloro-2,4-difluorophenyl)-5-(trifluoromethyl)-4,5-dihydroisoxazol-3-yl)-3,3-dimethylbenzo[c][1,2]oxaborol-1(3H)-ol

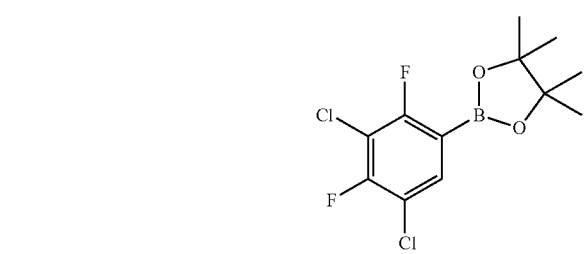

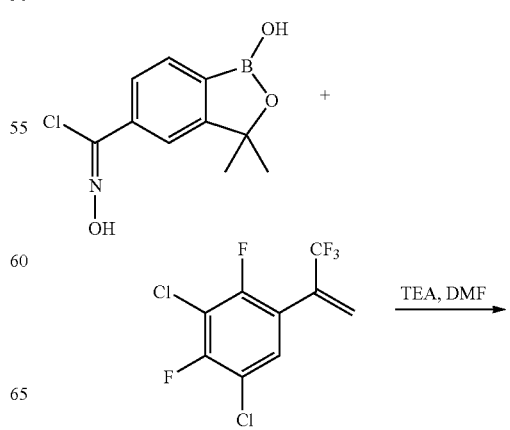

-continued

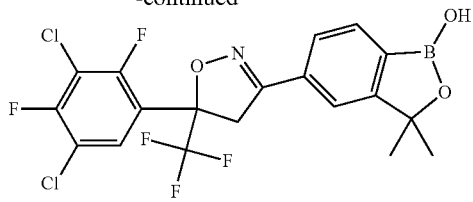

To a solution of N,1-dihydroxy-3,3-dimethyl-1,3-dihydrobenzo[c][1,2]-oxaborole-5-carbimidoyl chloride (3.0 g, 12.63 mmol) and 1,3-dichloro-2,4-difluoro-5-(3,3,3-trifluoroprop-1-en-2-yl)-benzene (3.93 g, 14.19 mmol) in DMF (20 mL) at rt was added TEA (2.7 mL, 18.95 mmol). The reaction mixture was stirred for 12 h, poured into ice-water and extracted with EA. The organic layer was washed with brine, dried over $Na_2SO_4$, filtered and concentrated under reduced pressure. The residue was purified by column chromatography over silica gel eluted with PE-EA (1:1) to give the title compound 5-(5-(3,5-dichloro-2,4-difluorophenyl)-5-(trifluoromethyl)-4,5-dihydroisoxazol-3-yl)-3,3-dimethylbenzo[c][1,2]oxaborol-1(3H)-ol[1.3 g, yield: 21.4% (3 steps)] as a white solid. $^1$H NMR (500 MHz, DMSO-$d_6$): δ 9.23 (s, 1H), 7.87 (t, J=7.5 Hz, 1H), 7.83 (s, 1H), 7.75 (s, 2H), 4.59 (d, J=18.5 Hz, 1H), 4.37 (d, J=18.5 Hz, 1H), 1.50 (s, 3H), 1.48 (s, 3H) ppm; HPLC purity: 100.0% at 220 nm and 100.0% at 254 nm; MS: m/z=479.8 (M+1, ESI+).

36. 5-(5-(3,5-Dichlorophenyl)-5-(trifluoromethyl)-4,5-dihydroisoxazol-3-yl)-3,3-diethyl-benzo[c][1,2]oxaborol-1(3H)-ol

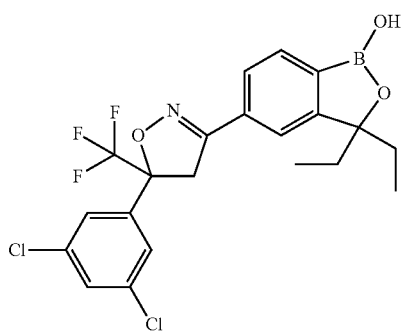 [SMILES: CCC1(CC)OB(O)c2ccc(C3=NOC(c4cc(Cl)cc(Cl)c4)(C(F)(F)F)C3)cc21]

Step 1: Preparation of 2-iodo-4-methylaniline

To a stirred solution of p-toluidine (50 g, 467 mmol) in methylene chloride (250 mL) was added a solution of sodium bicarbonate (47 g, 560 mmol) in water (750 mL). Then it was added iodine (118.6 g, 467 mmol) in small portions and the mixture was stirred for 16 h at room temperature. The reaction was quenched with saturated $NaHSO_3$ and the product was extracted with methylene chloride. The methylene chloride layer was washed with brine, dried over $Na_2SO_4$, and evaporated in vacuum to give the crude product (100 g, yield 92%). $^1$H NMR (300 MHz, CDCl$_3$): δ 7.46 (s, 1H), 7.13-6.95 (d, 1H), 6.68-6.64 (d, 1H), 4.00 (br, 2H), 2.21 (s, 3H). MS: m/z 234 [M+1]$^+$.

Step 2: Preparation of 1-bromo-2-iodo-4-methylbenzene

2-Iodo-4-methylaniline (100 g, 450 mmol) was suspended in the mixture of water (200 mL) and HBr (48%, 300 mL). The mixture was refluxed for 15 min. Then the mixture was cooled to 0° C., and $NaNO_2$ (31.05 g, 0.45 mol) in water (150 ml) was added dropwise at such a rate that the temperature did not exceed 5° C. The diazonium solution wad stirred for a further 30 min at 0-5° C. and then added slowly to a stirred mixture of CuBr (64.5 g, 0.45 mol) in HBr (48%, 250 mL) and water (250 ml) at room temperature. The mixture was poured into ice and extracted with $CH_2Cl_2$ (500 ml×3). The methylene chloride layer was washed with brine, dried over $Na_2SO_4$, and evaporated in vacuum to give the crude product (109 g, yield 81.8%). It can be further purified by column chromatography eluting with petroleum ether. MS: 297 [M+1]$^+$.

Step 3: Preparation of 3-(2-bromo-5-methylphenyl)pentan-3-ol

To a solution of 1-bromo-2-iodo-4-methylbenzene (28 g, 94 mmol) in THF (10 ml) at −10° C. under nitrogen was slowly added i-PrMgBr (47 ml, 94 mmol). The reaction mixture was stirred for 1 h at −10° C. Then the reaction mixture was cooled to −30° C., and pentan-3-one (8.1 g, 94 mmol) was added dropwise. The reaction mixture was stirred for 1 h at −30° C. under nitrogen and then warmed to rt and stirred for additional 2 h. Then the reaction mixture was quenched with 2N HCl solution and extracted with EA. The combined organic layers were washed with brine, dried over $Na_2SO_4$, filtered and concentrated under reduced pressure. The residue was purified by column chromatography over silica gel eluted with PE:EA (10:0 to 5:1) to give the desired compound (6.5 g, yield 26.9%) as colorless oil. $^1$H NMR (300 MHz, CDCl$_3$): δ 7.52-7.50 (d, 1H), 7.43-7.40 (d, 1H), 6.95-6.92 (d, 1H), 2.48-2.40 (q, 2H), 2.31 (s, 3H), 1.86-1.78 (q, 2H), 0.77-0.71 (m, 6H). MS: m/z=257 and 259 [M+1]$^+$.

Step 4: Preparation of 3,3-diethyl-5-methylbenzo[c][1,2]oxaborol-1(3H)-ol

To a solution of 3-(2-bromo-5-methylphenyl)pentan-3-ol (6.5 g, 25.2 mmol) in THF (150 ml) at −78° C. was slowly added n-BuLi (30.24 ml, 75.6 mmol). The reaction mixture was warmed to rt and stirred for 2 h. After being cooled to −78° C., trimethyl borate (5.23 g, 50.4 mmol) was added dropwise and the reaction mixture was warmed to rt, stirred for 10 h under nitrogen and quenched with 2N HCl (50 ml). The mixture was extracted with EA (40 ml×3). The combined organic layers were washed with water and brine, dried over $Na_2SO_4$, filtered and concentrated under reduced pressure. The residue was purified by column chromatography over silica gel eluted with PE:EA (10:1 to 1:1) to give the product (2.0 g, yield 38.9%) as a white solid. $^1$H NMR (300 MHz, DMSO-$d_6$): δ 8.87 (s, 1H), 7.52-7.47 (d, 1H), 7.11-7.06 (m, 2H), 2.35 (s, 3H), 1.88-1.68 (m, 4H), 0.60-0.45 (m, 6H). MS: m/z=205 [M+1]$^+$.

Step 5: Preparation of 3,3-diethyl-1-hydroxy-1,3-dihydrobenzo[c][1,2]oxaborole-5-carbaldehyde To a solution of 3,3-diethyl-5-methylbenzo[c][1,2]oxaborol-1(3H)-ol (2.0 g, 9.8 mmol) in CCl$_4$ (25 ml) at rt was added benzoyl peroxide (237 mg, 0.98 mmol) followed by NBS (3.489 g, 19.6 mmol). The reaction mixture was refluxed for 16 h, cooled to rt and treated with aqueous $Na_2CO_3$. The aqueous layer was acidified with 3N HCl to pH=3 and extracted with EA (50 ml×3). The organic layer was washed with brine, dried over $Na_2SO_4$, filtered and concentrated under reduced pressure to give the desired product (1.2 g, yield 56%) as white solid. $^1$H NMR (300 MHz, DMSO-$d_6$): δ

10.06 (s, 1H), 9.30 (s, 1H), 7.85 (m, 3H), 1.86 (m, 4H), 0.55 (m, 6H). MS: m/z=219 [M+1]⁺.

Step 5: Preparation of 3,3-diethyl-1-hydroxy-1,3-dihydrobenzo[c][1,2]oxaborole-5-carbaldehyde oxime To a mixture of 3,3-diethyl-1-hydroxy-1,3-dihydrobenzo[c][1,2]oxaborole-5-carb-aldehyde (1.1 g, 5.04 mmol) and NH₂OH.HCl (420 mg, 6.05 mmol) in THF (20 ml) and H₂O (5 ml) at rt was added NaOAc (578 mg, 7.06 mmol). The mixture was stirred at rt for 16 h, diluted with H₂O and extracted with EA (20 ml×2). The combined organic layers were washed with aqueous NaHCO₃ and brine, dried over Na₂SO₄, filtered and concentrated under reduced pressure. The residue was purified by column chromatography over silica gel eluted with PE:EA (10:1 to 1:1) to give the product (600 mg, yield 51%) as white solid: MS: m/z=234 [M+1]⁺.

Step 6 and 7: 5-(5-(3,5-dichlorophenyl)-5-(trifluoromethyl)-4,5-dihydroisoxazol-3-yl)-3,3-diethyl-benzo[c][1,2]oxaborol-1(3H)-ol To a solution of 3,3-diethyl-1-hydroxy-1,3-dihydrobenzo[c][1,2]oxaborole-5-carbaldehyde oxime (251 mg, 1.07 mmol) in DMF (15 ml) at rt was added NCS (151 mg, 1.13 mmol). The reaction mixture was warmed to 45° C., stirred for 1.5 h and cooled to −10° C. To this mixture was successively added 1,3-dichloro-5-(3,3,3-trifluoroprop-1-en-2-yl)benzene (516 mg, 2.15 mmol) and TEA (326.3 mg, 3.23 mmol) below −10° C. The mixture was stirred at this temperature for 2 h, poured into ice-water and extracted with EA (40 ml×2). The combined organic layers were washed with aqueous NaHCO₃ and brine, dried over Na₂SO₄, filtered and concentrated under reduced pressure. The residue was purified by column chromatography over silica gel eluted with PE:EA (10:1 to 5:1) to give the desired title compound 5-(5-(3,5-dichlorophenyl)-5-(trifluoromethyl)-4,5-dihydroisoxazol-3-yl)-3,3-diethylbenzo[c][1,2]oxaborol-1(3H)-ol (180 mg, yield 35.5%) as white solid. ¹H NMR (300 MHz, DMSO-d₆): δ 9.22 (s, 1H), 7.85-7.45 (m, 6H), 4.48-4.22 (m, 2H), 2.00-1.70 (m, 4H), 0.68-0.42 (m, 6H) ppm. MS: m/z=472 [M+1]⁺.

37. 5-(5-(3,5-Dichlorophenyl)-5-(trifluoromethyl)-4,5-dihydroisoxazol-3-yl)-1H-spiro[benzo[c][1,2]oxaborole-3,1'-cyclopentan]-1-ol

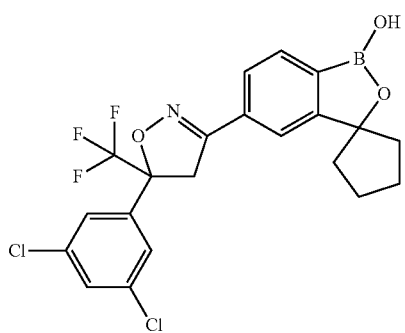 [SMILES: OB1OC2(CCCC2)c2cc(C3=NOC(c4cc(Cl)cc(Cl)c4)(C(F)(F)F)C3)ccc21]

The title compound was prepared by using the same method as described for 5-(5-(3,5-dichlorophenyl)-5-(trifluoromethyl)-4,5-dihydroisoxazol-3-yl)-3,3-diethyl-benzo[c][1,2]oxaborol-1(3H)-ol with cyclopentanone to replace 3-pentanone. It was obtained as a white solid. ¹H NMR (300 MHz, DMSO-d₆): δ 9.20 (s, 1 H), 7.80 (t, J=1.8 Hz, 1 H), 7.72 (s, 3 H), 7.61 (d, J=1.5 Hz, 2 H), 4.44 (d, J=18.3 Hz, 1 H), 4.31 (d, J=18.3 Hz, 1 H), 2.11-1.71 (m, 8 H) ppm.

38. 5-(5-(3,5-Dichlorophenyl)-5-(trifluoromethyl)-4,5-dihydroisoxazol-3-yl)-1H-spiro[benzo[c][1,2]oxaborole-3,1'-cyclohexan]-1-ol

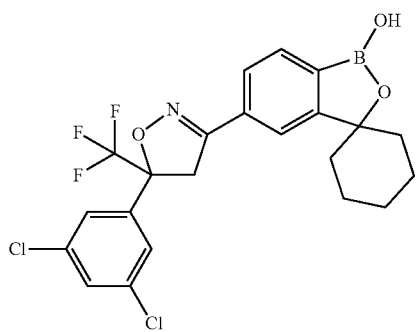 [SMILES: OB1OC2(CCCCC2)c2cc(C3=NOC(c4cc(Cl)cc(Cl)c4)(C(F)(F)F)C3)ccc21]

The title compound was prepared by using the same method as described for 5-(5-(3,5-dichlorophenyl)-5-(trifluoromethyl)-4,5-dihydroisoxazol-3-yl)-3,3-diethyl-benzo[c][1,2]oxaborol-1(3H)-ol with cyclohexanone to replace 3-pentanone. It was obtained as a white solid. ¹H NMR (300 MHz, DMSO-d₆): δ 9.22 (s, 1H), 7.82-7.61 (m, 6H), 4.47-4.27 (m, 2H), 1.68-0.84 (m, 10H). MS: m/z=484 [M+1]⁺.

39. 5-(5-(3,5-Dichlorophenyl)-5-(trifluoromethyl)-4,5-dihydroisoxazol-3-yl)-4-fluoro-3,3-dimethylbenzo[c][1,2]oxaborol-1(3H)-ol

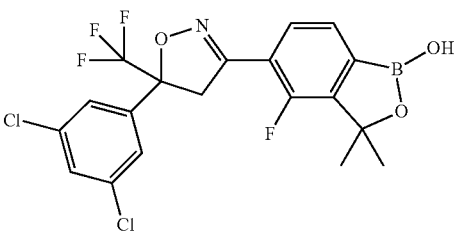 [SMILES: CC1(C)OB(O)c2ccc(C3=NOC(c4cc(Cl)cc(Cl)c4)(C(F)(F)F)C3)c(F)c21]

Step 1: Preparation of methyl 6-bromo-2-fluoro-3-methylbenzoic acid

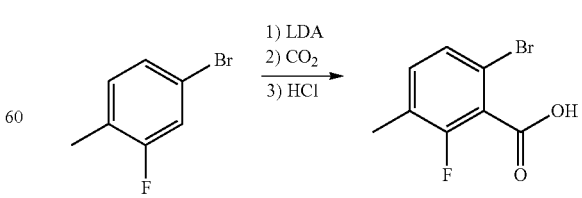

To a solution of 4-bromo-2-fluoro-1-methylbenzene (21.9 g, 116 mmol) in THF (100 mL) was added lithium diisopropylamide (LDA) (2 M solution in THF, 69 mL, 139 mmol) at -78° C. After being stirred at -78° C. for 1 h, the reaction was treated with excess solid carbon dioxide, and stirred while the reaction temperature slowly rose to room temperature. The mixture was concentrated and then partitioned between 4N NaOH and ethyl acetate. The aqueous phase was adjusted to pH 2 with 2N HCl and then extracted three times with ethyl acetate. The combined extracts were washed with water and brine, dried over with anhydrous Na$_2$SO$_4$, filtered and concentrated under reduced pressure. The residue was purified by column chromatography on silica gel eluted with EA to give methyl 6-bromo-2-fluoro-3-methylbenzoic acid (23.3 g, 86.2%) as a white solid.

Step 2: Preparation of methyl 6-bromo-2-fluoro-3-methylbenzoate

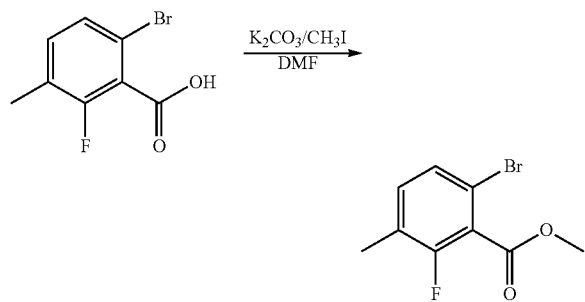

To a suspension of 6-bromo-2-fluoro-3-methylbenzoic acid (9.26 g, 39.74 mmol) and K$_2$CO$_3$ (5.48 g, 39.74 mmol) in DMF (50 mL) was added dropwise MeI (3.47 g, 59.61 mmol) at room temperature. The mixture was stirred for 3 h until TLC analysis indicated the disappearance of the acid. The mixture was extracted three times with ethyl acetate. The combined extracts were washed with water and brine, dried over with anhydrous Na$_2$SO$_4$, filtered and concentrated under reduced pressure. The residue was purified by column chromatography on silica gel eluted with PE-EA (20:1) to give 6-bromo-2-fluoro-3-methylbenzoate (9.3 g, 94.9%) as light yellow oil. $^1$H NMR (500 MHz, DMSO-d$_6$) δ 7.467 (d, J=8.0 Hz, 1H), 7.405 (t, J=8.0 Hz, 1H), 3.910 (s, 3H), 2.229 (s, 3H) ppm.

Step 3: Preparation of 2-(6-bromo-2-fluoro-3-methylphenyl)propan-2-ol

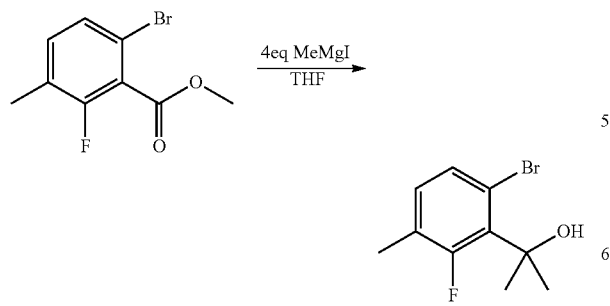

To a solution of 6-bromo-2-fluoro-3-methylbenzoate (9.3 g, 37.65 mmol) in dry THF (100 mL) was added dropwise MeMgI (3M solution in ethyl ether, 50 mL, 150.6 mmol) at 0° C. under argon and then stirred at room temperature for 1 h.

The reaction mixture was quenched with saturated NH$_4$Cl and the mixture was extracted three times with ethyl acetate. The combined extracts were washed with water and brine, dried over with anhydrous Na$_2$SO$_4$, filtered and concentrated under reduced pressure. The residue was purified by column chromatography on silica gel eluted with PE-EA (10:1) to give 2-(6-bromo-2-fluoro-3-methylphenyl)propan-2-ol (2.7 g, 29%) as a light yellow solid. $^1$H NMR (500 MHz, CDCl$_3$) δ 7.197 (d, J=8.0 Hz, 1H), 6.834 (t, J=8.0 Hz, 1H), 3.395 (s, 1H), 2.126 (s, 3H), 1.675 (d, J=4.0 Hz, 6H) ppm.

Step 4: Preparation of 1-bromo-2-(2-(ethoxymethoxy)propan-2-yl)-3-fluoro-4-methylbenzene

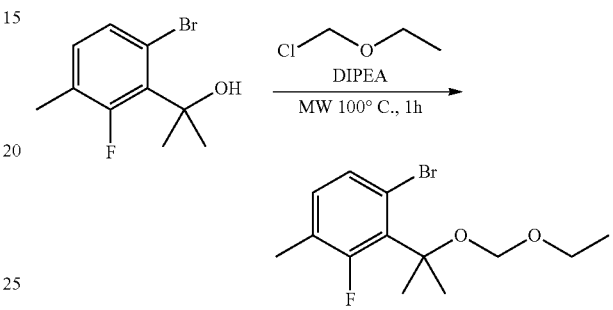

To a solution of 2-(6-bromo-2-fluoro-3-methylphenyl)propan-2-ol (2.15 g, 8.7 mmol) in DIPEA (4 mL) was added (chloromethoxy)ethane (2.5 g, 26.1 mmol). The reaction mixture was heated at 100° C. in a microware for 1 h. Water (100 mL) was added and the mixture was extracted three times with ethyl acetate. The combined extracts were washed with water and brine, dried over with anhydrous Na$_2$SO$_4$, filtered and concentrated under reduced pressure. The residue was purified by column chromatography on silica gel eluted with PE-EA (10:1) to give 2-(6-bromo-2-fluoro-3-methylphenyl)propan-2-ol (2.52 g, 95%) as colorless oil. $^1$H NMR (500 MHz, CDCl$_3$) δ 7.243 (d, J=8.0 Hz, 1H), 6.831 (t, J=8.0 Hz, 1H), 4.592 (s, 2H), 3.556 (q, J=7.0 Hz, 2H), 2.113 (s, 3H), 1.733 (d, J=5.5 Hz, 6H), 1.095 (t, J=7.0 Hz, 3H) ppm.

Step 5: Preparation of 2-(2-(2-(ethoxymethoxy)propan-2-yl)-3-fluoro-4-methylphenyl)-4,4,5,5-tetramethyl-1,3,2-dioxaborolane

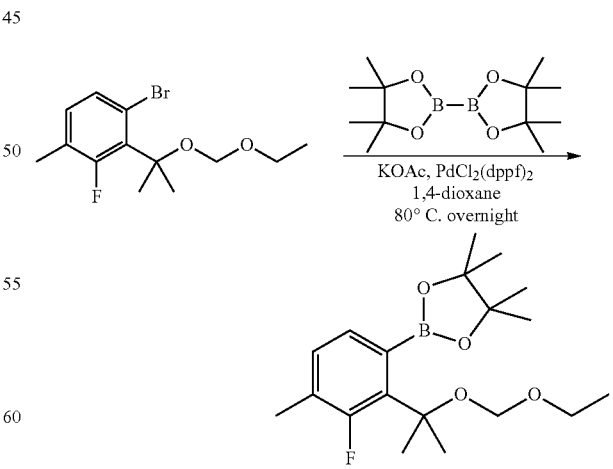

A mixture of 1-bromo-2-(2-(ethoxymethoxy)propan-2-yl)-3-fluoro-4-methylbenzene (4.48 g, 14.7 mmol), bis(pinacolato)diboron (11.2 g, 44.2 mmol), Pd(dppf)Cl$_2$ (539 mg, 0.7 mmol) and KOAc (4.33 g, 44.2 mmol) in 1,4-dioxane (60 mL) was stirred at 80° C. overnight under argon. Water (100 mL) was added and the mixture was extracted three times with ethyl acetate. The combined extracts were washed with water and brine, dried over with anhydrous Na₂SO₄, filtered and concentrated under reduced pressure. The residue was purified by column chromatography on silica gel eluted with PE-EA (10:1) to give 2-(2-(2-(ethoxymethoxy)propan-2-yl)-3-fluoro-4-methylphenyl)-4,4,5,5-tetramethyl-1,3,2-dioxaborolane as a crude white solid.

Step 6: Preparation of 4-fluoro-3,3,5-trimethylbenzo[c][1,2]oxaborol-1(3H)-ol

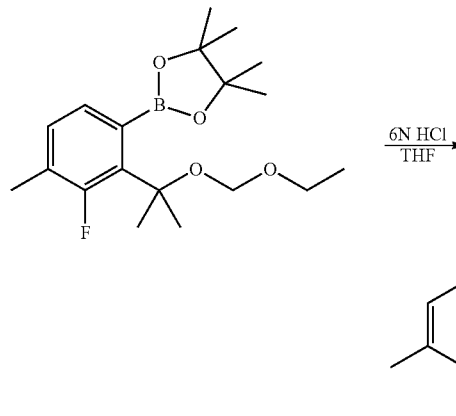

To a solution of the crude compound 2-(2-(2-(ethoxymethoxy)propan-2-yl)-3-fluoro-4-methylphenyl)-4,4,5,5-tetramethyl-1,3,2-dioxaborolane (5.17 g, 14.7 mmol) in THF (147 mL) was added 6 N HCl (147 mL). The reaction mixture was stirred at room temperature overnight, and the resulting mixture was extracted three times with ethyl acetate. The combined extracts were washed with water and brine, dried over with anhydrous Na₂SO₄, filtered and concentrated under reduced pressure. The residue was purified by column chromatography on silica gel eluted with PE-EA (10:1) to give 4-fluoro-3,3,5-trimethylbenzo[c][1,2]oxaborol-1(3H)-ol (1.52 g, 53.8% yield over 2 steps) as a white solid. ¹H NMR (500 MHz, CDCl₃) δ 7.339 (d, J=7.5 Hz, 1H), 7.200 (t, J=6.5 Hz, 1H), 5.652 (s, 1H), 2.330 (s, 3H), 1.642 (s, 6H) ppm.

Step 7: Preparation of 4-fluoro-1-hydroxy-3,3-dimethyl-1,3-dihydrobenzo[c][1,2]oxaborole-5-carbaldehyde

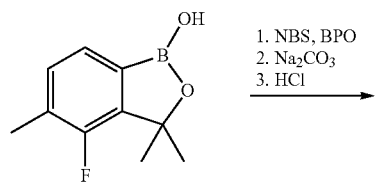

To a solution of 4-fluoro-3,3,5-trimethylbenzo[c][1,2]oxaborol-1(3H)-ol (970 mg, 5 mmol) in CCl₄ (50 mL) at rt was added benzoyl peroxide (121 mg, 0.5 mmol) followed by NBS (1.958 g, 11.0 mmol). The reaction mixture was heated under reflux for 16 h, cooled to rt and treated with Na₂CO₃. The aqueous layer was acidified with 3 N HCl to pH 3 and extracted three times with ethyl acetate. The combined extracts were washed with water and brine, dried over with anhydrous Na₂SO₄, filtered and concentrated under reduced pressure. The residue was purified by column chromatography on silica gel eluted with PE-EA (2:1) to give 4-fluoro-1-hydroxy-3,3-dimethyl-1,3-dihydrobenzo[c][1,2]oxaborole-5-carbaldehyde (688 mg, 68%) as a light yellow solid.

Step 8: Preparation of 4-fluoro-1-hydroxy-3,3-dimethyl-1,3-dihydrobenzo[c][1,2]oxaborole-5-carbaldehyde oxime

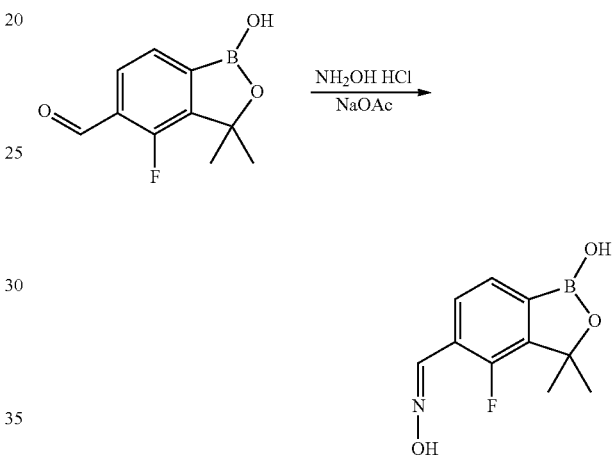

To a solution of 4-fluoro-1-hydroxy-3,3-dimethyl-1,3-dihydrobenzo[c][1,2]oxaborole-5-carbaldehyde (136 mg, 0.7 mmol) and NH₂OH.HCl (58.5 mg, 0.84 mmol) in THF (4 mL) and H₂O (1 mL) at rt was added NaOAc (80.5 mg, 0.98 mmol). The reaction mixture was stirred for 2 h and diluted with H₂O. The mixture was extracted three times with ethyl acetate and the organic layer was separated. The organic solution was washed with brine, dried over Na₂SO₄, filtered and concentrated under reduced pressure to give crude compound 4-fluoro-1-hydroxy-3,3-dimethyl-1,3-dihydrobenzo[c][1,2]oxaborole-5-carbaldehyde oxime as a light yellow solid. It was used in next step without further purification.

Step 9: Preparation of 4-fluoro-N,1-dihydroxy-3,3-dimethyl-1,3-dihydrobenzo[c][1,2]oxaborole-5-carbimidoyl chloride

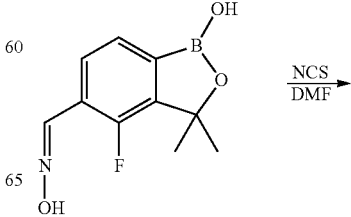

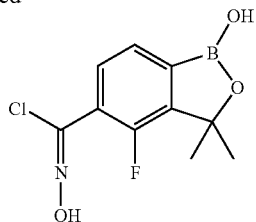

To a solution of the crude compound 6-fluoro-1-hydroxy-3,3-dimethyl-1,3-dihydrobenzo[c][1,2]oxaborole-5-carbaldehyde oxime (163 mg, 0.7 mmol) in DMF (4.0 mL) at rt was added NCS (111 mg, 0.84 mmol). The reaction mixture was stirred at 40° C. for up to 2 h. The mixture was cooled to rt, poured into ice-water and extracted three times with ethyl acetate. The organic solution was washed with brine, dried over Na$_2$SO$_4$, filtered and concentrated under reduced pressure to give the crude compound 4-fluoro-N,1-dihydroxy-3,3-dimethyl-1,3-dihydrobenzo[c][1,2]oxaborole-5-carbimidoyl chloride as light yellow oil. It was used in next step without further purification.

Step 10: Preparation of 5-(5-(3,5-dichlorophenyl)-5-(trifluoromethyl)-4,5-dihydro isoxazol-3-yl)-4-fluoro-3,3-dimethylbenzo[c][1,2]oxaborol-1(3H)-ol

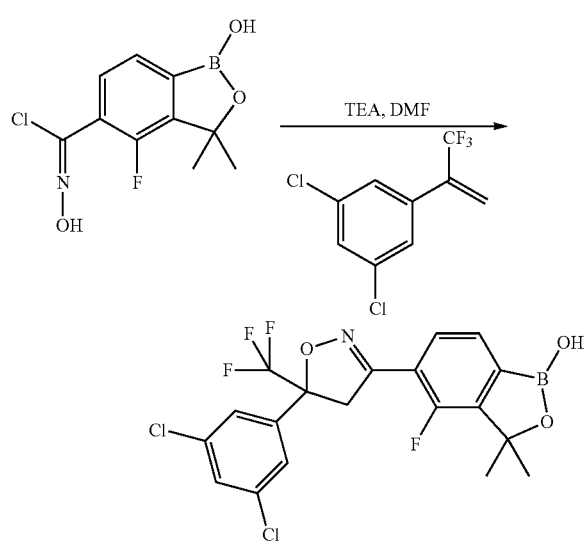

To a solution of the crude compound 4-fluoro-N,1-dihydroxy-3,3-dimethyl-1,3-dihydrobenzo[c][1,2]oxaborole-5-carbimidoyl chloride (180 mg. 0.70 mmol) and 1,3-dichloro-5-(3,3,3-trifluoroprop-1-en-2-yl)benzene (203 mg, 0.84 mmol) in DMF (5 mL) at rt was added TEA (117 μL, 0.84 mmol). The reaction mixture was stirred for 12 h, poured into ice-water and extracted three times with ethyl acetate. The organic layer was washed with brine, dried over Na$_2$SO$_4$, filtered and concentrated under reduced pressure. The residue was purified by prep-TLC eluted with PE-EA (3:2) and then purified by combiflash to give the title compound 5-(5-(3,5-dichlorophenyl)-5-(trifluoromethyl)-4,5-dihydroisoxazol-3-yl)-4-fluoro-3,3-dimethylbenzo[c][1,2]oxaborol-1(3H)-ol [80 mg; yield 24.8% over the last 3 steps] as a white solid. $^1$H NMR (500 MHz, DMSO-d$_6$): δ 9.479 (s, 1H), 7.810 (t, J=1.5 Hz, 1H), 7.753 (t, J=7.5 Hz, 1H), 7.671 (d, J=1.5 Hz, 2H), 7.582 (d, J=7.5 Hz, 1H), 4.376 (d, J=18.0 Hz, 1H), 4.270 (d, J=18.0 Hz, 1H), 1.55 (s, 6H) ppm; HPLC purity: 100% at 220 nm and 100% at 254 nm; MS: m/z=462.0 (M+1, ESI+).

40. 4-Fluoro-3,3-dimethyl-5-(5-(3,4,5-trichlorophenyl)-5-(trifluoromethyl)-4,5-dihydro isoxazol-3-yl)benzo[c][1,2]oxaborol-1(3H)-ol

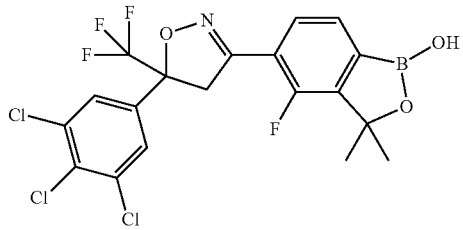 [SMILES: CC1(C)OB(O)c2ccc(C3=NOC(c4cc(Cl)c(Cl)c(Cl)c4)(C(F)(F)F)C3)c(F)c21]

The title compound was synthesized by the following scheme:

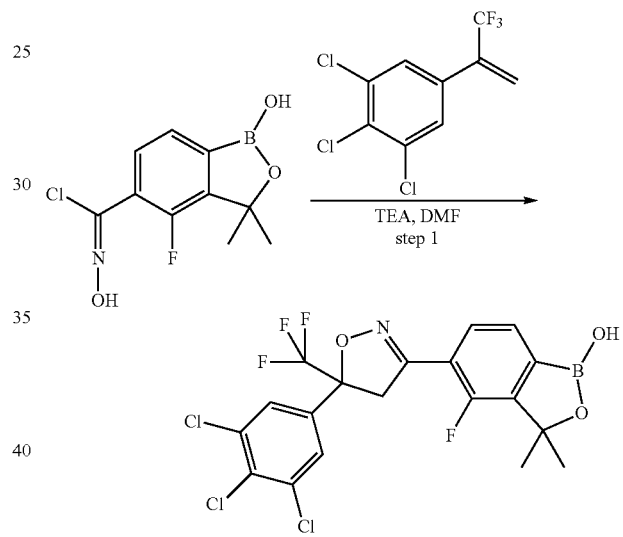

Step 1: Preparation of 4-fluoro-3,3-dimethyl-5-(5-(3,4,5-trichlorophenyl)-5-(trifluoro-methyl)-4,5-dihydroisoxazol-3-yl)benzo[c][1,2]oxaborol-1(3H)-ol To a solution of the crude compound 4-fluoro-N,1-dihydroxy-3,3-dimethyl-1,3-dihydrobenzo[c][1,2]oxaborole-5-carbimidoyl chloride (257 mg, 1 mmol) and 1,2,3-trichloro-5-(3,3,3-trifluoroprop-1-en-2-yl)benzene (327 mg, 1.2 mmol) in DMF (5 mL) at rt was added TEA (167 μL, 1.2 mmol). The reaction mixture was stirred for 12 h, poured into ice-water and extracted three times with ethyl acetate. The organic layer was washed with brine, dried over Na$_2$SO$_4$, filtered and concentrated under reduced pressure. The residue was purified by prep-TLC eluted with PE-EA (3:2) and then purified by combiflash to give the title compound 4-fluoro-3,3-dimethyl-5-(5-(3,4,5-trichlorophenyl)-5-(trifluoromethyl)-4,5-dihydroisoxazol-3-yl)benzo[c][1,2]oxaborol-1(3H)-ol (80 mg; yield 16.1% over 3 steps from the aldehyde) as a white solid. $^1$H NMR (500 MHz, DMSO-d$_6$): δ 9.461 (s, 1H), 7.891 (s, 2H), 7.754 (t, J=7.0 Hz, 1H), 7.586 (d, J=7.5 Hz, 1H), 4.377 (d, J=18.5 Hz, 1H), 4.291 (d, J=18.5 Hz, 1H), 1.55 (s, 6H) ppm; HPLC purity: 100% at 220 nm and 100% at 254 nm; MS: m/z=496.0 (M+1, ESI+).

41. 5-(5-(3,5-dichlorophenyl)-5-(trifluoromethyl)-4,5-dihydroisoxazol-3-yl)-6-fluoro-3,3-dimethylbenzo[c][1,2]oxaborol-1(3H)-ol

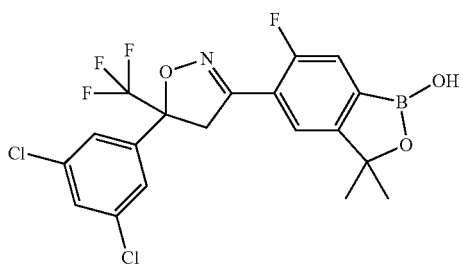 [SMILES: CC1(C)OB(O)c2cc(F)c(C3=NOC(c4cc(Cl)cc(Cl)c4)(C(F)(F)F)C3)cc21]

Step 1: Preparation of 4-fluoro-5-methyl-2-nitrobenzoic acid

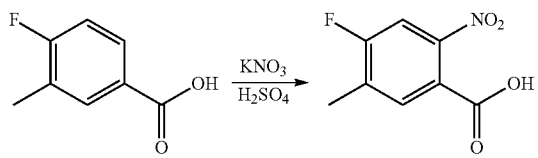

To a solution of 4-fluoro-3-methylbenzoic acid (3.7 g, 24 mmol) in conc. $H_2SO_4$ (50 mL) at 0° C. was added $KNO_3$ (3.6 g, 36 mmol) in one portion and the mixture was stirred at rt for 2 h. The reaction mixture was poured into ice water (200 mL) and extracted with DCM (100 mL×2). The organic layer was washed with brine, dried and concentrated to give the crude 4-fluoro-5-methyl-2-nitrobenzoic acid (5 g) as white solid. It was used in the next step without further purification.

Step 2: Preparation of methyl 4-fluoro-5-methyl-2-nitrobenzoate

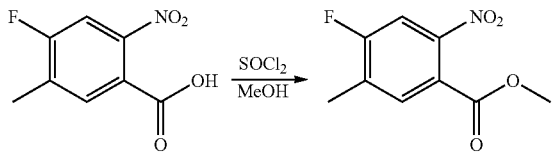

To a solution of the crude 4-fluoro-5-methyl-2-nitrobenzoic acid (5 g) in MeOH (50 mL) was slowly added $SOCl_2$ (3.5 mL, 48 mmol) dropwise and the resulting mixture was refluxed overnight. Then the solvent was removed to give crude methyl 4-fluoro-5-methyl-2-nitrobenzoate (5 g) as a white solid. It was used in the next step without further purification.

Step 3: Preparation of methyl 2-amino-4-fluoro-5-methylbenzoate

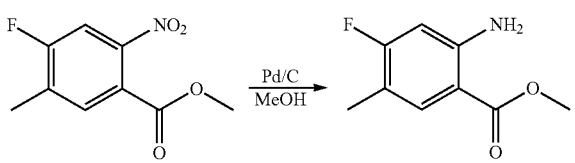

The solution of crude methyl 4-fluoro-5-methyl-2-nitrobenzoate (5 g) in MeOH (50 mL) was hydrogenated using 10% Pd/C (0.5 g) as catalyst at atmospheric pressure overnight. The catalyst was removed by filtration, and the solvent was evaporated at reduced pressure. The residue was purified by column chromatography on silica gel eluted with PE-EA (8:1) to give methyl 2-amino-4-fluoro-5-methylbenzoate (2.21 g, yield 50% over three steps) as a white solid. $^1H$ NMR (500 MHz, $CDCl_3$) δ 7.715 (d, J=9.0 Hz, 1H), 6.339 (d, J=11.5 Hz, 1H), 3.873 (s, 3H), 2.154 (s, 3H) ppm.

Step 4: Preparation of methyl 2-bromo-4-fluoro-5-methylbenzoate

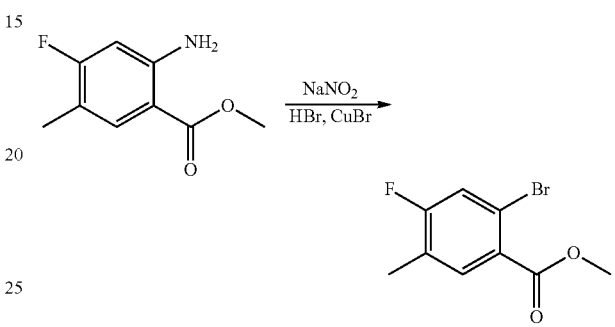

To the suspension of methyl 2-amino-4-fluoro-5-methylbenzoate (2.2 g, 12 mmol) in 48% hydrobromic acid (80 mL) was added an aqueous solution (32 mL) of sodium nitrite (828 mg, 12 mmol) at 0° C., and the resulting solution was stirred for 30 min. Copper (I) bromide (1.72 g, 12 mmol) was added to the solution at 0° C. and the resulting reaction mixture was stirred at r.t for 1 h. After addition of ethyl acetate (200 mL), the reaction mixture was washed with water (200 mL×2), dried over sodium sulfate, filtered and concentrated under reduced pressure. The residue was purified by column chromatography on silica gel eluted with PE-EA (10:1) to give methyl 2-bromo-4-fluoro-5-methylbenzoate (2.2 g, yield 74%) as colorless oil. $^1H$ NMR (500 MHz, $CDCl_3$) δ 7.655 (d, J=8.0 Hz, 1H), 7.257 (d, J=8.5 Hz, 1H), 3.837 (s, 3H), 2.177 (s, 3H) ppm.

Step 5: Preparation of 2-(2-bromo-4-fluoro-5-methylphenyl)propan-2-ol

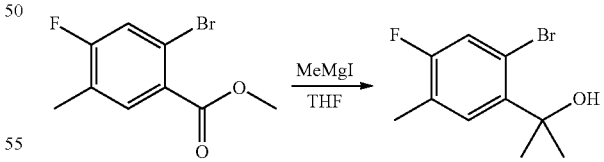

To a solution of methyl 2-bromo-4-fluoro-5-methylbenzoate (4.66 g, 18.87 mmol) in dry THF (90 mL) was added dropwise MeMgI (31 mL, 94.33 mmol) at 0° C. under argon and then stirred at rt for 16 h. The reaction mixture was quenched with saturated $NH_4Cl$ and extracted with EA (200 mL×2). The combined organic layers were washed with brine, dried over $Na_2SO_4$, filtered and concentrated under reduced pressure. The residue was purified by column chromatography on silica gel eluted with PE-EA (20:1) to give 2-(2-bromo-4-fluoro-5-methylphenyl)propan-2-ol (3.24 g, 70%) as colorless oil. ¹H NMR (500 MHz, CDCl₃) δ 7.427 (d, J=8.5 Hz, 1H), 7.189 (d, J=11.0 Hz, 1H), 2.168 (s, 3H), 1.651 (s, 6H) ppm.

Step 6: Preparation of 1-bromo-2-(2-(ethoxymethoxy)propan-2-yl)-5-fluoro-4-methylbenzene

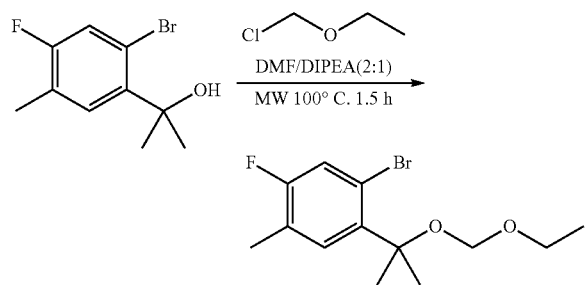

To a solution of 2-(2-bromo-4-fluoro-5-methylphenyl)propan-2-ol (2.0 g, 8.1 mmol) in DMF:DIPEA (2:1, 9 mL) was added (chloromethoxy)ethane (1.53 g, 16.2 mmol). The reaction mixture was heated at 100° C. in microware equipment for 1.5 h. Water (200 mL) was added and the mixture was extracted with DCM (200 mL×2). The combined organic layers were washed with brine, dried over Na₂SO₄, filtered and concentrated under reduced pressure. The residue was purified by column chromatography on silica gel eluted with PE-EA (30:1) to give 1-bromo-2-(2-(ethoxymethoxy)propan-2-yl)-5-fluoro-4-methylbenzene (2.2 g, 89%) as colorless oil. ¹H NMR (500 MHz, CDCl₃) δ 7.208-7.234 (m, 2H), 4.572 (s, 2H), 3.594 (q, J=7.0 Hz, 2H), 2.149 (s, 3H), 1.665 (s, 6H), 1.115 (t, J=7.0 Hz, 3H) ppm.

Step 7: Preparation of 2-(2-(2-(ethoxymethoxy)propan-2-yl)-5-fluoro-4-methylphenyl)-4,4,5,5-tetramethyl-1,3,2-dioxaborolane

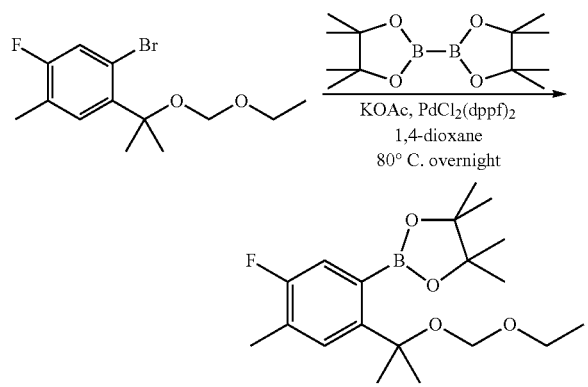

A mixture of 1-bromo-2-(2-(ethoxymethoxy)propan-2-yl)-5-fluoro-4-methylbenzene (2.3 g, 7.56 mmol), bis(pinacolato)diboron (2.1 g, 8.32 mmol), Pd(dppf)Cl₂ (127 mg, 0.15 mmol) and KOAc (1.1 g, 11.34 mmol) in 1,4-dioxane (60 mL) was stirred at 80° C. overnight under argon. Water (200 mL) was added and the mixture was extracted with DCM (200 mL×2). The combined organic layers were washed with brine, dried over Na₂SO₄, filtered and concentrated under reduced pressure. The residue was purified by column chromatography on silica gel eluted with PE-EA (20:1) to give 2-(2-(2-(ethoxymethoxy)propan-2-yl)-5-fluoro-4-methylphenyl)-4,4,5,5-tetramethyl-1,3,2-dioxaborolane (2.35 g, 88%) as a white solid.

Step 8: Preparation of 6-fluoro-3,3,5-trimethylbenzo[c][1,2]oxaborol-1(3H)-ol

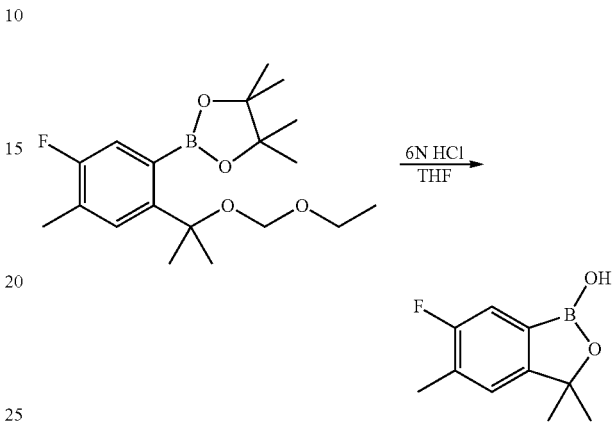

To a solution of 2-(2-(2-(ethoxymethoxy)propan-2-yl)-5-fluoro-4-methylphenyl)-4,4,5,5-tetramethyl-1,3,2-dioxaborolane (2.35 g, 6.68 mmol) in THF (67 mL) was added 6 N HCl (67 mL). The reaction mixture was stirred at room temperature overnight, and extracted with DCM (200 mL×2). The combined organic layers were washed with brine, dried over Na₂SO₄, filtered and concentrated under reduced pressure. The residue was purified by column chromatography on silica gel eluted with PE-EA (from 10:1 to 3:1) to give 6-fluoro-3,3,5-trimethylbenzo[c][1,2]oxaborol-1(3H)-ol (835 mg, 64%) as a white solid. ¹H NMR (500 MHz, CDCl₃) δ 7.189 (d, J=8.0 Hz, 1H), 6.995 (d, J=6.5 Hz, 1H), 5.950 (s, 1H), 2.266 (s, 3H), 1.472 (s, 6H) ppm.

Step 9: Preparation of 6-fluoro-1-hydroxy-3,3-dimethyl-1,3-dihydrobenzo[c][1, 2]-oxaborole-5-carbaldehyde

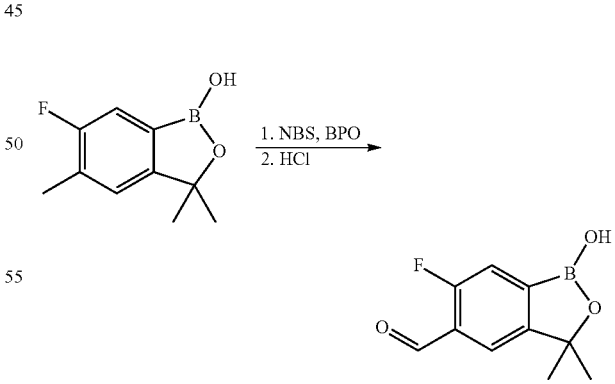

To a solution of 6-fluoro-3,3,5-trimethylbenzo[c][1,2]oxaborol-1(3H)-ol (388 mg, 2 mmol) in CCl₄ (60 mL) at rt was added benzoyl peroxide (48.4 mg, 0.2 mmol) followed by NBS (783 mg, 4.4 mmol). The reaction mixture was heated under reflux for 16 h, cooled to rt and treated with Na₂CO₃. The aqueous layer was acidified with 3 N HCl to pH of 3 and extracted with DCM (60 mL×3). The organic layer was dried over Na$_2$SO$_4$, filtered and concentrated under reduced pressure to give 6-fluoro-1-hydroxy-3,3-dimethyl-1,3-dihydrobenzo[c][1,2]oxaborole-5-carbaldehyde (378 mg, 91%) as a pale yellow solid. $^1$H NMR (500 MHz, CDCl$_3$) δ 10.369 (s, 1H), 7.687 (d, J=5.5 Hz, 1H), 7.409 (d, J=8.0 Hz, 1H), 2.715 (s, 3H), 1.484 (s, 6H) ppm.

Step 10: Preparation of 6-fluoro-1-hydroxy-3,3-dimethyl-1,3-dihydrobenzo[c][1,2]oxaborole-5-carbaldehyde oxime

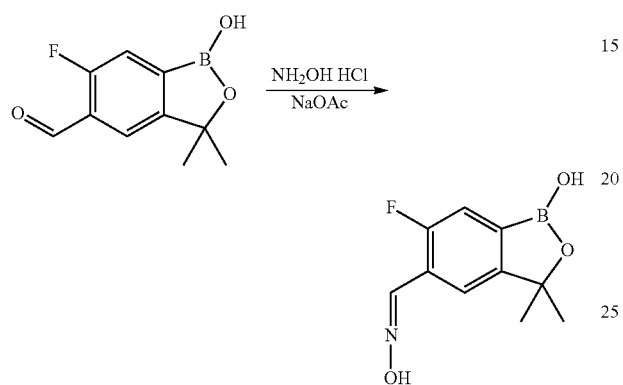

To a solution of 6-fluoro-1-hydroxy-3,3-dimethyl-1,3-dihydrobenzo[c][1,2]oxaborole-5-carbaldehyde (200 mg, 0.96 mmol) and NH$_2$OH.HCl (79.5 mg, 1.15 mmol) in THF (4 mL) and H$_2$O (1 mL) at rt was added NaOAc (110 mg, 1.34 mmol). The reaction mixture was stirred for 2 h and diluted with H$_2$O. The mixture was extracted with DCM (60 mL×3) and the organic layer was separated. The organic solution was washed with brine, dried over Na$_2$SO$_4$, filtered and concentrated under reduced pressure to give crude compound 6-fluoro-1-hydroxy-3,3-dimethyl-1,3-dihydrobenzo[c][1,2] oxaborole-5-carbaldehyde oxime as a light yellow solid. It was used in next step without further purification.

Step 11: Preparation of 6-fluoro-N,1-dihydroxy-3,3-dimethyl-1,3-dihydrobenzo[c][1,2]oxaborole-5-carbimidoyl chloride

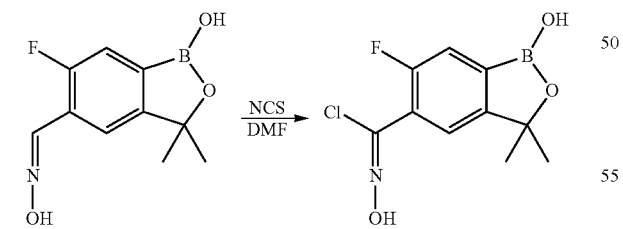

To a solution of the crude compound 6-fluoro-1-hydroxy-3,3-dimethyl-1,3-dihydrobenzo[c][1,2]oxaborole-5-carbaldehyde oxime (205 mg, 0.92 mmol) in DMF (4.0 mL) at rt was added NCS (147 mg, 1.1 mmol). The reaction mixture was stirred at 45° C. for 3 h. The mixture was cooled to rt, poured into ice-water and extracted with DCM (60 mL×3). The organic layer was washed with brine, dried over Na$_2$SO$_4$, filtered and concentrated under reduced pressure to give the crude compound 6-fluoro-N,1-dihydroxy-3,3-dimethyl-1,3-dihydrobenzo[c][1,2]oxaborole-5-carbimidoyl chloride as colorless oil. It was used in next step without further purification.

Step 12: Preparation of 5-(5-(3,5-dichlorophenyl)-5-(trifluoromethyl)-4,5-dihydro isoxazol-3-yl)-6-fluoro-3,3-dimethylbenzo[c][1,2]oxaborol-1(3H)-ol

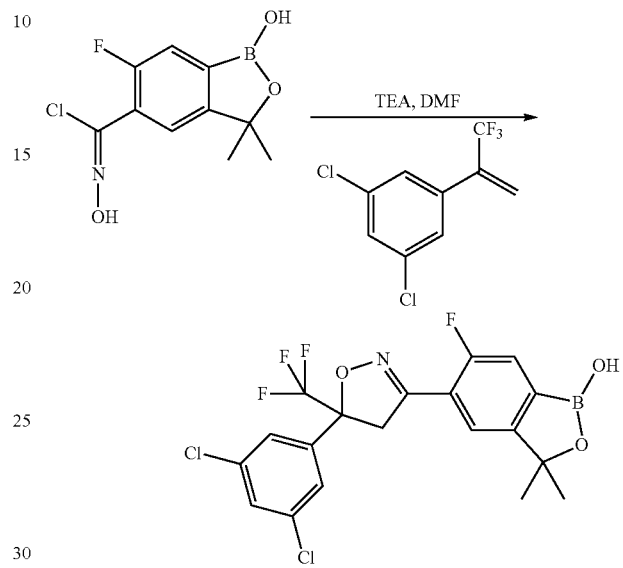

To a solution of the crude compound 6-fluoro-N,1-dihydroxy-3,3-dimethyl-1,3-dihydro benzo[c][1,2]oxaborole-5-carbimidoyl chloride (300 mg, 0.92 mmol) and 1,3-dichloro-5-(3,3,3-trifluoroprop-1-en-2-yl)benzene (222 mg, 0.92 mmol) in DMF (5 mL) at rt was added TEA (152 µL, 1.1 mmol). The reaction mixture was stirred for 12 h, poured into ice-water and extracted with DCM (60 mL×3). The organic layer was washed with brine, dried over Na$_2$SO$_4$, filtered and concentrated under reduced pressure. The residue was purified by prep-TLC eluted with PE-EA (3:2) and then purified by combiflash to give the title compound 5-(5-(3,5-dichlorophenyl)-5-(trifluoromethyl)-4,5-dihydro-isoxazol-3-yl)-6-fluoro-3,3-dimethylbenzo[c][1,2]oxaborol-1(3H)-ol (108 mg; yield 29% over 3 steps) as a white solid. $^1$H NMR (400 MHz, DMSO-d$_6$): δ 9.379 (s, 1H), 7.815-7.848 (m, 2H), 7.660 (s, 2H), 7.513 (d, J=10.0 Hz, 1H), 4.401 (d, J=18.4 Hz, 1H), 4.254 (d, J=18.8 Hz, 1H), 1.485 (s, 6H) ppm; HPLC purity: 100% at 220 nm and 100% at 254 nm; MS: m/z=462.0 (M+1, ESI+).

42. 6-Fluoro-3,3-dimethyl-5-(5-(3,4,5-trichlorophenyl)-5-(trifluoromethyl)-4,5-dihydroisoxazol-3-yl) benzo[c][1,2]oxaborol-1(3H)-ol

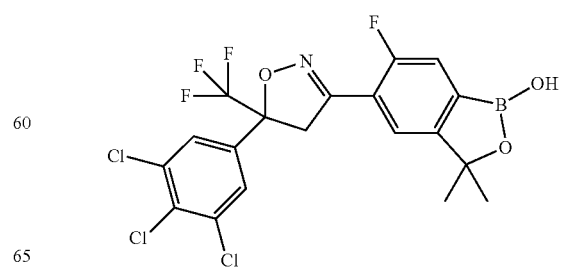

The title compound was synthesized by the following scheme:

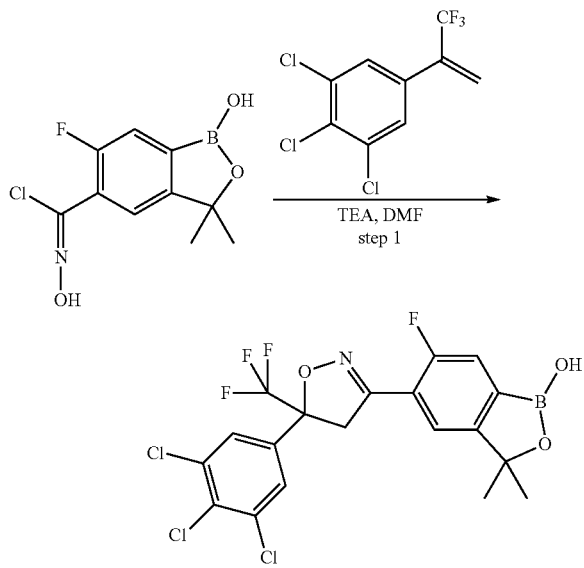

Step 1: Preparation of 6-fluoro-3,3-dimethyl-5-(5-(3, 4,5-trichlorophenyl)-5-(trifluoromethyl)-4,5-dihydroisoxazol-3-yl)benzo[c][1,2]oxaborol-1(3H)-ol To a solution of the crude compound 6-fluoro-N,1-dihydroxy-3,3-dimethyl-1,3-dihydrobenzo[c][1,2]oxaborole-5-carbimidoyl chloride (310 mg, 0.95 mmol) and 1,2,3-trichloro-5-(3,3,3-trifluoroprop-1-en-2-yl)benzene (262 mg, 0.95 mmol) in DMF (5 mL) at rt was added TEA (158 μL, 1.2 mmol). The reaction mixture was stirred for 12 h, poured into ice-water and extracted with DCM (60 mL×3). The organic layer was washed with brine, dried over $Na_2SO_4$, filtered and concentrated under reduced pressure. The residue was purified by prep-TLC eluted with PE-EA (3:2) and then purified by combiflash to give the title compound 6-fluoro-3,3-dimethyl-5-(5-(3,4,5-trichloro-phenyl)-5-(trifluoromethyl)-4,5-dihydroisoxazol-3-yl)benzo[c][1,2]oxaborol-1(3H)-ol (86 mg; yield 16% over 3 steps from the aldehyde) as a white solid. $^1$H NMR (500 MHz, DMSO-$d_6$): δ 9.352 (s, 1H), 7.875 (s, 2H), 7.826 (d, J=6.0 Hz, 1H), 7.513 (d, J=10.0 Hz, 1H), 4.399 (d, J=18.5 Hz, 1H), 4.274 (d, J=18.5 Hz, 1H), 1.482 (s, 6H) ppm; HPLC purity: 100% at 220 nm and 100% at 254 nm; MS: m/z=495.9 (M+1, ESI+).

EXAMPLE 2

Activity of Various Compounds Against Larval-stage Lone Star Ticks (*Amblyomma americanum*) in a Larval Immersion Microassay The larval immersion microassay was conducted as described in detail in White, et al., J. Med. Entomol. 41: 1034-1042 (2004). Compounds of the invention were formulated in dimethylsulfoxide (DMSO) to prepare a stock solution at a concentration of at least 10 mM. Using 96-well microtiter plates, an aliquot of the 10 mM sample was subsequently diluted in a water-based solution containing 1% ethanol and 0.2% Triton X-100, to obtain the desired concentration (typically 0.3 mM or lower) of compound in a volume of 0.1 ml (minimum n=3 replicates per compound or concentration). Approximately 30-50 Lone star tick larvae (*Amblyomma americanum*) were submerged into each well containing compounds. After a 30 minute immersion period, larvae were removed with a wide-bore pipette tip in 0.05 ml of fluid, dispensed into a commercial paper tissue biopsy bag which was sealed at the top with a plastic dialysis clip, inverted and allowed to air dry for 60 minutes. Bags containing larvae were then incubated at approximately 27 degrees Celsius and >90% relative humidity. After 24 hours, bags were opened, live and dead larvae were counted and percent larval mortality was calculated.

The following compounds exhibited ≥80% activity when tested in this assay at a concentration of no greater than 0.3 mM: 1, 2, 3, 5, 6, 7, 8, 9, 10, 11, 12, 14, 17, 19, 21, 22, 23, 24, 25, 26, 27, 28, 30, 32, 34, 35, 41, 42.

EXAMPLE 3

Efficacy of Various Compounds Against Nymphal-stage American Doe Ticks (*Dermacentor variabilis*) on Rats Evaluations were conducted using a modified version of the assay as described in Gutierrez et al., J. Med. Entomol. 43(3): 526-532 (2006). This assay may be modified by simply using different tick species (the reference describes *Amblyomma americanum* ticks), such as *Dermacentor variabilis* or *Rhipicephalus sanguineus* ticks, as well as different life-stages (larval, nymphal or adult). Further, the reference describes using topical application methods, but oral, transdermal and subcutaneous injection routes of administration may be used.

In these studies, adult male or female rats, approximately 300 grams in size, were randomly assigned to a treatment group or a control (untreated negative control or fipronil positive control) group. Each group consisted of three (3) to five (5) rats. One day before treatment (Day −1), rats were infested with approximately ten (10) *D. variabilis* tick nymphs, which were allowed to attach and begin feeding for 24 hours. On Day 0, rats in treated groups were orally administered compounds dissolved in polyethylene glycol-300, propylene glycol and water, at point dosages of 5-25 mg/kg bodyweight. Fipronil was prepared in similar fashion and administered orally at 10 mg/kg bodyweight. On Day 2, approximately forty-eight (48) hours after treatment, live and dead ticks were removed from animals and counted.

Live tick counts were transformed using the natural logarithm transformation plus one (Ln count+1); addition of one to each count served to adjust for counts that were zero. Geometric mean (GM) group tick counts were obtained via back-transformation of group mean transformed counts and subtracting one. The contemporaneous negative control group was used for comparison to the compound treatment groups for the calculation of percent efficacy (% reduction in live tick counts). GM percent efficacy of treatments was calculated using the following formula:

$$\% \text{ Efficacy} = \frac{A - B}{A} \times 100$$

A=GM No. Live Ticks Control; B=GM No. Live Ticks Treated

Efficacy results are illustrated in Table 1. Fipronil yielded >95% efficacy in all studies. No abnormal clinical signs or adverse effects attributable to test compounds were noted during any of the studies.

TABLE 1

Maximum in vivo efficacy obtained against *Dermacentor variabilis* ticks on rats for compounds administered orally at a point dose of between 5-25 mg/kg bodyweight.

| Compounds exhibiting efficacy <40% | Compounds exhibiting 40%≤ efficacy <80% | Compounds exhibiting efficacy ≥80% |
|---|---|---|
| 4 (0.0%), 9 (0.0%), 15 (0.0%), 18 (0.0%), 22 (0.0%), 29 (0.0%) 33 (0.0%), 36 (0.0%), 37 (0.0%), 38 (0.0%), 39 (0.0%), 40 (0.0%), 41 (0.0%), 42 (0.0%), 13 (7.1%), 16 (19.1%), 1 (21.8%), 12 (25.0%), 34 (25.5%), 20 (28.0%) | 30 (41.3%) | 28 (>80%); 14 (83.5%), 31 (88.0%), 24 (95.6%), 3 (97.9%), 2 (100%), 5 (100%), 6 (100%), 7 (100%), 8 (100%), 10 (100%), 11 (100%), 17 (100%), 19 (100%), 21 (100%), 23 (100%), 25 (100%), 26 (100%), 27 (100%), 32 (100%) 35 (100%) |

EXAMPLE 4

Efficacy of 7 Against Adult American Dog Tick (*Dermacentor variabilis*) and Cat Flea (*Ctenocephalides felis*) Infestations on Dogs The therapeutic (knockdown) and residual efficacy of 7, administered orally at a point dosages of 5 and 25 mg/kg bodyweight, was evaluated against adult American dog tick (*D. variabilis*) and cat flea (*C. felis*) infestations on dogs. Sixteen (16) male and female beagle dogs were allocated to one of four treatment groups: Untreated control group (n=4 dogs); 7, 5 mg/kg liquid oral dosage form (n=4 dogs); 7, 25 mg/kg liquid oral dosage form (n=4 dogs); and 7, 25 mg/kg solid oral dosage form. Liquid dosage forms were prepared by dissolving 7 in a solution of 55% polyethylene glycol-300, 35% propylene glycol and 10% water at 25 mg/ml. Solid oral dosage form was prepared by thoroughly mixing 7 with microcrystalline cellulose and croscarmellose sodium (50: 47:3, w/w) and placing into size 00 gelatin capsules. On Day 0, all dogs were orally administered 7 at the prescribed point dosages. Twenty-four (24) hours before treatment (Day −1), all dogs were infested with approximately 50 unfed, adult-stage American dog ticks (*D. variabilis*; approximately 50% male and 50% female). On Day 2, approximately 48 hours after treatment, ticks were removed and counts were conducted to determine the number and life-status classification of ticks present on all dogs (normal, moribund or dead; attached or detached). For all groups, dogs were re-infested with approximately 50 unfed, adult *D. variabilis* ticks on Days 5 and 12, with tick classification, counts and removal on Days 7 and 14 (approximately 48 hours after each infestation). For negative control and 7 (25 mg/kg solid oral dosage form) groups, dogs were re-infested with approximately 50 unfed, adult *D. variabilis* ticks on Days 19 and 28, with tick classification, counts and removal on Days 21 and 30. Immediately following removal of ticks on Day 30, dogs in the negative control and 7 (25 mg/kg solid oral dosage form) groups were infested with approximately 100 unfed, adult cat fleas (*C. felis*). Flea counts were conducted approximately 48 hours later, on Day 32.

The total number of live ticks or fleas (normal plus moribund classification) present on each dog was determined for each interval, and this number was transformed using the natural logarithm transformation plus one (Ln count+1); addition of one to each count served to adjust for counts that were zero. Geometric mean (GM) group tick or flea counts were obtained via back-transformation of group mean transformed counts and subtracting one. The negative control group was used for comparison to 7 groups for the calculation of percent efficacy (% reduction in live tick or flea counts). GM percent efficacy of treatments was calculated using the following formula:

$$\% \text{ Efficacy} = \frac{A - B}{A} \times 100$$

A=GM No. Live Ticks or Fleas Control; B=GM No. Live Ticks or Fleas Treated

Efficacy results are illustrated in Table 2. Both oral dosage forms at 25 mg/kg provided 100% therapeutic efficacy at 24 hour and 48 hour post-treatment time points against adult *D. variabilis* ticks. Residual efficacy was 93% and 98% on Day 7 for 25 mg/kg liquid and 25 mg/kg solid oral dosage form groups, respectively. By Day 14, efficacy of the 25 mg/kg solid oral dosage form was superior to the 25 mg/kg liquid oral dosage form (82% versus 52%). Residual tick efficacy of the 25 mg/kg solid oral dosage form was 74% at Day 21 and 62% at Day 30. The therapeutic and residual efficacy of the 5 mg/kg liquid oral dosage form was <70% at all intervals.

Activity against fleas was >95% with the 25 mg/kg solid oral dosage form on Day 32. Treatment with 7 was well tolerated by both dogs.

TABLE 2

Table 2. Geometric mean group live parasite counts (% efficacy) for 7, administered orally at 5 or 25 mg/kg bodyweight in liquid or solid oral dosage form, against tick (*Dermacentor variabilis*) and cat flea (*Ctenocephalides felis*) infestations on dogs.

| Treatment Group | D. variabilis | | | | | C. Felis |
|---|---|---|---|---|---|---|
| | Day 2 | Day 7 | Day 14 | Day 21 | Day 30 | Day 32 |
| Negative Control | 33.1 (—) | 35.5 (—) | 35.2 (—) | 26.3 (—) | 28.4 (—) | 80.1 (—) |
| 7 5 mg/kg (liquid) | 10.6 (68.2) | 36.5 (0.0) | 36.8 (0.0) | nd* | nd | nd |
| 7 25 mg/kg (liquid) | 0.0 (100) | 2.6 (92.8) | 16.9 (52.1) | nd | nd | nd |
| 7 25 mg/kg (solid) | 0.0 (100) | 0.7 (98.1) | 6.3 (82.2) | 6.8 (74.2) | 10.7 (62.2) | 3.9 (95.2) |

*nd, denotes not determined.

EXAMPLE 5

Efficacy of 7 and 8, Administered Orally at 25 mg/kg or 50 mg/kg, Against Adult American Dog Tick (*Dermacentor variabilis*) and Brown Dog Tick (*Rhipicephalus sanguineus*) Infestations on Dogs The therapeutic (knockdown) and residual efficacy of 7 and 8, each administered orally at a point dose of either 25 mg/kg or 50 mg/kg bodyweight, was evaluated against adult tick (*Dermacentor variabilis* and *Rhipicephalus sanguineus*) infestations on dogs. Twenty (20) male and female beagle dogs were allocated to one of five treatment groups, four (4) dogs per group: Untreated control; 7, 25 mg/kg; 7, 50 mg/kg; 8, 25 mg/kg; and 8, 50 mg/kg. On Day −1, all dogs were infested with approximately 50 unfed, adult *D. variabilis* ticks. On Day 0, dogs were orally administered gelatin capsules containing either 7 or 8 (50% technical active, 47% microcrystalline cellulose and 3% croscarmellose sodium, w/w) so as to achieve the desired point dosages. Ticks were counted and classified on all dogs, but not removed, on Day 1 (approximately 24 hours after treatment). On Day 2, approximately 48 hours after treatment, ticks were counted, classified and removed. Dogs were re-infested with the same number of *D. variabilis* ticks on Days 5, 12 and 19 with corresponding 48 hour post-infestation tick counts on Days 7, 14 and 21. Dogs were infested with approximately 50 unfed, adult brown dog ticks (*Rhipicephalus sanguineus*; approximately 50% male and 50% female) on Days 15 and 28, with corresponding 48 hour post-infestation tick counts on Days 17 and 30. GM percent efficacy of treatments against both tick species was calculated using the following formula:

$$\% \text{ Efficacy} = \frac{A - B}{A} \times 100$$

A=GM No. Live Ticks or Fleas Control; B=GM No. Live Ticks or Fleas Treated

Efficacy results are illustrated in Table 3. 7 and 8 yielded 100% therapeutic efficacy within 48 hours of treatment at both 25 and 50 mg/kg. Residual efficacy against *D. variabilis* ticks remained >90% for both compounds at both doses through Day 7 and declined thereafter. The residual efficacy of 7 at 50 mg/kg was high, 94% against a *R. sanguineus* infestation conducted between weeks 2 and 3. 7 and 8 were well tolerated by all dogs.

EXAMPLE 6

Efficacy of 7, Administered Orally at 25 mg/kg, Against Adult American Dog Tick (*Dermacentor variabilis*) Infestations on Dogs The efficacy of 7, administered orally at a point dose of 25 mg/kg bodyweight, was evaluated against adult tick (*Dermacentor variabilis*) infestations. Twelve (12) male and female beagle dogs were allocated to three treatment groups: Untreated, negative control A; 7 group B; and 7 group C (n=4 dogs per group). Dogs were infested with approximately 50 unfed, adult *D. variabilis* ticks on Days −1, 5, 12, 19 and 28. For 7 group B dogs, tick counts and classification were conducted at 48 hour post-treatment or post-infestation intervals on Days 2, 7, 14, 21 and 30. For negative control group A and 7 group C dogs, tick counts and classification were conducted at 72 hour post-treatment or post-infestation intervals on Days 3, 8, 15, 22 and 31. On Day 0, dogs in groups B and C were orally administered gelatin capsules containing 7 (50% technical active, 47% microcrystalline cellulose and 3% croscarmellose sodium, w/w) at a point dose of 50 mg/kg. Both 48 hour and 72 hour counts in the treated groups were adjusted to counts from the same 72 hour negative control group. GM percent efficacy of treatments was calculated using the following formula:

$$\% \text{ Efficacy} = \frac{A - B}{A} \times 100$$

A=GM No. Live Ticks Control; B=GM No. Live Ticks Treated

Efficacy results are illustrated in Table 4. Therapeutic (knockdown) activity of 7, when administered orally at 50 mg/kg, was 99% within 48 hours of treatment and 100% at 72 hours. Residual efficacy at 48 hour intervals was <90% through week 4 (Day 30), but was >99% using 72 hour count intervals through week 3 (Day 22) and 97% at week 4 (Day 31). A substantial number of moribund ticks was observed on 7 group B dogs at 48 hour intervals and was responsible for observed decline in residual efficacy for this group. Very few moribund ticks were observed on 7 group C dogs at the 72 hour intervals, contributing to very good residual efficacy. Treatments were well tolerated by all dogs.

TABLE 3

Table 3. Geometric mean group live tick counts (% efficacy) for 7 and 8, administered orally at point dosages of 25 or 50 mg/kg, against tick (*Dermacentor variabilis* and *Rhipicephalus sanguineus*) infestations on dogs.

| Treatment Group | D. variabilis | | | | | R. sanguineus | |
|---|---|---|---|---|---|---|---|
| | Day 1 | Day 2 | Day 7 | Day 14 | Day 21 | Day 17 | Day 30 |
| Negative Control | 10.5 (—) | 10.0 (—) | 22.9 (—) | 16.5 (—) | 16.2 (—) | 27.1 (—) | 37.1 (—) |
| 7 25 mg/kg | 1.0 (90.4) | 0.0 (100) | 0.7 (97.0) | 5.3 (67.6) | 4.7 (71.1) | 8.0 (75.0) | nd* |
| 7 50 mg/kg | 1.8 (83.0) | 0.0 (100) | 0.4 (98.2) | 1.9 (88.5) | 3.2 (80.1) | 1.6 (94.0) | 13.4 (63.9) |
| 8 25 mg/kg | 2.0 (81.0) | 0.0 (100) | 1.5 (93.4) | 2.5 (85.0) | 3.4 (79.3) | 7.2 (73.4) | nd |
| 8 50 mg/kg | 2.0 (80.9) | 0.0 (100) | 0.6 (97.5) | 3.2 (80.4) | 4.0 (75.1) | 5.4 (80.2) | 21.5 (42.1) |

*nd, denotes not determined.

TABLE 4

Table 4. Geometric mean group live tick counts (% efficacy) of 7, administered orally at 50 mg/kg bodyweight, against American dog tick (*Dermacentor variabilis*) infestations on dogs.

| | \multicolumn{10}{c}{*D. variabilis*} |
|---|---|---|---|---|---|---|---|---|---|---|
| | Week 0 | | Week 1 | | Week 2 | | Week 3 | | Week 4 | |
| | 48 h | 72 h | 48 h | 72 h | 48 h | 72 h | 48 h | 72 h | 48 h | 72 h |
| Negative Control* | 21.6 (—) | | 17.3 (—) | | 28.1 (—) | | 12.3 (—) | | 25.3 (—) | |
| 7, 50 mg/kg | 0.3 (98.5) | 0.0 (100) | 2.6 (85.1) | 0.0 (100) | 6.1 (78.3) | 0.2 (99.3) | 10.7 (13.0) | 0.0 (100) | 16.3 (35.5) | 0.8 (96.9) |

*Same control group (72 h) counts were used for comparison to 48 h and 72 h treated group counts.

EXAMPLE 7

Therapeutic Efficacy and Speed of Kill for 7, Administered Orally at 25 mg/kg, Against Adult Cat Flea (*Ctenocephalides felis*) Infestations on Dogs The therapeutic efficacy and speed of kill of 7, administered orally at a point dose of 25 mg/kg bodyweight, was evaluated against adult cat flea (*Ctenocephalides felis*) infestations on dogs. Twelve (12) male and female beagle dogs were allocated to one of four treatment groups (n=3 dogs per group). Group A was untreated, negative control; groups B, C and D received 7. On Day −1, all dogs were infested with approximately 100 unfed, adult fleas (approximately 50% male and 50% female). On Day 0, dogs in groups B, C and D were orally administered gelatin capsules containing 7, at a point dose of 25 mg/kg (50% technical active, 47% microcrystalline cellulose and 3% croscarmellose sodium, w/w). At eight (8) hours post-treatment, fleas were counted and removed from dogs in group B; at twelve (12) hours post-treatment, fleas were counted and removed from dogs in group C; and at twenty-four (24) hours post-treatment, fleas were counted and removed from dogs in groups A and D. GM percent efficacy of treatments against fleas was calculated using the following formula:

$$\% \text{ Efficacy} = \frac{A - B}{A} \times 100$$

A=GM No. Live Fleas Control; B=GM No. Live Fleas Treated

Efficacy results are illustrated in Table 5. 7 provided rapid knockdown against an existing flea infestation on dogs within twelve (12) hours of treatment, and 100% efficacy within twenty-four (24) hours of treatment. Treatments were well tolerated by dogs.

TABLE 5

Geometric mean group live flea counts (% efficacy) of 7, administered orally at 25 mg/kg bodyweight, against cat flea (*C. felis*) infestations on dogs at the indicated post-treatment interval.

| Treatment Group | Post-Treatment Interval | | |
|---|---|---|---|
| | 8 hours | 12 hours | 24 hours |
| Negative Control* | | 85.7 (—) | |
| 7 25 mg/kg | 75.6 (11.8) | 0.3 (99.7) | 0.0 (100) |

*7 counts at all intervals were adjusted to the same count conducted on negative control dogs at 24 hours post-treatment.

EXAMPLE 8

Biological Characterization and Comparison of the R and S Enantiomers of 7

7 contains one chiral center, and is therefore a racemic mixture comprised of approximately 50% R- and 50% S-enantiomer. In vitro and surrogate animal (rat) studies were conducted to evaluate the biological activity of the R- and S-enantiomers of 7. For the in vitro study, larvae of the Lone star tick (*Amblyomma americanum*) were exposed to 17 (S-enantiomer) and 18 (R-enantiomer) using the larval immersion microassay at a concentration of no greater than 0.3 mM. Following exposure, larvae were removed, transferred to a tissue biopsy bag and incubated at approximately 27 degrees Celsius and >90% relative humidity. After 24 hours, biopsy bags were opened and the numbers of live and dead larvae were determined.

Enantiomers were evaluated for activity against American dog tick (*Dermacentor variabilis*) nymphs on rats. One day before treatment (Day −1), treated and negative control rats (n=3 to 5 rats per group) were infested with approximately ten (10) *D. variabilis* tick nymphs, which were allowed to attach and begin feeding for 24 hours. On Day 0, rats in treated groups were orally administered compounds dissolved in polyethylene glycol-300, propylene glycol and water, at point dosages of no greater than 5 mg/kg bodyweight. Fipronil was prepared in similar fashion and administered orally at 10 mg/kg bodyweight. On Day 2, approximately forty-eight (48) hours after treatment, live and dead ticks were removed from animals and counted. GM percent efficacy of treatments was calculated using the following formula:

$$\% \text{ Efficacy} = \frac{A - B}{A} \times 100$$

A=GM No. Live Ticks Control; B=GM No. Live Ticks Treated

Enantiomer activity profiles are illustrated in Table 6. R-enantiomer 18 was inactive (0.0%) against *Amblyomma americanum* larvae in the in vitro larval immersion microassay at a concentration of 0.3 mM, whereas S-enantiomer 17 yielded ≥80% activity at a concentration of 0.3 mM. When administered orally to *D. variabilis* nymph infested rats at point doses of ≤5 mg/kg, 18 was inactive (10.7% tick reduction) whereas 17 was active (≥80% tick reduction). Treatment with both enantiomers was well tolerated by all rats.

TABLE 6

In vitro and in vivo comparative activity of R and S enantiomers against tick larvae and nymphs.

| Compound ID | Enantiomer | In vitro activity at 0.3 mM | % Efficacy at Dose of ≤5 mg/kg |
|---|---|---|---|
| Racemate Parent 7 | | | |
| 17 | S | 100% | ≥80% |
| 18 | R | 0.0% | 10.7% |

EXAMPLE 9

Efficacy of 17, Administered Orally at 50 mg/kg, Against Adult American Dog Tick (*Dermacentor variabilis*), Brown Dog Tick (*Rhipicephalus sanguineus*) and Cat Flea (*Ctenocephalides felis*) Infestations on Dogs The therapeutic (knockdown) and residual efficacy of 17, administered orally at a point dose of 50 mg/kg bodyweight, was evaluated against adult tick (*Dermacentor variabilis* and *Rhipicephalus sanguineus*) and adult cat flea (*Ctenocephalides felis*) infestations on dogs. Eight (8) male and female beagle dogs were allocated to either an untreated, negative control group or 17 group (n=4 dogs per group). Dogs were infested with approximately 50 unfed, adult *D. variabilis* ticks on Days −1, 5, 12, 19, and 28. On Day 0, dogs were orally administered gelatin capsules containing 17 (50% technical active, 47% microcrystalline cellulose and 3% croscarmellose sodium, w/w) at a point dose of 50 mg/kg. *D. variabilis* tick counts and classification were conducted on Day 1 (thumb count, approximately 24 hours after treatment) and Days 2, 7, 14, 21 and 30 (approximately 48 hours after treatment). Following removal of *D. variabilis* ticks on Day 30, all dogs were co-infested with approximately 50 unfed, adult brown dog ticks (*R. sanguineus*) and approximately 100 unfed, adult cat fleas (*C. felis*). Brown dog tick and cat flea counts were conducted on Day 32 (approximately 48 hours after infestation). GM percent efficacy of treatments against both tick species and fleas was calculated using the following formula:

$$\% \text{ Efficacy} = \frac{A-B}{A} \times 100$$

A=GM No. Live Ticks or Fleas Control; B=GM No. Live Ticks or Fleas Treated

Efficacy results are illustrated in Table 7. Against *D. variabilis*, 17 demonstrated 98% knockdown within 24 hours of treatment; 100% within 48 hours treatment; excellent residual efficacy of 97-100% through Day 21 and 95% on Day 30. On Day 32, 17 yielded 94% efficacy against *R. sanguineus* ticks and 100% control of fleas. Oral treatment with 17 was well tolerated by all dogs.

TABLE 7

Geometric mean group live parasite counts (% efficacy) of 17 administered orally at 50 mg/kg bodyweight, against tick (*Dermacentor variabilis* and *Rhipicephalus sanguineus*) and cat flea (*Ctenocephalides felis*) infestations on dogs.

| Treatment Group | D. variabilis | | | | | | R. Sanguineus | C. felis |
|---|---|---|---|---|---|---|---|---|
| | Day 1 | Day 2 | Day 7 | Day 14 | Day 21 | Day 30 | Day 32 | Day 32 |
| Negative Control | 28.4 (—) | 33.8 (—) | 30.6 (—) | 36.9 (—) | 36.2 (—) | 39.4 (—) | 32.3 (—) | 59.2 (—) |
| 17 50 mg/kg | 0.7 (97.6) | 0.0 (100) | 0.0 (100) | 1.2 (96.7) | 0.0 (100) | 1.9 (95.3) | 1.9 (94.1) | 0.0 (100) |

It is to be understood that the invention covers all combinations of aspects with all other suitable aspects and/or exemplary embodiments described herein. It is to be understood that the invention also covers all combinations of exemplary embodiments with all other suitable aspects and/or exemplary embodiments described herein.

What is claimed is:

1. A compound having a structure of formula (I):

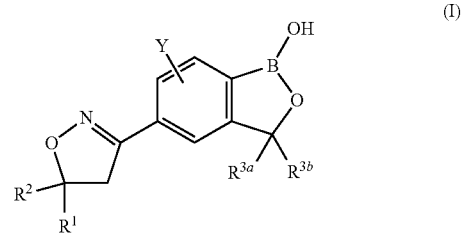

wherein
Y is hydrogen, fluoro, chloro, or bromo;
$R^1$ is phenyl substituted 2-4 times, said substitutions comprising i) 1-4 substitutions with the same or different of halo, and 0-1 substitutions with methyl, difluoromethyl, trifluoromethyl, methoxy, trifluormethoxy, or trifluoroethoxy, or ii) 2 trifluoromethyl groups;
$R^2$ is methyl, fluoromethyl, trifluoromethyl, or perfluoroethyl;
$R^{3a}$ and $R^{3b}$ are independently selected from hydrogen, methyl, ethyl, or fluoromethyl, or $R^{3a}$ and $R^{3b}$ combine with the carbon to which they are attached to form a cyclopentyl ring or a cyclohexyl ring;
or a salt thereof.

2. The compound of claim 1 having a structure which is:

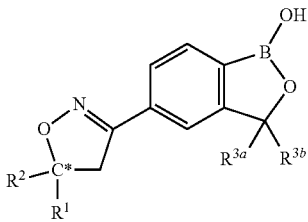

wherein C* is a carbon atom which is a stereocenter having a (S) configuration.

3. The compound of claim 1 having a structure which is:

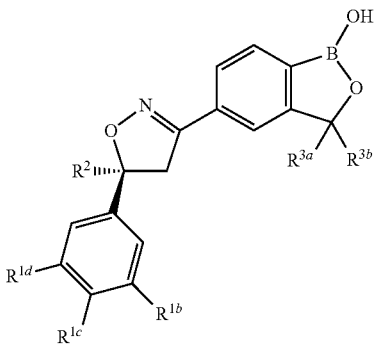

wherein
$R^{1b}$, $R^{1c}$ and $R^{1d}$ are each independently selected from hydrogen, fluoro, chloro, bromo, methyl, difluoromethyl, trifluoromethyl, methoxy, trifluormethoxy, or trifluoroethoxy, and
$R^{3a}$ and $R^{3b}$ are the same and selected from methyl or fluoromethyl.

4. The compound of claim 1 having a structure which is:

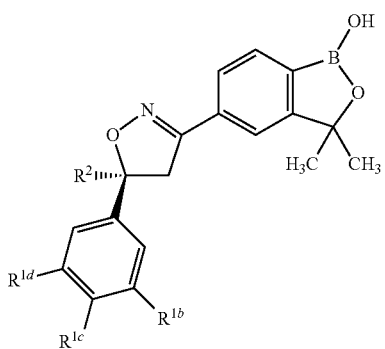

wherein $R^2$ is trifluoromethyl; and $R^{1b}$, $R^{1c}$, and $R^{1d}$ are each independently selected from hydrogen, fluoro, chloro, or bromo.

5. The compound of claim 4 wherein $R^{1b}$ is fluoro, chloro, or bromo; $R^{1c}$ is hydrogen, fluoro, or chloro; and $R^{1d}$ is fluoro, chloro, or bromo.

6. The compound of claim 1 wherein the compound is selected from
5-(5-(3,5-Dichlorophenyl)-5-(trifluoromethyl)-4,5-dihydroisoxazol-3-yl)benzo[c][1,2]oxaborol-1(3H)-ol;
5-(5-(3,5-Dichlorophenyl)-5-(trifluoromethyl)-4,5-dihydroisoxazol-3-yl)-3,3-dimethyl -benzo[c][1,2]oxaborol-1(3H)-ol;
(S)-5-(5-(3,5-dichlorophenyl)-5-(trifluoromethyl)-4,5-dihydroisoxazol-3-yl)-3,3-dimethylbenzo[c][1,2]oxaborol-1(3H)-ol;
(R)-5-(5-(3,5-dichlorophenyl)-5-(trifluoromethyl)-4,5-dihydroisoxazol-3-yl)-3,3-dimethylbenzo[c][1,2]oxaborol-1(3H)-ol;
5-(5-(3,5-Dibromophenyl)-5-(trifluoromethyl)-4,5-dihydroisoxazol-3-yl)-3,3-dimethyl-benzo[c][1,2]oxaborol-1(3H)-ol;
5-(5-(3-Chloro-5-(trifluoromethyl)phenyl)-5-(trifluoromethyl)-4,5-dihydroisoxazol-3-yl)-3,3-dimethylbenzo[c][1,2]oxaborol-1(3H)-ol;
3,3-Dimethyl-5-(5-(3,4,5-trichlorophenyl)-5-(trifluoromethyl)-4,5-dihydroisoxazol-3-yl)benzo[c][1,2]oxaborol-1(3H)-ol;
5-(5-(3,5-Dichlorophenyl)-5-(trifluoromethyl)-4,5-dihydroisoxazol-3-yl)-3,3-dimethyl-benzo[c][1,2]oxaborol-1(3H)-ol;
5-(5-(3,5-Dichloro-4-methylphenyl)-5-(trifluoromethyl)-4,5-dihydroisoxazol-3-yl)-3,3-dimethylbenzo[c][1,2] oxaborol-1(3H)-ol;
5-(5-(3,5-Dichloro-4-(trifluoromethyl)phenyl)-5-(trifluoromethyl)-4,5-dihydro isoxazol-3-yl)-3,3-dimethylbenzo[c][1,2]oxaborol-1(3H)-ol;
5-(5-(3,5-Dichloro-4-(difluoromethyl)phenyl)-5-(trifluoromethyl)-4,5-dihydro isoxazol-3-yl)-3,3-dimethylbenzo[c][1,2]oxaborol-1(3H)-ol;
5-(5-(3,5-Dichloro-4-(trifluoromethoxy)phenyl)-5-(trifluoromethyl)-4,5-dihydro -isoxazol-3-yl)-3,3-dimethylbenzo[c][1,2]oxaborol-1(3H)-ol;
5-(5-(3,5-Dichlorophenyl)-5-(perfluoroethyl)-4,5-dihydroisoxazol-3-yl)-3,3-dimethylbenzo[c][1,2]oxaborol-1(3H)-ol;
5-(5-(3,5-Bis(trifluoromethyl)phenyl)-5-(trifluoromethyl)-4,5-dihydroisoxazol-3-yl)-3,3-dimethylbenzo[c][1,2]oxaborol-1(3H)-ol;
5-(5-(3,5-Dichloro-4-(2,2,2-trifluoroethoxy)phenyl)-5-(trifluoromethyl)-4,5-dihydroisoxazol-3-yl)-3,3-dimethylbenzo[c][1,2]oxaborol-1(3H)-ol;
3,3-Dimethyl-5-(5-methyl-5-(3,4,5-trichlorophenyl)-4,5-dihydroisoxazol-3-yl)benzo[c][1,2]oxaborol-1(3H)-ol;
(S)-3,3-Dimethyl-5-(5-(3,4,5-trichlorophenyl)-5-(trifluoromethyl)-4,5-dihydroisoxazol-3-yl)benzo[c][1,2]oxaborol-1(3H)-ol;
(R)-3,3-Dimethyl-5-(5-(3,4,5-trichlorophenyl)-5-(trifluoromethyl)-4,5-dihydroisoxazol-3-yl)benzo[c][1,2]oxaborol-1(3H)-ol;
5-(5-(3-Chloro-4-fluorophenyl)-5-(trifluoromethyl)-4,5-dihydroisoxazol-3-yl)-3,3-dimethylbenzo[c][1,2]oxaborol-1(3H)-ol;
5-(5-(Fluoromethyl)-5-(3,4,5-trichlorophenyl)-4,5-dihydroisoxazol-3-yl)-3,3-dimethylbenzo[c][1,2]oxaborol-1(3H)-ol;
5-(5-(4-Bromo-3,5-dichlorophenyl)-5-(trifluoromethyl)-4,5-dihydroisoxazol-3-yl)-3,3-dimethylbenzo[c][1,2] oxaborol-1(3H)-ol;
5-(5-(3,5-Dichloro-4-methoxyphenyl)-5-(trifluoromethyl)-4,5-dihydroisoxazol-3-yl)-3,3-dimethylbenzo[c][1,2]oxaborol-1(3H)-ol;
5-(5-(3,4-Dichlorophenyl)-5-(trifluoromethyl)-4,5-dihydroisoxazol-3-yl)-3,3-dimethyl-benzo[c][1,2]oxaborol-1(3H)-ol;

5-(5-(4-Fluoro-3-(trifluoromethyl)phenyl)-5-(trifluoromethyl)-4,5-dihydroisoxazol-3-yl)-3,3-dimethylbenzo[c][1,2]oxaborol-1(3H)-ol;
5-(5-(3-Chloro-4,5-difluorophenyl)-5-(trifluoromethyl)-4,5-dihydroisoxazol-3-yl)-3,3-dimethylbenzo[c][1,2]oxaborol-1(3H)-ol;
5-(5-(3,4-Dichloro-5-fluorophenyl)-5-(trifluoromethyl)-4,5-dihydroisoxazol-3-yl)-3,3-dimethylbenzo[c][1,2]oxaborol-1(3H)-ol;
5-(5-(3,5-Dibromo-4-chlorophenyl)-5-(trifluoromethyl)-4,5-dihydroisoxazol-3-yl)-3,3-dimethylbenzo[c][1,2]oxaborol-1(3H)-ol;
(S)-5-(5-(3,5-Dichloro-4-fluorophenyl)-5-(trifluoromethyl)-4,5-dihydroisoxazol-3-yl)-3,3-dimethylbenzo[c][1,2]oxaborol-1(3H)-ol;
(R)-5-(5-(3,5-Dichloro-4-fluorophenyl)-5-(trifluoromethyl)-4,5-dihydroisoxazol-3-yl)-3,3-dimethylbenzo[c][1,2]oxaborol-1(3H)-ol;
5-(5-(4-Chloro-3,5-difluorophenyl)-5-(trifluoromethyl)-4,5-dihydroisoxazol-3-yl)-3,3-dimethylbenzo[c][1,2]oxaborol-1(3H)-ol;
3,3-Dimethyl-5-(5-(trifluoromethyl)-5-(3,4,5-trifluorophenyl)-4,5-dihydroisoxazol-3-yl)benzo[c][1,2]oxaborol-1(3H)-ol;
5-(5-(3,5-Dibromo-4-fluorophenyl)-5-(trifluoromethyl)-4,5-dihydroisoxazol-3-yl)-3,3-dimethylbenzo[c][1,2]oxaborol-1(3H)-ol;
3,3-Bis(fluoromethyl)-5-(5-(3,4,5-trichlorophenyl)-5-(trifluoromethyl)-4,5-dihydroisoxazol-3-yl)benzo[c][1,2]oxaborol-1(3H)-ol;
3,3-Dimethyl-5-(5-(2,3,4,5-tetrachlorophenyl)-5-(trifluoromethyl)-4,5-dihydroisoxazol-3-yl)benzo[c][1,2]oxaborol-1(3H)-ol;
5-(5-(3,5-Dichloro-2,4-difluorophenyl)-5-(trifluoromethyl)-4,5-dihydroisoxazol-3-yl)-3,3-dimethylbenzo[c][1,2]oxaborol-1(3H)-ol;
5-(5-(3,5-Dichlorophenyl)-5-(trifluoromethyl)-4,5-dihydroisoxazol-3-yl)-3,3-diethyl-benzo[c][1,2]oxaborol-1(3H)-ol;
5-(5-(3,5-Dichlorophenyl)-5-(trifluoromethyl)-4,5-dihydroisoxazol-3-yl)-1H-spiro[benzo[c][1,2]oxaborole-3,1'-cyclopentan]-1-ol;
5-(5-(3,5-Dichlorophenyl)-5-(trifluoromethyl)-4,5-dihydroisoxazol-3-yl)-1H-spiro[benzo[c][1,2]oxaborole-3,1'-cyclopentan]-1-ol;
5-(5-(3,5-Dichlorophenyl)-5-(trifluoromethyl)-4,5-dihydroisoxazol-3-yl)-4-fluoro-3,3-dimethylbenzo[c][1,2]oxaborol-1(3H)-ol;
4-Fluoro-3,3-dimethyl-5-(5-(3,4,5-trichlorophenyl)-5-(trifluoromethyl)-4,5-dihydroisoxazol-3-yl)benzo[c][1,2]oxaborol-1(3H)-ol;
5-(5-(3,5-dichlorophenyl)-5-(trifluoromethyl)-4,5-dihydroisoxazol-3-yl)-6-fluoro-3,3-dimethylbenzo[c][1,2]oxaborol-1(3H)-ol; or
6-Fluoro-3,3-dimethyl-5-(5-(3,4,5-trichlorophenyl)-5-(trifluoromethyl)-4,5-dihydroisoxazol-3-yl)benzo[c][1,2]oxaborol-1(3H)-ol, or a salt thereof.

7. The compound of claim 1, or a salt thereof, wherein it is (R)-3,3-Dimethyl-5-(5-(3,4,5-trichlorophenyl)-5-(trifluoromethyl)-4,5-dihydroisoxazol-3-yl)benzo[c][1,2]oxaborol-1(3H)-ol.

8. The compound of claim 1, or a salt thereof, wherein it is 3,3-Dimethyl-5-(5-(2,3,4,5-tetrachlorophenyl)-5-(trifluoromethyl)-4,5-dihydroisoxazol-3-yl)benzo[c][1,2]oxaborol-1(3H)-ol.

9. A formulation comprising a compound of claim 1, or a salt thereof, and at least one pharmaceutically acceptable excipient.

10. The formulation of claim 9, wherein said formulation further comprises at least one additional active ingredient.

11. The formulation of claim 9, wherein said formulation is a human pharmaceutical formulation.

12. The formulation of claim 9, wherein said formulation is a veterinary pharmaceutical formulation.

13. The formulation of claim 12 wherein said formulation is an oral formulation.

14. The formulation of claim 13 wherein said formulation is in unit dosage form.

15. A method of killing and/or preventing the growth of an ectoparasite, comprising contacting said ectoparasite with an effective amount of a compound of claim 1, or a salt thereof.

16. The method of claim 15, wherein the ectoparasite is a tick or a flea.

17. The method of claim 16, wherein the ectoparasite is in or on an animal.

18. A method of controlling an ectoparasitic infestation in or on an animal in need of treatment thereof, comprising administering to said animal a therapeutically effective amount of a compound of claim 1, or a salt thereof.

19. The method of claim 18, wherein said animal is a dog or a cat.

20. The method of claim 19 wherein said administration is oral and said ectoparasite is a tick or flea.

* * * * *